(12) United States Patent
Hamers et al.

(10) Patent No.: US 7,794,981 B2
(45) Date of Patent: *Sep. 14, 2010

(54) PROSUCTION OF ANTIBODIES OR (FUNCTIONALIZED) FRAGMENTS THEREOF DERIVED FROM HEAVY CHAIN IMMUNOGLOBULINS OF CAMELIDAE

(75) Inventors: Raymond Hamers, Sint-Genesius-Rode (BE); Cecile Hamers-Casterman, Sint-Genesius-Rode (BE); Serge V. M. Muyldermans, Hoeilaart (BE); Leon G. J. Frenken, MP Rotterdam (NL); Cornelis T Verrips, KB Maassluis (NL)

(73) Assignee: BAC IP B.V., Naarden (NL)

( * ) Notice: Subject to any disclaimer, the term of this patent is extended or adjusted under 35 U.S.C. 154(b) by 243 days.

This patent is subject to a terminal disclaimer.

(21) Appl. No.: 10/915,490

(22) Filed: Aug. 11, 2004

(65) Prior Publication Data
US 2005/0130266 A1    Jun. 16, 2005

Related U.S. Application Data

(63) Continuation of application No. 08/537,871, filed as application No. PCT/EP94/01442 on Apr. 28, 1994, now Pat. No. 6,838,254.

(30) Foreign Application Priority Data

Apr. 29, 1993  (EP) ................................. 93201239
May 19, 1993   (EP) ................................. 93201454
Jul. 15, 1993   (EP) ................................. 93202079

(51) Int. Cl.
C12P 21/08    (2006.01)
C07K 16/00    (2006.01)

(52) U.S. Cl. .................... 435/70.21; 435/71.1; 435/71.2
(58) Field of Classification Search ........................ None
See application file for complete search history.

(56) References Cited

U.S. PATENT DOCUMENTS 5,759,808 A   6/1998  Casterman et al.
5,770,445 A   6/1998  Kindsvogel et al.
6,005,079 A   12/1999 Casterman et al.

FOREIGN PATENT DOCUMENTS

| ER | 0 256 421 | 2/1988 |
| GR | 0 125 023 | 11/1984 |
| HR | 0 584 421 A1 | 3/1994 |
| WO | WO 89/09825 | 10/1989 |
| WO | WO 91/08482 | 6/1991 |
| WO | WO 93/02198 | 2/1993 |
| WO | WO 94/04678 | 3/1994 |

OTHER PUBLICATIONS

Hamers et al., Letters to Nature, 363:446-449 (Jun. 3, 1993).
Davies et al., FEBS Letters, 339:285-290 (1994).
Ward et al. Nature, 341:544-546 (1989).
Ungar-Waron et al., Isr. J. Vet. Med., 43(3):198-203 (1987).
Jones et al., Nature, 321:522-525 (1986).
Dunnich et al., Nucleic Acids Research, 8(7):1475-1484 (1980).
Hochman et al., Biochemistry, 12(6):1130-1135 (1973).
Berry et al., Journal of Chromatography, 597:239-245 (1992).
Hodgson, Biotechnology, 9:421-424 (1991).
Breitling et al., Gene, 184:147-153 (1991).
J. Rudinger in Peptide Hormones, J.A. Parsons (Ed.), University of Park Press, Baltimore, MD, pp. 1-7 (Jun. 1979).
Ngo et al., Computational Complexity, Protein Structure Prediction and the Levinthal Paradox, The Protein Folding Problem and Tertiary Structure Prediction, K. Merz, Jr., and S. Le Grant, Editors, Birkhauser Boston, pp. 491-495 (1994).

*Primary Examiner*—Ram R Shukla
*Assistant Examiner*—Marianne Dibrino
(74) *Attorney, Agent, or Firm*—Morgan Lewis & Bockius LLP

(57) ABSTRACT

A process is provided for the production of an antibody or a fragment or functionalized fragment thereof using a transformed lower eukaryotic host containing an example DNA sequence encoding the antibody or (functionalized) fragment thereof, wherein the antibody or (functionalized) fragment thereof is derived from a heavy chain immunoglobulin of Camelidae and is devoid of light chains, and wherein the lower eukaryotic host is a mould, preferably belonging to the genera *Aspergillus* or *Trichoderma*, or a yeast, preferably belonging to the yeast genera *Saccharomyces*, *Kluyveromyces*, *Hansenula*, or *Pichia*. The heavy chain fragment can contain at least the whole variable domain. A complementary determining region (CDR) different from the CDR belonging to the natural antibody ex Camelidae can be grafted on the framework of the variable domain of the heavy chain immunoglobulin. The catalytic antibodies can be raised in Camelidae against transition state molecules. The functionalized antibody or fragment thereof can comprise a fusion protein of both a heavy chain immunoglobulin from Camelidae or a fragment thereof and another polypeptide, e.g., an enzyme, preferably an oxido-reductase. Also provided are new products obtainable by a process as described, and compositions containing a product produced by a process as described, which composition may contain a new product as provided.

7 Claims, 20 Drawing Sheets

```
                              10         20              40
human(subgroupIII)  EVQLVESGGG LVQPGGSLRL SCAASG :CDR1: WVRQA PGKGLEWVS :CDR2:
camel A                     GG SVQGGGSLRL SCAISG :CDR1: WFREG PGKEREGIA :CDR2:
camel B                     GG SVQAGGSLRL SCASSS :CDR1: WYRQA PGKEREFVS :CDR2:

70          80          90                    110
         RFTIS RDNSKNTLYL QMNSLRAEDTAVY YCAR :CDR3: WGQGTLVT VSS
         RFTIS QDSTLKTMYL LMNNLKPEDTGTY YCAA :CDR3: WGQGTQVT VSS
         RFTIS QDSAKNTVYL QMNSLKPEDTAMY YCKI :CDR3: WGQGTQVT VSS
```

FIG. 3A

```
                 camel V_H        :    hinge             :      C_H 2
          WGQGTQVT VSS :—— GTNEVCKCPKCP :APELPGG PSVFVFP
camel     WGQGTQVT VSS :— EPKIPQPQPKPQPQP:
                       :   QPQPKPQP    :
                       : KPEPECTCPKCP :APELLGG PSVFIFP
         ---------------------------------------------------
                 human C_H 1       :    hinge             :      C_H 2
         human gamma 3    KVDKRV :ELKTPLGDTTHTCPRCP:
                                 : EPKCSDTPPPCPRCP :
                                 : EPKSCDTPPPCPRCP :APELLGG PSVFLFP
         human gamma 1    KVDKK  —AEPKSCDTPPPCPRCP:APELLGG PSVFLFP
         human gamma 2    KVKVTV :—— ERKCCVECPPCP :APPVAG - PSVFLFP
         human gamma 4    KVDKRV :—— ESKYGPPCPSCP :APEFLGG PSVFLFP
```

FIG. 3B

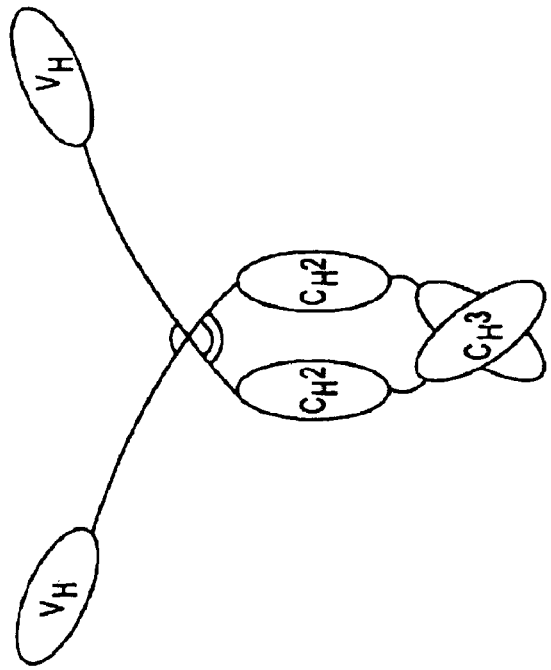
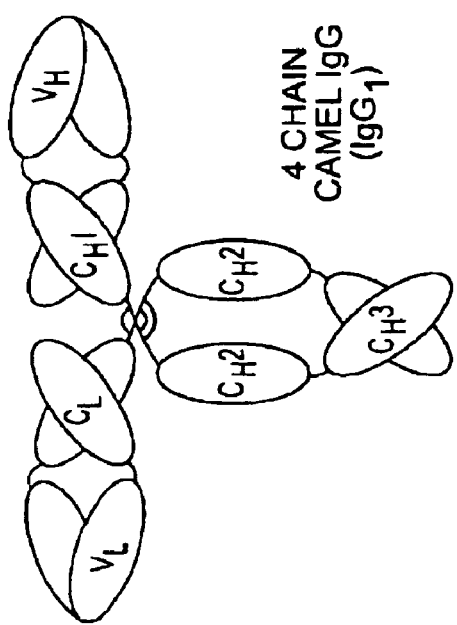
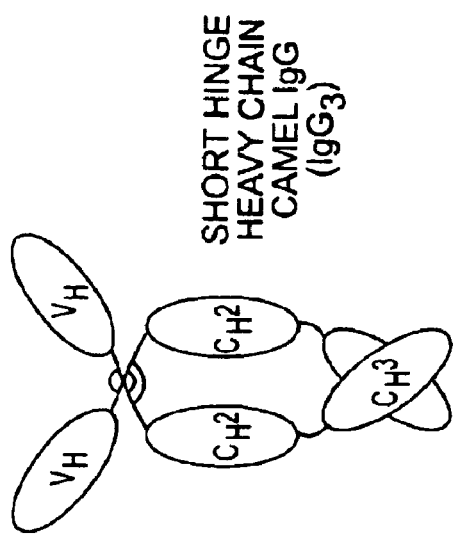
FIG. 4A — 4 CHAIN CAMEL IgG (IgG₁)
FIG. 4B — SHORT HINGE HEAVY CHAIN CAMEL IgG (IgG₃)
FIG. 4C — LONG HINGE HEAVY CHAIN CAMEL IgG (IgG₂)

```
                XhoI
     CAGGTGAAACTGCTCGAGTCTGGAGGAGGCTCGGTGCAGACTGGAGGATCTCTGAGACTC
  1  ---------+---------+---------+---------+---------+---------+  60
     GTCCACTTTGACGAGCTCAGACCTCCTCCGAGCCACGTCTGACCTCCTAGAGACTCTGAG

Q  V  K  L  L  E  S  G  G  G  S  V  Q  T  G  G  S  L  R  L  -

TCCTGTGCAGTCTCTGGATTCTCCTTTAGTACCAGTTGTATGGCCTGGTTCCGCCAGGCT
 61  ---------+---------+---------+---------+---------+---------+  120
     AGGACACGTCAGAGACCTAAGAGGAAATCATGGTCAACATACCGGACCAAGGCGGTCCGA

S  C  A  V  S  G  F  S  F  S  T  S  C  M  A  W  F  R  Q  A  -

TCAGGAAAGCAGCGTGAGGGGGTCGCAGCCATTAATAGTGGCGGTGGTAGGACATACTAC
121  ---------+---------+---------+---------+---------+---------+  180
     AGTCCTTTCGTCGCACTCCCCCAGCGTCGGTAATTATCACCGCCACCATCCTGTATGATG

S  G  K  Q  R  E  G  V  A  A  I  N  S  G  G  G  R  T  Y  Y  -

AACACATATGTCGCCGAGTCCGTGAAGGGCCGATTCGCCATCTCCCAAGACAACGCCAAG
181  ---------+---------+---------+---------+---------+---------+  240
     TTGTGTATACAGCGGCTCAGGCACTTCCCGGCTAAGCGGTAGAGGGTTCTGTTGCGGTTC

N  T  Y  V  A  E  S  V  K  G  R  F  A  I  S  Q  D  N  A  K  -

ACCACGGTATATCTTGATATGAACAACCTAACCCCTGAAGACACGGCTACGTATTACTGT
241  ---------+---------+---------+---------+---------+---------+  300
     TGGTGCCATATAGAACTATACTTGTTGGATTGGGGACTTCTGTGCCGATGCATAATGACA

T  T  V  Y  L  D  M  N  N  L  T  P  E  D  T  A  T  Y  Y  C  -

GCGGCGGTCCCAGCCCACTTGGGACCTGGCGCCATTCTTGATTTGAAAAAGTATAAGTAC
301  ---------+---------+---------+---------+---------+---------+  360
     CGCCGCCAGGGTCGGGTGAACCCTGGACCGCGGTAAGAACTAAACTTTTTCATATTCATG

A  A  V  P  A  H  L  G  P  G  A  I  L  D  L  K  K  Y  K  Y  -

BstEII
     TGGGGCCAGGGGACCCAGGTCACCGTCTCCTCACTAGCTAGTTACCCGTACGACGTTCCG
361  ---------+---------+---------+---------+---------+---------+  420
     ACCCCGGTCCCCTGGGTCCAGTGGCAGAGGAGTGATCGATCAATGGGCATGCTGCAAGGC

W  G  Q  G  T  Q  V  T  V  S  S  L  A  S  Y  P  Y  D  V  P  -

EcoRI
     GACTACGGTTCTTAATAGAATTC
421  ---------+---------+---  443
     CTGATGCCAAGAATTATCTTAAG

```
                    XhoI
    CAGGTGAAACTGCTCGAGTCTGGGGGAGGCTCGGTGCAGGCTGGGGGGTCTCTGACACTC
1   ------------+---------+---------+---------+---------+---------+ 60
    GTCCACTTTGACGAGCTCAGACCCCCTCCGAGCCACGTCCGACCCCCCAGAGACTGTGAG

Q  V  K  L  L  E  S  G  G  G  S  V  Q  A  G  G  S  L  T  L   -

StyI
                              NcoI
    TCTTGTGTATACACCAACGATACTGGGACCATGGGATGGTTTCGCCAGGCTCCAGGGAAA
61  ------------+---------+---------+---------+---------+---------+ 120
    AGAACACATATGTGGTTGCTATGACCCTGGTACCCTACCAAAGCGGTCCGAGGTCCCTTT

S  C  V  Y  T  N  D  T  G  T  M  G  W  F  R  Q  A  P  G  K   -

GAGTGCGAAAGGGTCGCGCATATTACGCCTGATGGTATGACCTTCATTGATGAACCCGTG
121 ------------+---------+---------+---------+---------+---------+ 180
    CTCACGCTTTCCCAGCGCGTATAATGCGGACTACCATACTGGAAGTAACTACTTGGGCAC

E  C  E  R  V  A  H  I  T  P  D  G  M  T  F  I  D  E  P  V   -

AAGGGGCGATTCACGATCTCCCGAGACAACGCCCAGAAAACGTTGTCTTTGCGAATGAAT
181 ------------+---------+---------+---------+---------+---------+ 240
    TTCCCCGCTAAGTGCTAGAGGGCTCTGTTGCGGGTCTTTTGCAACAGAAACGCTTACTTA

K  G  R  F  T  I  S  R  D  N  A  Q  K  T  L  S  L  R  M  N   -

EagI
    AGTCTGAGGCCTGAGGACACGGCCGTGTATTACTGTGCGGCAGATTGGAAATACTGGACT
241 ------------+---------+---------+---------+---------+---------+ 300
    TCAGACTCCGGACTCCTGTGCCGGCACATAATGACACGCCGTCTAACCTTTATGACCTGA

S  L  R  P  E  D  T  A  V  Y  Y  C  A  A  D  W  K  Y  W  T   -

BstEII
    TGTGGTGCCCAGACTGGAGGATACTTCGGACAGTGGGGTCAGGGGGCCCAGGTCACCGTC
301 ------------+---------+---------+---------+---------+---------+ 360
    ACACCACGGGTCTGACCTCCTATGAAGCCTGTCACCCCAGTCCCCCGGGTCCAGTGGCAG

C  G  A  Q  T  G  G  Y  F  G  Q  W  G  Q  G  A  Q  V  T  V   -

EcoRI
    TCCTCACTAGCTAGTTACCCGTACGACGTTCCGGACTACGGTTCTTAATAGAATTC
361 ------------+---------+---------+---------+---------+------ 416
    AGGAGTGATCGATCAATGGGCATGCTGCAAGGCCTGATGCCAAGAATTATCTTAAG

```
                    XhoI
     CAGGTGAAACTGCTCGAGTCTGGGGGAGGGTCGGTGCAGGCTGGAGGGTCTCTGAGACTC
  1  ---------+---------+---------+---------+---------+---------+  60
     GTCCACTTTGACGAGCTCAGACCCCCTCCCAGCCACGTCCGACCTCCCAGAGACTCTGAG

Q  V  K  L  L  E  S  G  G  G  S  V  Q  A  G  G  S  L  R  L   -

TCCTGTAATGTCTCTGGCTCTCCCAGTAGTACTTATTGCCTGGGCTGGTTCCGCCAGGCT
 61  ---------+---------+---------+---------+---------+---------+  120
     AGGACATTACAGAGACCGAGAGGGTCATCATGAATAACGGACCCGACCAAGGCGGTCCGA

S  C  N  V  S  G  S  P  S  S  T  Y  C  L  G  W  F  R  Q  A   -

CCAGGGAAGGAGCGTGAGGGGGTCACAGCGATTAACACTGATGGCAGTGTCATATACGCA
121  ---------+---------+---------+---------+---------+---------+  180
     GGTCCCTTCCTCGCACTCCCCCAGTGTCGCTAATTGTGACTACCGTCACAGTATATGCGT

P  G  K  E  R  E  G  V  T  A  I  N  T  D  G  S  V  I  Y  A   -

GCCGACTCCGTGAAGGGCCGATTCACCATCTCCCAAGACACCGCCAAGAAAACGGTATAT
181  ---------+---------+---------+---------+---------+---------+  240
     CGGCTGAGGCACTTCCCGGCTAAGTGGTAGAGGGTTCTGTGGCGGTTCTTTTGCCATATA

A  D  S  V  K  G  R  F  T  I  S  Q  D  T  A  K  K  T  V  Y   -

CTCCAGATGAACAACCTGCAACCTGAGGATACGGCCACCTATTACTGCGCGGCAAGACTG
241  ---------+---------+---------+---------+---------+---------+  300
     GAGGTCTACTTGTTGGACGTTGGACTCCTATGCCGGTGGATAATGACGCGCCGTTCTGAC

L  Q  M  N  N  L  Q  P  E  D  T  A  T  Y  Y  C  A  A  R  L   -

ACGGAGATGGGGGCTTGTGATGCGAGATGGGCGACCTTAGCGACAAGGACGTTTGCGTAT
301  ---------+---------+---------+---------+---------+---------+  360
     TGCCTCTACCCCCGAACACTACGCTCTACCCGCTGGAATCGCTGTTCCTGCAAACGCATA

T  E  M  G  A  C  D  A  R  W  A  T  L  A  T  R  T  F  A  Y   -

BstEII
     AACTACTGGGGCCGGGGGACCCAGGTCACCGTCTCCTCACTAGCTAGTTACCCGTACGAC
361  ---------+---------+---------+---------+---------+---------+  420
     TTGATGACCCCGGCCCCCTGGGTCCAGTGGCAGAGGAGTGATCGATCAATGGGCATGCTG

N  Y  W  G  R  G  T  Q  V  T  V  S  S  L  A  S  Y  P  Y  D   -

EcoRI
     GTTCCGGACTACGGTTCTTAATAGAATTC
421  ---------+---------+--------- 449
     CAAGGCCTGATGCCAAGAATTATCTTAAG

```
         (EcoRI) EacI                XhoI              BstEII
        AATTTAGCGGCCGCCCAGGTGAAACTGCTCGAGTAAGTGACTAAGGTCACCGTCTCCTCA
     1  ---------+---------+---------+---------+---------+---------+ 60
        TTAAATCGCCGGCGGGTCCACTTTGACGAGCTCATTCACTGATTCCAGTGGCAGAGGAGT
              A  Q  V  K  L  L  E              V  T  V  S  S

EcoRI         HindIII
        GAACAAAAACTCATCTCAGAAGAGGATCTGAATTAATGAGAATTCATCAAACGGTGATA
    61  ---------+---------+---------+---------+---------+---------+ 120
        CTTGTTTTTGAGTAGAGTCTTCTCCTAGACTTAATTACTCTTAAGTAGTTTGCCACTATT
         E  Q  K  L  I  S  E  E  D  L  N  *  *

121  --- 123
        CGA
```

FIG. 6

```
         (EcoRI) NruI               XhoI              BstEII
        AATTTAGTCGCGACAGGTGAAACTGCTCGAGTAAGTGACTAAGGTCACCGTCTCCTCAGA
     1  ---------+---------+---------+---------+---------+---------+ 60
           ATCAGCGCTGTCCACTTTGACGAGCTCATTCACTGATTCCAGTGGCAGAGGAGTCT
             R  Q  V  K  L  L             V  T  V  S  S  E

EcoRI   AflII    HindIII
        ACAAAAACTCATCTCAGAAGAGGATCTGAATTAATGAGAATTCATCTTAAGGTGATA
    61  ---------+---------+---------+---------+---------+---------+ 120
        TGTTTTTGAGTAGAGTCTTCTCCTAGACTTAATTACTCTTAAGTAGAATTCCACTATTCG
         Q  K  L  I  S  E  E  D  L  N  *  *

SEQUENCE LISTING (1) GENERAL INFORMATION:

(iii) NUMBER OF SEQUENCES: 71

(2) INFORMATION FOR SEQ ID NO: 1:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 1:

Ala Pro Glu Leu Leu
1               5

(2) INFORMATION FOR SEQ ID NO: 2:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 2:

Ala Pro Glu Leu Pro
1               5

(2) INFORMATION FOR SEQ ID NO: 3:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 3:

CGCCATCAAG GTACCAGTTG A                                                  21

(2) INFORMATION FOR SEQ ID NO: 4:

(i) SEQUENCE CHARACTERISTICS:
       (A) LENGTH: 26 amino acids
       (B) TYPE: amino acid
       (C) STRANDEDNESS: single
       (D) TOPOLOGY: linear (ii) MOLECULE TYPE: protein (vii) IMMEDIATE SOURCE:
       (B) CLONE: human heavy chain framework (subgroup III)

(xi) SEQUENCE DESCRIPTION: SEQ ID NO: 4:

Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

(2) INFORMATION FOR SEQ ID NO: 5:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" framework A (xi) SEQUENCE DESCRIPTION: SEQ ID NO: 5:

Gly Gly Ser Val Gln Gly Gly Gly Ser Leu Arg Leu Ser Cys Ala Ile
1               5                   10                  15

Ser Gly (2) INFORMATION FOR SEQ ID NO: 6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" framework B (xi) SEQUENCE DESCRIPTION: SEQ ID NO: 6:

Gly Gly Ser Val Gln Ala Gly Gly Ser Leu Arg Leu Ser Cys Ala Ser
1               5                   10                  15

Ser Ser (2) INFORMATION FOR SEQ ID NO: 7:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin"
            framework - short hinge - CH2 fragment (xi) SEQUENCE DESCRIPTION: SEQ ID NO: 7:

Trp Gly Gln Gly Thr Gln Val Thr Val Ser Ser Gly Thr Asn Glu Val
1               5                   10                  15

Cys Lys Cys Pro Lys Cys Pro Ala Pro Glu Leu Pro Gly Gly Pro Ser
            20                  25                  30

Val Phe Val Phe Pro
        35

(2) INFORMATION FOR SEQ ID NO: 8:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin"
            framework - long hinge - CH2 fragment (xi) SEQUENCE DESCRIPTION: SEQ ID NO: 8:

Trp Gly Gln Gly Thr Gln Val Thr Val Ser Ser Glu Pro Lys Ile Pro
1               5                   10                  15

Gln Pro Gln Pro Lys Pro Gln Pro Gln Pro Gln Pro Gln Pro Lys Pro
            20                  25                  30

Gln Pro Lys Pro Glu Pro Glu Cys Thr Cys Pro Lys Cys Pro Ala Pro
        35                  40                  45

Glu Leu Leu Gly Gly Pro Ser Val Phe Ile Phe Pro
    50                  55                  60

(2) INFORMATION FOR SEQ ID NO: 9:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: human gamma-3 CH1 - hinge - CH2 fragment (xi) SEQUENCE DESCRIPTION: SEQ ID NO: 9:

Lys Val Asp Lys Arg Val Glu Leu Lys Thr Pro Leu Gly Asp Thr Thr
1               5                   10                  15

His Thr Cys Pro Arg Cys Pro Glu Pro Lys Cys Ser Asp Thr Pro Pro
            20                  25                  30

Pro Cys Pro Arg Cys Pro Glu Pro Lys Ser Cys Asp Thr Pro Pro Pro
        35                  40                  45

Cys Pro Arg Cys Pro Ala Pro Glu Leu Leu Gly Gly Pro Ser Val Phe
    50                  55                  60

Leu Phe Pro
65

(2) INFORMATION FOR SEQ ID NO: 10:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: human gamma-1 CH1 - hinge - CH2 fragment (xi) SEQUENCE DESCRIPTION: SEQ ID NO: 10:

Lys Val Asp Lys Lys Ala Glu Pro Lys Ser Cys Asp Lys Thr His Thr
1               5                   10                  15

Cys Pro Pro Cys Pro Ala Pro Glu Leu Leu Gly Gly Pro Ser Val Phe
            20                  25                  30

Leu Phe Pro
        35

(2) INFORMATION FOR SEQ ID NO: 11:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (vii) IMMEDIATE SOURCE:
   (B) CLONE: human gamma-2 CH1 - hinge - CH2 fragment (xi) SEQUENCE DESCRIPTION: SEQ ID NO: 11:

```
Lys Val Lys Val Thr Val Glu Arg Lys Cys Cys Val Glu Cys Pro Pro
1               5                   10                  15

Cys Pro Ala Pro Pro Val Ala Gly Pro Ser Val Phe Leu Phe Pro
            20                  25                  30
```

(2) INFORMATION FOR SEQ ID NO: 12:

(i) SEQUENCE CHARACTERISTICS:
      (A) LENGTH: 32 amino acids
      (B) TYPE: amino acid
      (C) STRANDEDNESS: single
      (D) TOPOLOGY: linear (ii) MOLECULE TYPE: protein (vii) IMMEDIATE SOURCE:
      (B) CLONE: human gamma-4 CH1 - hinge - CH2 fragment (xi) SEQUENCE DESCRIPTION: SEQ ID NO: 12:

```
Lys Val Asp Lys Arg Val Glu Ser Lys Tyr Gly Pro Pro Cys Pro Ser
1               5                   10                  15

Cys Pro Ala Pro Glu Phe Leu Gly Gly Pro Ser Val Phe Leu Phe Pro
            20                  25                  30
```

(2) INFORMATION FOR SEQ ID NO: 13:

(i) SEQUENCE CHARACTERISTICS:
      (A) LENGTH: 121 amino acids
      (B) TYPE: amino acid
      (C) STRANDEDNESS: single
      (D) TOPOLOGY: linear (ii) MOLECULE TYPE: protein (vii) IMMEDIATE SOURCE:
      (B) CLONE: mouse heavy chain V-region (xi) SEQUENCE DESCRIPTION: SEQ ID NO: 13:

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Ala Asn Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Tyr Tyr Gly Ser Ser Tyr Phe Asp Val Trp Gly
            100                 105                 110

Ala Gly Thr Thr Val Thr Val Ser Ser
        115                 120
```

(2) INFORMATION FOR SEQ ID NO: 14:

(i) SEQUENCE CHARACTERISTICS:
    (A) LENGTH: 131 amino acids
    (B) TYPE: amino acid
    (C) STRANDEDNESS: single
    (D) TOPOLOGY: linear (ii) MOLECULE TYPE: protein (vii) IMMEDIATE SOURCE:
     (B) CLONE: human heavy chain V-region (xi) SEQUENCE DESCRIPTION: SEQ ID NO: 14:

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Xaa Ile Ser Xaa Lys Thr Asp Gly Gly Xaa Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Xaa Xaa Xaa Xaa Xaa Xaa Xaa Xaa Xaa Xaa Xaa Tyr
            100                 105                 110

Tyr Tyr Tyr His Xaa Phe Asp Tyr Trp Gly Gln Gly Thr Leu Val Thr
            115                 120                 125

Val Ser Ser
    130
```

(2) INFORMATION FOR SEQ ID NO: 15:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
         (B) CLONE: camel "heavy chain immunoglobulin" V-region (1)

(xi) SEQUENCE DESCRIPTION: SEQ ID NO: 15:

```
Gly Gly Ser Val Gln Ala Gly Gly Ser Leu Arg Leu Ser Cys Ala Ala
1               5                   10                  15

Ser Gly Tyr Ser Asn Cys Pro Leu Thr Trp Ser Trp Tyr Arg Gln Phe
            20                  25                  30

Pro Gly Thr Glu Arg Glu Phe Val Ser Ser Met Asp Pro Asp Gly Asn
        35                  40                  45

Thr Lys Tyr Thr Tyr Ser Val Lys Gly Arg Phe Thr Met Ser Arg Gly
    50                  55                  60

Ser Thr Glu Tyr Thr Val Phe Leu Gln Met Asp Asn Leu Lys Pro Glu
65                  70                  75                  80

Asp Thr Ala Met Tyr Tyr Cys Lys Thr Ala Leu Gln Pro Gly Gly Tyr
                85                  90                  95

Cys Gly Tyr Gly Xaa Cys Leu Trp Gly Gln Gly Thr Gln Val Thr Val
            100                 105                 110

Ser Ser
```

```
(2) INFORMATION FOR SEQ ID NO: 16:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (2)

(xi) SEQUENCE DESCRIPTION: SEQ ID NO: 16:

Asp Val Gln Leu Val Ala Ser Gly Gly Gly Ser Val Gln Ala Gly Gly
1               5                   10                  15

Ser Leu Arg Leu Ser Cys Thr Ala Ser Gly Asp Ser Phe Ser Arg Phe
            20                  25                  30

Ala Met Ser Trp Phe Arg Gln Ala Pro Gly Lys Glu Cys Glu Leu Val
        35                  40                  45

Ser Ser Ile Gln Ser Asn Gly Arg Thr Thr Glu Ala Asp Ser Val Gln
    50                  55                  60

Gly Arg Phe Thr Ile Ser Arg Asp Asn Ser Arg Asn Thr Val Tyr Leu
65                  70                  75                  80

Gln Met Asn Ser Leu Lys Pro Glu Asp Thr Ala Val Tyr Tyr Cys Gly
                85                  90                  95

Ala Val Ser Leu Met Asp Arg Ile Ser Gln His Gly Cys Arg Gly Gln
            100                 105                 110

Gly Thr Gln Val Thr Val Ser Leu
        115                 120

(2) INFORMATION FOR SEQ ID NO: 17:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (3)

(xi) SEQUENCE DESCRIPTION: SEQ ID NO: 17:

Gly Gly Ser Val Gln Thr Gly Gly Ser Leu Arg Leu Ser Cys Ala Val
1               5                   10                  15

Ser Gly Phe Ser Phe Ser Thr Ser Cys Met Ala Trp Phe Arg Gln Ala
            20                  25                  30

Ser Gly Lys Gln Arg Glu Gly Val Ala Ala Ile Asn Ser Gly Gly Gly
        35                  40                  45

Arg Thr Tyr Tyr Asn Thr Tyr Val Ala Glu Ser Val Lys Gly Arg Phe
    50                  55                  60

Ala Ile Ser Gln Asp Asn Ala Lys Thr Thr Val Tyr Leu Asp Met Asn
65                  70                  75                  80

Asn Leu Thr Pro Glu Asp Thr Ala Thr Tyr Tyr Cys Ala Ala Val Pro
                85                  90                  95

Ala His Leu Gly Pro Gly Ala Ile Leu Asp Leu Lys Lys Tyr Lys Tyr
            100                 105                 110

Trp Gly Gln Gly Thr Gln Val Thr Val Ser Ser
        115                 120
```

(2) INFORMATION FOR SEQ ID NO: 18:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (7)

(xi) SEQUENCE DESCRIPTION: SEQ ID NO: 18:

```
Gly Gly Ser Val Gln Gly Gly Ser Leu Arg Leu Ser Cys Ala Ile
1               5                   10                  15

Ser Gly Tyr Thr Tyr Gly Ser Phe Cys Met Gly Trp Phe Arg Glu Gly
            20                  25                  30

Pro Gly Lys Glu Arg Glu Gly Ile Ala Thr Ile Leu Asn Gly Gly Thr
            35                  40                  45

Asn Thr Tyr Tyr Ala Asp Ser Val Lys Gly Arg Phe Thr Ile Ser Gln
50                  55                  60

Asp Ser Thr Leu Lys Thr Met Tyr Leu Leu Met Asn Asn Leu Lys Pro
65                  70                  75                  80

Glu Asp Thr Gly Thr Tyr Tyr Cys Ala Ala Glu Leu Ser Gly Ser
                85                  90                  95

Cys Glu Leu Pro Leu Leu Phe Asp Tyr Trp Gly Gln Gly Thr Gln Val
            100                 105                 110

Thr Val Ser Ser
        115
```

(2) INFORMATION FOR SEQ ID NO: 19:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (9)

(xi) SEQUENCE DESCRIPTION: SEQ ID NO: 19:

```
Gly Gly Ser Val Gln Ala Gly Gly Ser Leu Thr Leu Ser Cys Val Tyr
1               5                   10                  15

Thr Asn Asp Thr Gly Thr Met Gly Trp Phe Arg Gln Ala Pro Gly Lys
            20                  25                  30

Glu Cys Glu Arg Val Ala His Ile Thr Pro Asp Gly Met Thr Phe Ile
            35                  40                  45

Asp Glu Pro Val Lys Gly Arg Phe Thr Ile Ser Arg Asp Asn Ala Gln
50                  55                  60

Lys Thr Leu Ser Leu Arg Met Asn Ser Leu Arg Pro Glu Asp Thr Ala
65                  70                  75                  80

Val Tyr Tyr Cys Ala Ala Asp Trp Lys Tyr Trp Thr Cys Gly Ala Gln
                85                  90                  95

Thr Gly Gly Tyr Phe Gly Gln Trp Gly Gln Gly Ala Gln Val Thr Val
            100                 105                 110

Ser Ser
```

(2) INFORMATION FOR SEQ ID NO: 20:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (11)

(xi) SEQUENCE DESCRIPTION: SEQ ID NO: 20:

```
Gly Gly Ser Val Gln Ala Gly Gly Ser Leu Arg Leu Ser Cys Asn Val
1               5                   10                  15

Ser Gly Ser Pro Ser Ser Thr Tyr Cys Leu Gly Trp Phe Arg Gln Ala
            20                  25                  30

Pro Gly Arg Glu Arg Glu Gly Val Thr Ala Ile Asn Thr Asp Gly Ser
        35                  40                  45

Ile Ile Tyr Ala Ala Asp Ser Val Lys Gly Arg Phe Thr Ile Ser Gln
50                  55                  60

Asp Thr Ala Lys Glu Thr Val His Leu Gln Met Asn Asn Leu Gln Pro
65                  70                  75                  80

Glu Asp Thr Ala Thr Tyr Tyr Cys Ala Ala Arg Leu Thr Glu Met Gly
                85                  90                  95

Ala Cys Asp Ala Arg Trp Ala Thr Leu Ala Thr Arg Thr Phe Ala Tyr
            100                 105                 110

Asn Tyr Trp Gly Gln Gly Thr Gln Val Thr Val Ser Ser
        115                 120                 125
```

(2) INFORMATION FOR SEQ ID NO: 21:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (13)

(xi) SEQUENCE DESCRIPTION: SEQ ID NO: 21:

```
Gly Gly Ser Val Glu Ala Gly Gly Ser Leu Arg Leu Ser Cys Thr Ala
1               5                   10                  15

Ser Gly Tyr Val Ser Ser Met Ala Trp Phe Arg Gln Val Pro Gly Gln
            20                  25                  30

Glu Arg Glu Gly Val Ala Phe Val Gln Thr Ala Asp Asn Ser Ala Leu
        35                  40                  45

Tyr Gly Asp Ser Val Lys Gly Arg Phe Thr Ile Ser His Asp Asn Ala
    50                  55                  60

Lys Asn Thr Leu Tyr Leu Gln Met Arg Asn Leu Gln Pro Asp Asp Thr
65                  70                  75                  80

Gly Val Tyr Tyr Cys Ala Ala Gln Lys Lys Asp Arg Thr Arg Trp Ala
            85                  90                  95

Glu Pro Arg Glu Trp Asn Asn Trp Gly Gln Gly Thr Gln Val Thr Ala
        100                 105                 110

Ser Ser
```

(2) INFORMATION FOR SEQ ID NO: 22:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (16)

(xi) SEQUENCE DESCRIPTION: SEQ ID NO: 22:

```
Gly Gly Ser Ala Gln Ala Gly Gly Ser Leu Arg Leu Ser Cys Ala Ala
  1               5                  10                  15

His Gly Ile Pro Leu Asn Gly Tyr Tyr Ile Ala Trp Phe Arg Gln Ala
             20                  25                  30

Pro Gly Lys Gly Arg Glu Gly Val Ala Thr Ile Asn Gly Gly Arg Asp
         35                  40                  45

Val Thr Tyr Tyr Ala Asp Ser Val Thr Gly Arg Phe Thr Ile Ser Arg
 50                  55                  60

Asp Ser Pro Lys Asn Thr Val Tyr Leu Gln Met Asn Ser Leu Lys Pro
 65                  70                  75                  80

Glu Asp Thr Ala Ile Tyr Phe Cys Ala Ala Gly Ser Arg Phe Ser Ser
                 85                  90                  95

Pro Val Gly Ser Thr Ser Arg Leu Glu Ser Ser Asp Tyr Asn Tyr Trp
            100                 105                 110

Gly Gln Gly Ile Gln Val Thr Ala Ser Ser
            115                 120
```

(2) INFORMATION FOR SEQ ID NO: 23:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (17)

(xi) SEQUENCE DESCRIPTION: SEQ ID NO: 23:

```
Gly Gly Ser Val Gln Pro Gly Gly Ser Leu Thr Leu Ser Cys Thr Val
  1               5                  10                  15

Ser Gly Ala Thr Tyr Ser Asp Tyr Ser Ile Gly Trp Ile Arg Gln Ala
             20                  25                  30

Pro Gly Lys Asp Arg Glu Val Val Ala Ala Asn Thr Gly Ala Thr
         35                  40                  45

Ser Lys Phe Tyr Val Asp Phe Val Lys Gly Arg Phe Thr Ile Ser Gln
 50                  55                  60

Asp Asn Ala Lys Asn Thr Val Tyr Leu Gln Met Ser Phe Leu Lys Pro
 65                  70                  75                  80

Glu Asp Thr Ala Ile Tyr Tyr Cys Ala Ala Ala Asp Pro Ser Ile Tyr
                 85                  90                  95

Tyr Ser Ile Leu Xaa Ile Glu Tyr Lys Tyr Trp Gly Gln Gly Thr Gln
            100                 105                 110

Val Thr Val Ser Ser
```

(2) INFORMATION FOR SEQ ID NO: 24:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (18)

(xi) SEQUENCE DESCRIPTION: SEQ ID NO: 24:

```
Gly Gly Ser Val Gln Ala Gly Gly Ser Leu Arg Leu Ser Cys Thr Gly
1               5                   10                  15

Ser Gly Phe Pro Tyr Ser Thr Phe Cys Leu Gly Trp Phe Arg Gln Ala
            20                  25                  30

Pro Gly Lys Glu Arg Glu Gly Val Ala Gly Ile Asn Ser Ala Gly Gly
        35                  40                  45

Asn Thr Tyr Tyr Ala Asp Ala Val Lys Gly Arg Phe Thr Ile Ser Gln
50                  55                  60

Gly Asn Ala Lys Asn Thr Val Phe Leu Gln Met Asp Asn Leu Lys Pro
65                  70                  75                  80

Glu Asp Thr Ala Ile Tyr Tyr Cys Ala Ala Asp Ser Pro Cys Tyr Met
                85                  90                  95

Pro Thr Met Pro Ala Pro Pro Ile Arg Asp Ser Phe Gly Trp Asp Asp
            100                 105                 110

Phe Gly Gln Gly Thr Gln Val Thr Val Ser Ser
        115                 120
```

(2) INFORMATION FOR SEQ ID NO: 25:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (19)

(xi) SEQUENCE DESCRIPTION: SEQ ID NO: 25:

```
Gly Gly Ser Val Gln Ala Gly Gly Ser Leu Arg Leu Ser Cys Ala Ala
1               5                   10                  15

Ser Asp Tyr Thr Ile Thr Asp Tyr Cys Met Ala Trp Phe Arg Gln Ala
            20                  25                  30

Pro Gly Lys Glu Arg Glu Leu Val Ala Ala Ile Gln Val Val Arg Ser
        35                  40                  45

Asp Thr Arg Leu Thr Asp Tyr Ala Asp Ser Val Lys Gly Arg Phe Thr
50                  55                  60

Ile Ser Gln Gly Asn Thr Lys Asn Thr Val Asn Leu Gln Met Asn Ser
65                  70                  75                  80

Leu Thr Pro Glu Asp Thr Ala Ile Tyr Ser Cys Ala Ala Thr Ser Ser
                85                  90                  95

Phe Tyr Trp Tyr Cys Thr Thr Ala Pro Tyr Asn Val Trp Gly Gln Gly
            100                 105                 110
```

Thr Gln Val Thr Val Ser Ser
      115

(2) INFORMATION FOR SEQ ID NO: 26:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (20)

(xi) SEQUENCE DESCRIPTION: SEQ ID NO: 26:

Gly Gly Ser Val Gln Val Gly Gly Ser Leu Arg Leu Ser Cys Val Ala
1               5                   10                  15

Ser Thr His Thr Asp Ser Ser Thr Cys Ile Gly Trp Phe Arg Gln Ala
            20                  25                  30

Pro Gly Lys Glu Arg Glu Gly Val Ala Ser Ile Tyr Phe Gly Asp Gly
            35                  40                  45

Gly Thr Asn Tyr Arg Asp Ser Val Lys Gly Arg Phe Thr Ile Ser Gln
        50                  55                  60

Leu Asn Ala Gln Asn Thr Val Tyr Leu Gln Met Asn Ser Leu Lys Pro
65                  70                  75                  80

Glu Asp Ser Ala Met Tyr Tyr Cys Ala Ile Thr Glu Ile Glu Trp Tyr
                85                  90                  95

Gly Cys Asn Leu Arg Thr Thr Phe Thr Arg Trp Gly Gln Gly Thr Gln
            100                 105                 110

Val Thr Val Ser Ser
        115

(2) INFORMATION FOR SEQ ID NO: 27:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (21)

(xi) SEQUENCE DESCRIPTION: SEQ ID NO: 27:

Gly Gly Ser Val Gln Val Gly Gly Ser Leu Lys Leu Ser Cys Lys Ile
1               5                   10                  15

Ser Gly Gly Thr Pro Asp Arg Val Pro Lys Ser Leu Ala Trp Phe Arg
            20                  25                  30

Gln Ala Pro Glu Lys Glu Arg Glu Gly Ile Ala Val Leu Ser Thr Lys
            35                  40                  45

Asp Gly Lys Thr Phe Tyr Ala Asp Ser Val Lys Gly Arg Phe Thr Ile
        50                  55                  60

Phe Leu Asp Asn Asp Lys Thr Thr Phe Ser Leu Gln Leu Asp Arg Leu
65                  70                  75                  80

Asn Pro Glu Asp Thr Ala Asp Tyr Tyr Cys Ala Ala Asn Gln Leu Ala
                85                  90                  95

Gly Gly Trp Tyr Leu Asp Pro Asn Tyr Trp Leu Ser Val Gly Ala Tyr
            100                 105                 110

Ala Ile Trp Gly Gln Gly Thr His Val Thr Val Ser Ser
          115                 120                 125

(2) INFORMATION FOR SEQ ID NO: 28:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (vii) IMMEDIATE SOURCE:
          (B) CLONE: camel "heavy chain immunoglobulin" V-region (24)

(xi) SEQUENCE DESCRIPTION: SEQ ID NO: 28:

Gly Gly Ser Val Gln Ala Gly Gly Ser Leu Arg Leu Ser Cys Asn Val
1               5                   10                  15

Ser Gly Ser Pro Ser Ser Thr Tyr Cys Leu Gly Trp Phe Arg Gln Ala
            20                  25                  30

Pro Gly Lys Glu Arg Glu Gly Val Thr Ala Ile Asn Thr Asp Gly Ser
            35                  40                  45

Val Ile Tyr Ala Ala Asp Ser Val Lys Gly Arg Phe Thr Ile Ser Gln
50                  55                  60

Asp Thr Ala Lys Lys Thr Val Tyr Leu Gln Met Asn Asn Leu Gln Pro
65                  70                  75                  80

Glu Asp Thr Ala Thr Tyr Tyr Cys Ala Ala Arg Leu Thr Glu Met Gly
                85                  90                  95

Ala Cys Asp Ala Arg Trp Ala Thr Leu Ala Thr Arg Thr Phe Ala Tyr
            100                 105                 110

Asn Tyr Trp Gly Arg Gly Thr Gln Val Thr Val Ser Ser
            115                 120                 125

(2) INFORMATION FOR SEQ ID NO: 29:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: protein (vii) IMMEDIATE SOURCE:
          (B) CLONE: camel "heavy chain immunoglobulin" V-region (25)

(xi) SEQUENCE DESCRIPTION: SEQ ID NO: 29:

Gly Gly Ser Val Gln Thr Gly Gly Ser Leu Arg Leu Ser Cys Glu Ile
1               5                   10                  15

Ser Gly Leu Thr Phe Asp Asp Ser Asp Val Gly Trp Tyr Arg Gln Ala
            20                  25                  30

Pro Gly Asp Glu Cys Lys Leu Val Ser Gly Ile Leu Ser Asp Gly Thr
            35                  40                  45

Pro Tyr Thr Lys Ser Gly Asp Tyr Ala Glu Ser Val Arg Gly Arg Val
50                  55                  60

Thr Ile Ser Arg Asp Asn Ala Lys Asn Met Ile Tyr Leu Gln Met Asn
65                  70                  75                  80

Asp Leu Lys Pro Glu Asp Thr Ala Met Tyr Tyr Cys Ala Val Asp Gly
                85                  90                  95

Trp Thr Arg Lys Glu Gly Gly Ile Gly Leu Pro Trp Ser Val Gln Cys

```
                    100                 105                 110
Glu Asp Gly Tyr Asn Tyr Trp Gly Gln Gly Thr Gln Val Thr Val Ser
            115                 120                 125
Ser
```

(2) INFORMATION FOR SEQ ID NO: 30:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (27)

(xi) SEQUENCE DESCRIPTION: SEQ ID NO: 30:

```
Gly Gly Ser Val Gln Ala Gly Gly Ser Leu Arg Leu Ser Cys Ala Ser
1               5                   10                  15
Ser Ser Lys Tyr Met Pro Cys Thr Tyr Asp Met Thr Trp Tyr Arg Gln
            20                  25                  30
Ala Pro Gly Lys Glu Arg Glu Phe Val Ser Ser Ile Asn Ile Asp Gly
        35                  40                  45
Lys Thr Thr Tyr Ala Asp Ser Val Lys Gly Arg Phe Thr Ile Ser Gln
    50                  55                  60
Asp Ser Ala Lys Asn Thr Val Tyr Leu Gln Met Asn Ser Leu Lys Pro
65                  70                  75                  80
Glu Asp Thr Ala Met Tyr Tyr Cys Lys Ile Asp Ser Tyr Pro Cys His
                85                  90                  95
Leu Leu Asp Val Trp Gly Gln Gly Thr Gln Val Thr Val Ser Ser
                100                 105                 110
```

(2) INFORMATION FOR SEQ ID NO: 31:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" V-region (29)

(xi) SEQUENCE DESCRIPTION: SEQ ID NO: 31:

```
Gly Gly Ser Val Gln Ala Gly Gly Ser Leu Arg Leu Ser Cys Val Ala
1               5                   10                  15
Ser Gly Phe Asn Phe Glu Thr Ser Arg Met Ala Trp Tyr Arg Gln Thr
            20                  25                  30
Pro Gly Asn Val Cys Glu Leu Val Ser Ser Ile Tyr Ser Asp Gly Lys
        35                  40                  45
Thr Tyr Tyr Val Asp Arg Met Lys Gly Arg Phe Thr Ile Ser Arg Glu
    50                  55                  60
Asn Ala Lys Asn Thr Leu Tyr Leu Gln Leu Ser Gly Leu Lys Pro Glu
65                  70                  75                  80
Asp Thr Ala Met Tyr Tyr Cys Ala Pro Val Glu Tyr Pro Ile Ala Asp
                85                  90                  95
Met Cys Ser Arg Tyr Gly Asp Pro Gly Thr Gln Val Thr Val Ser Ser
```

(2) INFORMATION FOR SEQ ID NO: 32:

(i) SEQUENCE CHARACTERISTICS:
        (A) LENGTH: 416 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: camel "heavy chain immunoglobulin" V-region
            followed by the FLAG sequence (pB03)

(ix) FEATURE:
        (A) NAME/KEY: CDS
        (B) LOCATION: 1..408

(xi) SEQUENCE DESCRIPTION: SEQ ID NO: 32:

```
CAG GTG AAA CTG CTC GAG TCT GGG GGA GGC TCG GTG CAG GCT GGG GGG        48
Gln Val Lys Leu Leu Glu Ser Gly Gly Gly Ser Val Gln Ala Gly Gly
 1               5                  10                  15

TCT CTG ACA CTC TCT TGT GTA TAC ACC AAC GAT ACT GGG ACC ATG GGA        96
Ser Leu Thr Leu Ser Cys Val Tyr Thr Asn Asp Thr Gly Thr Met Gly
             20                  25                  30

TGG TTT CGC CAG GCT CCA GGG AAA GAG TGC GAA AGG GTC GCG CAT ATT       144
Trp Phe Arg Gln Ala Pro Gly Lys Glu Cys Glu Arg Val Ala His Ile
         35                  40                  45

ACG CCT GAT GGT ATG ACC TTC ATT GAT GAA CCC GTG AAG GGG CGA TTC       192
Thr Pro Asp Gly Met Thr Phe Ile Asp Glu Pro Val Lys Gly Arg Phe
     50                  55                  60

ACG ATC TCC CGA GAC AAC GCC CAG AAA ACG TTG TCT TTG CGA ATG AAT       240
Thr Ile Ser Arg Asp Asn Ala Gln Lys Thr Leu Ser Leu Arg Met Asn
 65                  70                  75                  80

AGT CTG AGG CCT GAG GAC ACG GCC GTG TAT TAC TGT GCG GCA GAT TGG       288
Ser Leu Arg Pro Glu Asp Thr Ala Val Tyr Tyr Cys Ala Ala Asp Trp
                 85                  90                  95

AAA TAC TGG ACT TGT GGT GCC CAG ACT GGA GGA TAC TTC GGA CAG TGG       336
Lys Tyr Trp Thr Cys Gly Ala Gln Thr Gly Gly Tyr Phe Gly Gln Trp
            100                 105                 110

GGT CAG GGG GCC CAG GTC ACC GTC TCC TCA CTA GCT AGT TAC CCG TAC       384
Gly Gln Gly Ala Gln Val Thr Val Ser Ser Leu Ala Ser Tyr Pro Tyr
        115                 120                 125

GAC GTT CCG GAC TAC GGT TCT TAATAGAATT C                              416
Asp Val Pro Asp Tyr Gly Ser
    130                 135
```

(2) INFORMATION FOR SEQ ID NO: 33:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO: 33:

```
Gln Val Lys Leu Leu Glu Ser Gly Gly Gly Ser Val Gln Ala Gly Gly
 1               5                  10                  15

Ser Leu Thr Leu Ser Cys Val Tyr Thr Asn Asp Thr Gly Thr Met Gly
             20                  25                  30

Trp Phe Arg Gln Ala Pro Gly Lys Glu Cys Glu Arg Val Ala His Ile
         35                  40                  45
```

```
Thr Pro Asp Gly Met Thr Phe Ile Asp Glu Pro Val Lys Gly Arg Phe
 50                  55                  60

Thr Ile Ser Arg Asp Asn Ala Gln Lys Thr Leu Ser Leu Arg Met Asn
 65                  70                  75                  80

Ser Leu Arg Pro Glu Asp Thr Ala Val Tyr Tyr Cys Ala Ala Asp Trp
                 85                  90                  95

Lys Tyr Trp Thr Cys Gly Ala Gln Thr Gly Gly Tyr Phe Gly Gln Trp
                100                 105                 110

Gly Gln Gly Ala Gln Val Thr Val Ser Ser Leu Ala Ser Tyr Pro Tyr
                115                 120                 125

Asp Val Pro Asp Tyr Gly Ser
130                 135
```

(2) INFORMATION FOR SEQ ID NO: 34:

(i) SEQUENCE CHARACTERISTICS:
        (A) LENGTH: 443 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: camel "heavy chain immunoglobulin" V-region
            followed by the FLAG sequence (pB09)

(ix) FEATURE:
        (A) NAME/KEY: CDS
        (B) LOCATION: 1..435

(xi) SEQUENCE DESCRIPTION: SEQ ID NO: 34:

```
CAG GTG AAA CTG CTC GAG TCT GGA GGA GGC TCG GTG CAG ACT GGA GGA        48
Gln Val Lys Leu Leu Glu Ser Gly Gly Gly Ser Val Gln Thr Gly Gly
 1               5                  10                  15

TCT CTG AGA CTC TCC TGT GCA GTC TCT GGA TTC TCC TTT AGT ACC AGT        96
Ser Leu Arg Leu Ser Cys Ala Val Ser Gly Phe Ser Phe Ser Thr Ser
                 20                  25                  30

TGT ATG GCC TGG TTC CGC CAG GCT TCA GGA AAG CAG CGT GAG GGG GTC       144
Cys Met Ala Trp Phe Arg Gln Ala Ser Gly Lys Gln Arg Glu Gly Val
             35                  40                  45

GCA GCC ATT AAT AGT GGC GGT GGT AGG ACA TAC TAC AAC ACA TAT GTC       192
Ala Ala Ile Asn Ser Gly Gly Gly Arg Thr Tyr Tyr Asn Thr Tyr Val
         50                  55                  60

GCC GAG TCC GTG AAG GGC CGA TTC GCC ATC TCC CAA GAC AAC GCC AAG       240
Ala Glu Ser Val Lys Gly Arg Phe Ala Ile Ser Gln Asp Asn Ala Lys
 65                  70                  75                  80

ACC ACG GTA TAT CTT GAT ATG AAC AAC CTA ACC CCT GAA GAC ACG GCT       288
Thr Thr Val Tyr Leu Asp Met Asn Asn Leu Thr Pro Glu Asp Thr Ala
                 85                  90                  95

ACG TAT TAC TGT GCG GCG GTC CCA GCC CAC TTG GGA CCT GGC GCC ATT       336
Thr Tyr Tyr Cys Ala Ala Val Pro Ala His Leu Gly Pro Gly Ala Ile
             100                 105                 110

CTT GAT TTG AAA AAG TAT AAG TAC TGG GGC CAG GGG ACC CAG GTC ACC       384
Leu Asp Leu Lys Lys Tyr Lys Tyr Trp Gly Gln Gly Thr Gln Val Thr
         115                 120                 125

GTC TCC TCA CTA GCT AGT TAC CCG TAC GAC GTT CCG GAC TAC GGT TCT       432
Val Ser Ser Leu Ala Ser Tyr Pro Tyr Asp Val Pro Asp Tyr Gly Ser
130                 135                 140

TAATAGAATT C                                                         443
```

(2) INFORMATION FOR SEQ ID NO: 35:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO: 35:

```
Gln Val Lys Leu Leu Glu Ser Gly Gly Gly Ser Val Gln Thr Gly Gly
 1               5                  10                  15

Ser Leu Arg Leu Ser Cys Ala Val Ser Gly Phe Ser Phe Ser Thr Ser
            20                  25                  30

Cys Met Ala Trp Phe Arg Gln Ala Ser Gly Lys Gln Arg Glu Gly Val
        35                  40                  45

Ala Ala Ile Asn Ser Gly Gly Gly Arg Thr Tyr Tyr Asn Thr Tyr Val
    50                  55                  60

Ala Glu Ser Val Lys Gly Arg Phe Ala Ile Ser Gln Asp Asn Ala Lys
65                  70                  75                  80

Thr Thr Val Tyr Leu Asp Met Asn Asn Leu Thr Pro Glu Asp Thr Ala
                85                  90                  95

Thr Tyr Tyr Cys Ala Ala Val Pro Ala His Leu Gly Pro Gly Ala Ile
            100                 105                 110

Leu Asp Leu Lys Lys Tyr Lys Tyr Trp Gly Gln Gly Thr Gln Val Thr
        115                 120                 125

Val Ser Ser Leu Ala Ser Tyr Pro Tyr Asp Val Pro Asp Tyr Gly Ser
    130                 135                 140
```

(2) INFORMATION FOR SEQ ID NO: 36:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: camel heavy chain immunoglobulin" V-region followed
            by the FLAG sequence (pB24)

(ix) FEATURE:
        (A) NAME/KEY: CDS
        (B) LOCATION: 1..441

(xi) SEQUENCE DESCRIPTION: SEQ ID NO: 36:

```
CAG GTG AAA CTG CTC GAG TCT GGG GGA GGG TCG GTG CAG GCT GGA GGG      48
Gln Val Lys Leu Leu Glu Ser Gly Gly Gly Ser Val Gln Ala Gly Gly
 1               5                  10                  15

TCT CTG AGA CTC TCC TGT AAT GTC TCT GGC TCT CCC AGT AGT ACT TAT      96
Ser Leu Arg Leu Ser Cys Asn Val Ser Gly Ser Pro Ser Ser Thr Tyr
            20                  25                  30

TGC CTG GGC TGG TTC CGC CAG GCT CCA GGG AAG GAG CGT GAG GGG GTC     144
Cys Leu Gly Trp Phe Arg Gln Ala Pro Gly Lys Glu Arg Glu Gly Val
        35                  40                  45

ACA GCG ATT AAC ACT GAT GGC AGT GTC ATA TAC GCA GCC GAC TCC GTG     192
Thr Ala Ile Asn Thr Asp Gly Ser Val Ile Tyr Ala Ala Asp Ser Val
    50                  55                  60

AAG GGC CGA TTC ACC ATC TCC CAA GAC ACC GCC AAG AAA ACG GTA TAT     240
Lys Gly Arg Phe Thr Ile Ser Gln Asp Thr Ala Lys Lys Thr Val Tyr
65                  70                  75                  80
```

```
CTC CAG ATG AAC AAC CTG CAA CCT GAG GAT ACG GCC ACC TAT TAC TGC      288
Leu Gln Met Asn Asn Leu Gln Pro Glu Asp Thr Ala Thr Tyr Tyr Cys
             85                  90                  95

GCG GCA AGA CTG ACG GAG ATG GGG GCT TGT GAT GCG AGA TGG GCG ACC      336
Ala Ala Arg Leu Thr Glu Met Gly Ala Cys Asp Ala Arg Trp Ala Thr
        100                 105                 110

TTA GCG ACA AGG ACG TTT GCG TAT AAC TAC TGG GGC CGG GGG ACC CAG      384
Leu Ala Thr Arg Thr Phe Ala Tyr Asn Tyr Trp Gly Arg Gly Thr Gln
        115                 120                 125

GTC ACC GTC TCC TCA CTA GCT AGT TAC CCG TAC GAC GTT CCG GAC TAC      432
Val Thr Val Ser Ser Leu Ala Ser Tyr Pro Tyr Asp Val Pro Asp Tyr
        130                 135                 140

GGT TCT TAATAGAATT C                                                 449
Gly Ser
145
```

(2) INFORMATION FOR SEQ ID NO: 37:

(i) SEQUENCE CHARACTERISTICS:
        (A) LENGTH: 146 amino acids
        (B) TYPE: amino acid
        (D) TOPOLOGY: linear (ii) MOLECULE TYPE: protein (xi) SEQUENCE DESCRIPTION: SEQ ID NO: 37:

```
Gln Val Lys Leu Leu Glu Ser Gly Gly Gly Ser Val Gln Ala Gly Gly
 1               5                  10                  15

Ser Leu Arg Leu Ser Cys Asn Val Ser Gly Ser Pro Ser Thr Tyr
            20                  25                  30

Cys Leu Gly Trp Phe Arg Gln Ala Pro Gly Lys Glu Arg Glu Gly Val
            35                  40                  45

Thr Ala Ile Asn Thr Asp Gly Ser Val Ile Tyr Ala Ala Asp Ser Val
        50                  55                  60

Lys Gly Arg Phe Thr Ile Ser Gln Asp Thr Ala Lys Lys Thr Val Tyr
 65                 70                  75                  80

Leu Gln Met Asn Asn Leu Gln Pro Glu Asp Thr Ala Thr Tyr Tyr Cys
             85                  90                  95

Ala Ala Arg Leu Thr Glu Met Gly Ala Cys Asp Ala Arg Trp Ala Thr
        100                 105                 110

Leu Ala Thr Arg Thr Phe Ala Tyr Asn Tyr Trp Gly Arg Gly Thr Gln
        115                 120                 125

Val Thr Val Ser Ser Leu Ala Ser Tyr Pro Tyr Asp Val Pro Asp Tyr
        130                 135                 140

Gly Ser
145
```

(2) INFORMATION FOR SEQ ID NO: 38:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: See figure 6

(xi) SEQUENCE DESCRIPTION: SEQ ID NO: 38:

```
AATTTAGCGG CCGCCCAGGT GAAACTGCTC GAGTAAGTGA CTAAGGTCAC CGTCTCCTCA      60
```

```
GAACAAAAAC TCATCTCAGA AGAGGATCTG AATTAATGAG AATTCATCAA ACGGTGATA      119
```

(2) INFORMATION FOR SEQ ID NO: 39:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: See figure 6

(xi) SEQUENCE DESCRIPTION: SEQ ID NO: 39:

```
AGCTTATCAC CGTTTGATGA ATTCTCATTA ATTCAGATCC TCTTCTGAGA TGAGTTTTTG      60
TTCTGAGGAG ACGGTGACCT TAGTCACTTA CTCGAGCAGT TTCACCTGGG CGGCCGCTAA     120
```

(2) INFORMATION FOR SEQ ID NO: 40:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: See figure 6

(xi) SEQUENCE DESCRIPTION: SEQ ID NO: 40:

```
Ala Gln Val Lys Leu Leu Glu
1               5
```

(2) INFORMATION FOR SEQ ID NO: 41:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: See figure 6

(xi) SEQUENCE DESCRIPTION: SEQ ID NO: 41:

```
Val Thr Val Ser Ser Glu Gln Lys Leu Ile Ser Glu Glu Asp Leu Asn
1               5                   10                  15
```

(2) INFORMATION FOR SEQ ID NO: 42:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: See figure 19

(xi) SEQUENCE DESCRIPTION: SEQ ID NO: 42:

```
AATTTAGTCG CGACAGGTGA AACTGCTCGA GTAAGTGACT AAGGTCACCG TCTCCTCAGA      60
```

```
ACAAAAACTC ATCTCAGAAG AGGATCTGAA TTAATGAGAA TTCATCTTAA GGTGATA         117
```

(2) INFORMATION FOR SEQ ID NO: 43:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: See figure 19

(xi) SEQUENCE DESCRIPTION: SEQ ID NO: 43:

```
AGCTTATCAC CTTAAGATGA ATTCTCATTA ATTCAGATCC TCTTCTGAGA TGAGTTTTTG      60

TTCTGAGGAG ACGGTGACCT TAGTCACTTA CTCGAGCAGT TTCACCTGTC GCGACTA         117
```

(2) INFORMATION FOR SEQ ID NO: 44:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: See figure 19

(xi) SEQUENCE DESCRIPTION: SEQ ID NO: 44:

```
Arg Gln Val Lys Leu Leu
1               5
```

(2) INFORMATION FOR SEQ ID NO: 45:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: See figure 19

(xi) SEQUENCE DESCRIPTION: SEQ ID NO: 45:

```
Val Thr Val Ser Ser Glu Gln Lys Leu Ile Ser Glu Glu Asp Leu Asn
1               5                   10                  15
```

(2) INFORMATION FOR SEQ ID NO: 46:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 46:

```
Gln Val Lys Leu
1
```

(2) INFORMATION FOR SEQ ID NO: 47:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 47:

Val Thr Val Ser Ser
1               5

(2) INFORMATION FOR SEQ ID NO: 48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

GTCACCGTCT CCTCATAATG A                                              21

(2) INFORMATION FOR SEQ ID NO: 49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 49:

AGCTTCATTA TGAGGAGACG                                                20

(2) INFORMATION FOR SEQ ID NO: 50:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 50:

GTCACCGTCT CCTCATAATG ATCTTAAGGT GATA                                34

(2) INFORMATION FOR SEQ ID NO: 51:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 51:

AGCTTATCAC CTTAAGATCA TTATGAGGAG ACG                                 33

(2) INFORMATION FOR SEQ ID NO: 52:

(i) SEQUENCE CHARACTERISTICS:
        (A) LENGTH: 12 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO: 52:

AATTGCGGCC GC                                                                    12

(2) INFORMATION FOR SEQ ID NO: 53:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

CATGCAGTCT TCGGGC                                                                16

(2) INFORMATION FOR SEQ ID NO: 54:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 54:

TTAAGCCCGA AGACTG                                                                16

(2) INFORMATION FOR SEQ ID NO: 55:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

TCACTGAATT CGGGATCATG AGGACTCTCC TTGTGAGCTC GCTT                                  44

(2) INFORMATION FOR SEQ ID NO: 56:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

ATGTCACAAA GCTTAAGCAC GAAGACAGTC GACCGTGCGG CCGGAGAC                              48

(2) INFORMATION FOR SEQ ID NO: 57:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

CGCGTCCATG CAGTCCTCAG GTGGATCATC CCAGGTGAAA CTGC                    44

(2) INFORMATION FOR SEQ ID NO: 58:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

TCGAGCAGTT TCACCTGGGA TGATCCACCT GAGGACTGCA TGGA                    44

(2) INFORMATION FOR SEQ ID NO: 59:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 59:

Ser Met Gln Ser Ser Gly Gly Ser Ser Gln Val Lys Leu Leu Glu
1               5                   10                  15

(2) INFORMATION FOR SEQ ID NO: 60:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

CATGGCCAGG TGAAACTGCT CGAGTAAGTG ACTAAGGTCA CCGTCTCCTC AGC          53

(2) INFORMATION FOR SEQ ID NO: 61:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 61:

GGCCGCTGAG GAGACGGTGA CCTTAGTCAC TTACTCGAGC AGTTTCACCT GGC          53

(2) INFORMATION FOR SEQ ID NO: 62:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 62:

-continued

```
Ser Ser Gly Gly Ser Ser
1               5

(2) INFORMATION FOR SEQ ID NO: 63:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: human heavy chain framework (subgroup III)

(xi) SEQUENCE DESCRIPTION: SEQ ID NO: 63:

Trp Val Arg Gln Ala Pro Gly Lys Gly Leu Glu Trp Val Ser
1               5                   10

(2) INFORMATION FOR SEQ ID NO: 64:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: human heavy chain framework (subgroup III)

(xi) SEQUENCE DESCRIPTION: SEQ ID NO: 64:

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

(2) INFORMATION FOR SEQ ID NO: 65:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: human heavy chain framework (subgroup III)

(xi) SEQUENCE DESCRIPTION: SEQ ID NO: 65:

Trp Gly Gln Gly Thr Leu Val Thr Val Ser Ser
1               5                   10

(2) INFORMATION FOR SEQ ID NO: 66:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" framework A (xi) SEQUENCE DESCRIPTION: SEQ ID NO: 66:
```

-continued

```
Trp Phe Arg Glu Gly Pro Gly Lys Glu Arg Glu Gly Ile Ala
1               5                   10
```

(2) INFORMATION FOR SEQ ID NO: 67:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" framework A (xi) SEQUENCE DESCRIPTION: SEQ ID NO: 67:

```
Arg Phe Thr Ile Ser Gln Asp Ser Thr Leu Lys Thr Met Tyr Leu Leu
1               5                   10                  15
Met Asn Asn Leu Lys Pro Glu Asp Thr Gly Thr Tyr Tyr Cys Ala Ala
                20                  25                  30
```

(2) INFORMATION FOR SEQ ID NO: 68:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" framework A (xi) SEQUENCE DESCRIPTION: SEQ ID NO: 68:

```
Trp Gly Gln Gly Thr Gln Val Thr Val Ser Ser
1               5                   10
```

(2) INFORMATION FOR SEQ ID NO: 69:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" framework B (xi) SEQUENCE DESCRIPTION: SEQ ID NO: 69:

```
Trp Tyr Arg Gln Ala Pro Gly Lys Glu Arg Glu Phe Val Ser
1               5                   10
```

(2) INFORMATION FOR SEQ ID NO: 70:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" framework B (xi) SEQUENCE DESCRIPTION: SEQ ID NO: 70:

```
Arg Phe Thr Ile Ser Gln Asp Ser Ala Lys Asn Thr Val Tyr Leu Gln
1               5                   10                  15

Met Asn Ser Leu Lys Pro Glu Asp Thr Ala Met Tyr Tyr Cys Lys Ile
            20                  25                  30

(2) INFORMATION FOR SEQ ID NO: 71:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: camel "heavy chain immunoglobulin" framework B (xi) SEQUENCE DESCRIPTION: SEQ ID NO: 71:

Trp Gly Gln Gly Thr Gln Val Thr Val Ser Ser
1               5                   10
```

PROSUCTION OF ANTIBODIES OR (FUNCTIONALIZED) FRAGMENTS THEREOF DERIVED FROM HEAVY CHAIN IMMUNOGLOBULINS OF CAMELIDAE

RELATED APPLICATIONS

This application is a continuation of U.S. patent application Ser. No. 08/537,871, filed Jan. 29, 1996, (now U.S. Pat. No. 6,838,254), which claims the benefit under 35 U.S.C. §371 to PCT international application number PCT/EP94/01442, filed Apr. 28, 1994 which claims the benefit of priority of European Patent Application No. 93202079.5, filed Jul. 15, 1993, European Patent Application No. 93201454.1, filed May 19, 1993 and European Patent Application No. 93201239.6, filed Apr. 29, 1993, which are herein incorporated by reference in their entireties.

The present invention relates to a process for the production of antibodies or (functionalized) fragments thereof derived from heavy chain immunoglobulins of Camelidae and is partly based on research investigations carried out at the Free University of Brussels. A draft publication thereon already submitted to the periodical Nature and communicated to the present applicants by Prof. R. Hamers reads as follows.

Functional Heavy Chain Immunoglobulins in the Camelids

Random association of $V_L$ and $V_H$ repertoires contributes considerably to antibody diversity (1). The diversity and the affinity are then increased by hypermutation in B-cells located in germinal centres (2). Except in the heavy chain disease (3), naturally occurring heavy chain antibodies have not been described, although antigen binding has been demonstrated for separated heavy chains (4) or cloned $V_H$ domains (5). The presence of considerable amounts IgG like material of 100 Kd in the serum of the camel (Camelus dromedarius) (6) was confirmed. These molecules are composed of heavy chain dimers and are devoid of light chains. Nevertheless they bear an extensive antigen binding repertoire, a finding which questions the role of the light chains in the camel. Camel heavy chain IgGs lack the $C_H1$, which in one IgG class might be structurally replaced by an extended hinge. Heavy chain IgGs are a feature of all camelids. These findings open perspectives in engineering of antibodies.

By a combination of affinity chromatography on Protein A and Protein G, three quantitatively important fractions corresponding to subclasses of IgG can be isolated from the serum of camels (Camelus dromedarius) (FIG. 1A, lanes c-f). One fraction ($IgG_1$) contains molecules of 170 Kd (FIG. 1B, lane 2) which upon reduction yield 50 Kd heavy chains and large 30 kD light chains (FIG. 1C, lane 2). The two other immunoglobulin fractions contain molecules of approximately 100 Kd (FIG. 1B, lanes 1 and 3) which on reduction yield only heavy chains of respectively 46 Kd ($IgG_2$ fraction binding only to Protein A) (FIG. 1C, lane 3) and 43 Kd ($IgG_3$ fraction binding to Protein A and Protein G) (FIG. 1C, lane 1). These two IgG classes appear to lack the light chain completely.

To exclude the possibility that the light chains were only weakly associated with the heavy chains and lost during the selective purification, whole serum was size fractionated by gel filtration. Coomassie blue staining of unreduced fractions revealed the sequential elution of the 170 Kd $IgG_1$ followed by the incompletely resolved isotypes $IgG_2$ and $IgG_3$ (90 Kd) (FIG. 1D, upper inset). Immunostaining of the same fractions after reduction confirmed that the light chains were present solely in the 50 Kd heavy chain containing fractions (FIG. 1D, lower inset).

A comparative study of old world camelids (Camelus bactrianus and Camelus dromedarius) and new world camelids (Lama pacos, Lama glama and Lama vicugna) showed that heavy chain immunoglobulins are abundant in the sera of all species examined (data not shown) and total up to 75% of the molecules binding to protein A.

The abundance of the heavy chain immunoglobulins in the serum of camelids raises the question as to whether they bear an extensive antigen binding repertoire. This question could be answered by examining the $IgG_1$, $IgG_2$ and $IgG_3$ fractions from the serum of camels (Camelus dromedarius) with a high antitrypanosome titer (7). In radio-immunoprecipitation, purified fractions of $IgG_1$, $IgG_2$ and $IgG_3$ derived from infected camels were shown to bind a large number of antigens present in a $^{35}S$ methionine labelled trypanosome lysate (FIG. 2A), indicating an extensive repertoire complexity for the three IgG classes. Conversely, in blotting experiments, $^{35}S$ methionine labelled trypanosome lysate binds to SDS-PAGE separated $IgG_1$, $IgG_2$ and $IgG_3$ obtained from infected animals (FIG. 2B). These findings indicate that the heavy chains alone chain generate an extensive repertoire and question the obligatory contribution of the light chain to the useful antibody repertoire in the camelids.

The camelid γ2 and γ3 chains are considerably shorter than the normal mammalian γ or camel γ1 chains. This would suggest that, as in the case of heavy chain disease (3). deletions have occurred in the $C_H1$ protein domain (8,9). To address this question, cDNA was synthesized from camel spleen mRNA and the sequences between the 5' end of the $V_H$ and the $C_H2$ were amplified by a Polymerase Chain Reaction (PCR), and cloned. Seventeen clones presenting a different $V_H$ sequence were isolated and sequenced. Their most striking feature was the complete lack of the $C_H1$ domain, the last framework (FR4) residues of the $V_H$ region being immediately followed by the hinge (FIG. 3, lower part). The absence of the $C_H1$ domain clarifies two important dilemmas.

First, immunoglobulin heavy chains are normally not secreted unless the heavy chain chaperoning protein or BIP (10) has been replaced by the L chain (11), or alternatively the $C_H1$ domain has been deleted (3,8,9). Secondly, isolated heavy chains from mammalian immunoglobulins tend to aggregate, but are only solubilized by light chains (8,12) which bind to the $C_H1$ and the $V_H$ domains (13).

14 of the 17 clones were characterized by a short hinge sequence with a length equal to that of human $IgG_2$ and $IgG_4$ (14) (FIG. 3). The other 3 had a long hinge sequence containing the 'EPK' hinge motif found in human $IgG_1$ and $IgG_3$ (14). They possess the $C_H2$ 'APELL/P' motif also found in human $IgG_1$ and $IgG_3$ (see SEQ. ID. NO: 1-2), and which is associated with mammary transport of bovine $IgG_1$ (15). On basis of molecular weight, we expect the "short hinge" clones to correspond to $IgG_3$ and the "long hinge" clones to $IgG_2$.

In the short hinge containing antibody, the extreme distance between the extremities of the $V_H$ regions will be of the order of 80 Å corresponding to twice the size of a single domain of 40 Å ($2 \times V_H$) (16). This could be a severe limitation for agglutinating, cross linking or complement fixation (17, 18). In the long hinge containing immunoglobulin the absence of $C_H1$ might be compensated by the extremely long hinge itself, composed of a 12 fold repeat of the sequence Pro-X (X=Gln, Glu, Lys) (FIGS. 3 & 4). NMR (19) and molecular modelling (20) of Pro-X repeats present in the TonB protein of E. coli (X=Glu, Lys) and the membrane procyclin of trypanosomes (X=Asp, Glu) indicate that these repeated sequences function as rigid rodlike spacers with a diameter of 8 Å and a rise of 2.9 Å per residue. Assuming the same geometry, the long hinge would be 70 Å which compensates for the absence of the $C_H 1$ domain.

The binding site of heavy chain antibodies cannot form the pocket resulting from adjoining light and heavy chain V regions and the residues of the $V_H$ which normally interact with $V_L$ will be exposed to solvent (3,5,13). It was found that leucine at position 45 conserved in 98% of human and murine $V_H$ sequences (14), and crucial in the $V_H$-$V_L$ association (13), can be replaced by an arginine (FIG. 3, upper part). This substitution is in accordance with both the lost contact with a $V_L$ domain and an increased solubility.

Unlike myeloma heavy chains which result mainly from $C_H 1$ deletion in a single antibody producing cell (21) the camelid heavy chain antibodies have emerged in a normal immunological environment and it is expected that they will have undergone the selective refinement in specificity and affinity accompanying B cell maturation (1, 2). The obtention of camelid heavy chain antibodies could therefore be an invaluable asset in the development and engineering of soluble $V_H$ domains (5) or of new immunologicals for diagnostic, therapeutic or biochemical purposes.

REFERENCES

1. Tonegawa, S. *Nature* 302, 575-581 (1983).
2. Jacob, J, Kelsoe, G., Rajewski, K., & Weiss, U. *Nature* 354, 389-392 (1991).
3. Fleischman J. B., Pain R. H. & Porter R. R. *Arch. Biochem. Biophys Suppl.* 1, 174-180 (1962).
4. Utsumi, S. & Karush, F. *Biochemistry* 3, 1329-1338 (1964).
5. Ward, E. S., Güssow, D., Griffiths, A. d., Jones, P. T. & Winter G. *Nature* 341, 544-546 (1989).
6. Ungar-Waron H., Eliase E. Gluckman A. and Trainin Z. *Isr. J. Vet. Med.* 43, 198-203 (1987).
7. Bajyana Songa, E., & Hamers R. *Ann. Soc. Belge Med. Trop.* 68, 233-240 (1988).
8. Seligmann M., Mihaesco E. Preud'homme J.-L, Danon F. & Brouet J.-C. *Immun Rev.* 48, 145-167 (1979).
9. Traunecker, A., Schneider, J., Kiefer, H., Karjalaien, K., *Nature* 339, 68-70 (1989).
10. Henderschot L. M., Bole D., Köhler, G. & Kearney, J. F. *J. Cell Biol.* 104, 761-767 (1987).
11. Henderschot L. M. *J. Cell Biol.* 111, 829-837 (1990).
12. Roholt O., Onoue K. & Pressman D. *Proc. Natl. Acad. Sci USA* 51, 173-178 (1964).
13. Chothia, C., Novotny, J., Bruccoleri, R., Karplus, M. *J. Mol. Biol.* 186, 651-663 (1985).
14. Kabat E. A., Wu, T. T., Reid-Miller, M., Perry H. M. & Gottesman, K. S. *Sequences of Proteins of Immunological Interest* 511 (U.S. Dept of Health and Human Services, US Public Health Service, National Institutes of Health, Bethesda, 1987).
15. Jackson, T., Morris, B. A, Sanders, P. G. *Molec. Immun.* 29, 667-676 (1992).
16. Poljak R. J. et al. *Proc. Natn. Acad. Sci. USA* 70, 3305-3310 (1973).
17. Dangl J. L., et al. *EMBO J.* 7, 1989-1994 (1988).
18. Schneider W. P. et al. *Proc. Natn. Acad. Sci USA* 85, 2509-2513 (1988).
19. Evans, J. S. et al. *FEBS Lett.* 208, 211-216 (1986).
20. Roditi, I. et al. *J. Cell Biol.* 108, 737-746 (1989).
21. Dunnick, W., Rabbits, T. H., Milstein, C. *Nucl. Acids Res.*, 8, 1475-1484 (1980).
22. Bülow, R., Nonnengässer, C., Overath, P. *Mol. Biochem. Parasitol.* 32, 85-92 (1989).
23. Sambrook, J., Fritsch, E. F. & Maniatis, T. *Molecular Cloning: A Laboratory Manual* 2nd Edn (Cold Spring Harbor Laboratory Press, New York, 1989).
24. Sastry, L et al. *Proc. Natn. Acad. Sci.* USA 86, 5728-5732 (1989).
25. Sanger, F., Nicklen, S. & Coulson, A. R. *Proc. Natn. Acad. Sci.* USA 74, 5463-5467 (1977).
26. Klein, *J. Immunology* (Blackwell Scientific Publications, London, 1990).

FIG. 1 Characterisation and Purification of Camel IgG Classes on Protein A, Protein G and Gel Filtration.

(A) The friction of *C. dromedarius* serum adsorbed on Protein A shows upon reduction on SDS-PAGE three heavy chain components of respectively 50, 46, and 43 Kd (bands between dots), absent in the non adsorbed fraction (lane d), and light chain components of around 30 Kd (lane c) considerably larger than rabbit light chain (lane a, rabbit IgG). The fractions adsorbed on Protein G (lane e) lack the 46 Kd heavy chain which remains in the non adsorbed fraction (lane f). Lane b contains a size marker.

(B and C) By differential adsorption and elution on Protein G and Protein A, the IgG fractions containing 43 Kd (lane 1), 46 Kd (lane 3) and 50 Kd (lanes 2) heavy chains were purified and analysed on SDS-PAGE in absence (B) or presence (C) of DTT.

(D) Whole camel serum (0.1 ml) was fractionated by gel filtration on a Superdex 200 column using 150 mM NaCl, 50 mM sodium phosphate buffer pH 7.0 as eluent. Affinity purified $IgG_2$ and $IgG_3$ elute at the positions indicated by arrows. The fractions of interest were further analysed by SDS-PAGE with or without prior reduction. The protein contents as visualized by Coomassie blue (without reduction, upper inset) are compared with the immunoglobulins from the same fractions (after reduction with DTT, lower inset) as revealed by Western blotting with a rabbit anti-camel-IgG (lower inset).

METHODS. 5 ml of *C. dromedarius* serum is adsorbed onto a 5 ml Protein G Sepharose (Pharmacia) column, and washed with 20 mM phosphate buffer, pH 7.0. Upon elution with 0.15 M NaCl, 0.58% acetic acid (pH 3.5), $IgG_3$ of 100 Kd is eluted which upon reduction yields heavy chains of 43 Kd (lane 1, B and C). $IgG_1$ of 170 Kd can subsequently be eluted with pH 2.7 buffer (0.1 M Gly-HCl). This fraction, upon reduction, yields a 50 Kd heavy chain and a broad light chain band (lane 2, C). The fraction not adsorbed on Protein G is brought on a 5 ml Protein A Sepharose column. After washing and elution with 0.15 M NaCl, 0.58% acetic acid (pH 4.5) $IgG_2$ of 100 Kd is obtained which consists solely of 46 Kd heavy chains (lane 3, C).

FIG. 2 Repertoire Complexity and Antigen Binding Capacity of Camel $IgG_1$, $IgG_2$ and $IgG_3$ Analysed by Radioimmunoprecipitation (A) or Western Blotting (B & C).

(A) Serum or purified IgG fractions from healthy or *Trypanoma evansi* infected *C. dromedarius* (CATT titer 1/160 (7)) were incubated with labeled trypanosome lysate, recovered with Protein A SEPHAROSE and analysed by SDS-PAGE. The relative counts recovered are inscribed below each lane. No trypanosome proteins bind to the Protein A or to the healthy camel immunoglobulins.

(B) 20 µg of $IgG_1$, $IgG_2$, and $IgG_3$ from healthy and trypanosome infected animals were separated by SDS-PAGE without prior reduction or heating. The electroblotted proteins were incubated with the labeled trypanosome lysate. The $IgG_2$ shows a single antigen binding component corresponding to the heavy chain immunoglobulin whereas the IgG$_3$ fraction appears to contain in addition two larger antigen binding components barely detectable by PONCEAU RED staining (C). These are possibly Ig classes copurified as immunocomplexes present in the serum of the infected animals.

METHODS. ($^{35}$S)-methionine labeled *Trypanosoma evansi* lysate (500,000 counts) (22) was incubated (4° C., 1 hour) with 10 μL of serum or, 20 μg of IgG$_1$, IgG$_2$ or IgG$_3$ in 200 μl of 0.4 M NaCl, 10 mM EDTA, 10 mM Tris (pH 83), containing 0.1 M TLCK. 10 mg of Protein A SEPHAROSE suspended in 200 μl of the same buffer was added (4° C., 1 hour). After washing and centrifugation, each pellet was resuspended in 75 μL SDS PAGE sample solution containing DTT, and heated for 3 min. at 100° C. After centrifugation, 5 μl of the supernatant was saved for radioactivity counting and the remainder analysed by SDS PAGE and fluorography. The nitrocellullose filter of the Western blot of purified fractions IgG$_1$, IgG$_2$ and IgG$_3$ was stained with PONCEAU RED (C) or incubated with 1% ovalbumin in TST buffer (Tris 10 mM, NaCl 150 mM, Tween 0.05%) (B). The membrane was extensively washed with TST buffer and incubated for 2 hours with ($^{35}$S)-labeled trypanosome antigen. To avoid unspecific binding, the labeled trypanosome antigen lysate was filtered (45 μL) and incubated with healthy camel immunoglobulin and ovalbumin adsorbed on a nitrocellulose membrane.

FIG. 3 Amino Acid Sequences of the V$_H$ Framework, and Hinge/C$_H$2 of *Camelus dromedarius* Heavy Chain Immunoglobulins, Compared to Human (Italic) V$_H$ Framework (Subgroup III) and Hinges of Human IgG (14).

METHODS. Total RNA was isolated from a dromedary spleen (23). mRNA was purified with oligo T-paramagnetic beads (PolyATract-Promega). 1 μg mRNA was used for preparing double-strand cDNA (23) after an oligo-dT priming using enzymes provided by Boehringer Mannheim. 5 μg of cDNA was amplified by PCR in a 100 μl reaction mixture (10 mM Tris-HCl pH 8.3, 50 mM KCl, 15 mM MgCl$_2$, 0.01% (w/v) gelatine, 200 μM of each dNTP). 25 pmoles of each oligonucleotide of the mouse V$_H$ (24), containing a XhoI site, and 5'-CGCCATCAAGGTACCAGT-TGA-3' (see SEQ. ID. NO: 3) were used as primers. The 3' end primer was deduced from partial sequences corresponding to γ chain amino acid 296 to 288 (T. Atarhouch, C. Hamers-Casterman, G. Robinson, private communication) in which one mismatch was introduced to create a KDnI restriction site. After a round of denaturing annealing (94° C. for 5 min. and 54° C. for 5 min.), 2 U of Taq DNA polymerase were added, to the reaction mixture before subjecting it to 35 cycles of amplification (5). The PCR products were purified by phenol-chloroform extraction followed by HPLC (Genpak-fax column, Waters) and finally by MERMAID (BIO 101, Inc.). After these purification steps, the amplified cDNA was digested with XhoI and KpnI, and ligated into pBluescript.

The clones were sequenced by the dideoxy chain termination method (25). The sequences were translated into amino acids which allowed their assignment to well defined domains of the Ig molecule (14); see SEQ. ID. NO: 4-12

FIG. 4 Schematic Representation of the Structural Organisation of the Camel Immunoglobulins (Adapted from 26).

On the basis of size consideration, the IgG$_1$ fraction possess probably the normal antibody assembly of two light and two heavy chains. IgG$_3$ would have a hinge comparable in size to the human IgG$_1$, IgG$_2$, and IgG$_3$. The two antigen binding sites are much closer to each other as this camel IgG lacks the C$_H$1 domain. In the camel IgG$_2$ the long hinge, being formed of Pro-X repeats (X=Glu, Gln or Lys), most likely adopt a rigid structure (19,20). This long hinge could therefore substitute the C$_H$1 domain and bring the two antigen binding sites of IgG$_2$ to normal positions.

BACKGROUND OF THE INVENTION

Already at a very early stage during evolution antibodies have been developed to protect the host organisms against invading molecules or organisms. Most likely one of the earliest forms of antibodies must have been developed in Agnatha. In these primitive fishes antibodies of the IgM type consisting of heavy and lights chains have been detected. Also in many other forms of life ranging from amphibians to mammals antibodies are characterized by the feature that they consist of two heavy and two light chains, although the heavy chains of the various classes of immunoglobulins are quite different. These heavy and light chains interact with each other by a number of different physical forces, but interactions between hydrophobic patches present on both the heavy and light chain are always important. The interaction between heavy and light chains exposes the complementarity determining regions (CDRs) of both chains in such a way that the immunoglobulin can bind the antigen optimally. Although individual heavy or light chains have also the capability to bind antigens (Ward et al., Nature 341 (1989) 544-546=ref. 5 of the above given draft publication) this binding is in general much less strong than that of combined heavy and light chains.

Heavy and light chains are composed of constant and variable domains. In the organisms producing immunoglobulins in their natural state the constant domains are very important for a number of functions, but for many applications of antibodies in industrial processes and products their variable domains are sufficient. Consequently many methods have been described to produce antibody fragments.

One of these methods is characterized by cleavage of the antibodies with proteolytic enzymes like papain and pepsin resulting in (a) antibody fragment comprising a light chain bound via an S—S bridge to part of a corresponding heavy chain formed by proteolytic cleavage of the heavy chain (Fab), or (b) a larger fragment of the antibody comprising two of these Fabs still connected to each other via an S—S bridge in enlargements of the heavy chain parts, indicated with F(ab)$_2$, respectively (see patent applications EP-A-0125023 (GENENTECH/Cabilly et al., 1984) and WO-A-93/02198 (TECH. RES. CENT. FINLAND/Teeri et al., 1993) for definitions of these abbreviations). The disadvantage of the enzymatic route is that the production of whole antibodies is expensive and the enzymatic processing increases the costs of these fragments even more. The high costs of antibody fragments block the application of these fragments in processes and products outside the pharmaceutical industry.

Another method is based on, linkage on DNA level of the genes encoding (parts of) the heavy chain and the light chain. This linkage and the subsequent production of these chimeric immunoglobulins in microorganisms have been described (for Fab fragments see e.g. Better et al., Science 240 (1988) 1041-1043, for F$_v$ fragments (combination of variable fragments of the heavy chain (V$_H$) and light chain (V$_L$) still connected to each other by non-covalent binding interactions) see e.g. Skerra et al., Science 240 (1988) 1938, and for single chain F$_v$ fragments (ScF$_v$; an F$_v$ fragment in which the two variable fragments are linked to each other by a linker peptide) see e.g. Bird et al., Science 242 (1988) 423426. Provided that an appropriate signal sequence has been placed in front of the single chain V$_H$ and V$_L$ antibody fragment (ScF$_v$), these products are translocated in *E. coli* into the periplasmic space and can be isolated and activated using quite elaborate and costly procedures. Moreover the application of antibody fragments produced by *E. coli* in consumer products requires extensive purification processes to remove pyrogenic factors originating from *E. coli*. For this and other reasons the production of $ScF_v$ in microorganisms that are normally used in the fermentation industry, like prokaryotes as *Streptomyces* or *Bacillus* (see e.g. Wu et al. Bio/Technology 11 (1993) 71) or yeasts belonging to the genera *Saccharomyces* (Teeri et al., 1993, supra), *Kluyveromyces, Hansenula,* or *Pichia* or moulds belonging to the genera *Aspergillus* or *Trichoderma* is preferred. However with a very few exceptions the production of $ScF_v$ antibodies using these systems proved to be impossible or quite poor. Although the exact reasons for the poor production are not well known, the use of linkers between the $V_H$ and $V_L$ chains not designed for secretion (Teeri et al., 1993, supra) may be a reason.

Another reason may be incorrect folding of $ScF_v$. The frameworks and to a limited extend the CDRs of variable domains of light and heavy chains interact with each other. It has been described by Chothia et al. (J. Mol. Biol. 186 (1985) 651-663=ref. 13 of the above given draft publication) that this interaction involves amino acids at the following positions of the variable region of the heavy chain: 35, 37, 39, 44-45, 47, 100-103 and 105 (numbering according to Kabat et al., In "*Sequences of Proteins of immunological Interest*, Public Health Service, NIH, Washington D.C., 1983=ref 14 of the above given draft publication). Especially leucine at position 45 is strongly conserved and the whole a polar side chain of this amino acid seems to be involved in the interaction with the light chain. These strong interactions may fold the $ScF_v$ into a structure that can not be translocated in certain types of lower eukaryotes.

Thus the use of a linker in the production of $ScF_v$ for connecting a $V_H$ chain to a $V_L$ chain, might negatively influence either the translocation, or the folding of such $ScF_v$ or both.

Not prior-published European patent application 92402326.0 filed 21 Aug. 1992 (C. Casterman & R. Hamers) discloses the isolation of new animal-derived immunoglobulins devoid of light chains (also indicated as heavy chain immunoglobulins), which can especially originate from animals of the camelid family (Camelidae). This European patent specification, now publicly available as EP-A1-0 584 421, is incorporated herein by reference. These heavy chain immunoglobulins are characterized in that they comprise two heavy polypeptide chains sufficient for the formation of one or more complete antigen binding sites, whereby a complete antigen binding site means a site which will alone allow the recognition and complete binding of an antigen, which can be verified by any known method regarding the testing of the binding affinity. The European patient specification further discloses methods for isolating these heavy chain immunoglobulins from the serum of Camelidae and details of the chemical structure of these heavy chain immunoglobulins. It also indicates that these heavy chain immunoglobulins and derivatives thereof can be made by using recombinant DNA technology in both prokaryotes and eukaryotes. The present invention relates to a further development of the work disclosed in that prior-filed but not prior-published European specification.

Due to the absence of light chains in most of the immunoglobulins of Camelidae such linkers are not necessary, thereby avoiding the above-mentioned potential problems.

As described above in the draft publication for Nature, now publicly available as Nature 363 (3 Jun. 1993) 446-448, and in the not prior-published European patent application 92402326.0 (supra) it was surprisingly found that the majority of the protein A-binding immunoglobulins of Camelidae consists just of two heavy chains and that these heavy chains are quite different from common forms of heavy chains, as the $C_H1$ domain is replaced by a long or short hinge (indicated for $IgG_2$ and $IgG_3$, respectively, in FIG. 4 of the above given draft publication for Nature). Moreover these heavy chains have a number of other features that make them remarkably different from the heavy chains of common immunoglobulins.

One of the most significant features is that they contain quite different amino acid residues at those positions involved in binding to the light chain, which amino acids are highly conserved in common immunoglobulins consisting of two heavy and two light chains (see Table 1 and SEQ. ID. NO: 13-31).

TABLE 1

Comparison af amino acid sequences of various immunoglobulins Alignment of a number of $V_{11}$ regions of Camel heavy chain antibodies compared with those of mouse (M, top line) and human (H, second line). Framework fragments are indicated in capitals, CDR fragments in small print; see SEQ. ID. NO: 13-31 for sequences indicated by M, H, 1, 2, 3, 7, 9, 11, 13, 16, 17, 18, 19, 20, 21, 24, 25, 27, 29, respectively.

```
                   1                                                          50
       m   EVKLVESGGG  LVQPGGSLRL  SCATSGFTFS  dfyme..WVR  QPPGKRLEWI h   EVQLVESGGG  LVQPGGSLRL  SCAASGFTFS  syams..WVR  QAPGKGLEWV cam1   ........GG  SVQAGGSLRL  SCAASGYSNC  pltws..WYR  QFPGTEREFV cam2   DVQLVASGGG  SVQAGGSLRL  SCTASGDSFS  rfams..WFR  QAPGKECELV cam3   ........GG  SVQTGGSLRL  SCAVSGFSFS  tscma..WFR  QASGKQREGV cam7   ........GG  SVQGGGSLRL  SCAISGYTYG  sfcmg..WFR  EGPGKEREGI cam9   ........GG  SVQAGGSLTL  SCVYTNDTGT  ...mg..WFR  QAPGKECERV cam11   ........GG  SVQAGGSLRL  SCNVSGSPSS  tyclg..WFR  QAPGREREGV cam13   ........GG  SVEAGGSLRL  SCTASGYVSS  ...ma..WFR  QVPGQEREGV
```

TABLE 1-continued

Comparison af amino acid sequences of various
immunoglobulins Alignment of a number of V_H regions of
Camel heavy chain antibodies compared with those of mouse
(M, top line) and human (H, second line). Framework
fragments are indicated in capitals, CDR fragments in small
print; see SEQ. ID. NO: 13-31 for sequences indicated by M,
H, 1, 2, 3, 7, 9, 11, 13, 16, 17, 18, 19, 20, 21, 24, 25,
27, 29, respectively.

```
cam16    ........GG SAQAGGSLRL SCAAHGIPLN gyyia..WFR QAPGKGREGV cam17    ........GG SVQPGGSLTL SCTVSGATYS dysig..WIR QAPGKDREVV cam18    ........GG SVQAGGSLRL SCTGSGFPYS tfclg..WFR QAPGKEREGV cam19    ........GG SVQAGGSLRL SCAASDYTIT dycma..WFR QAPGKERELV cam20    ........GG SVQVGGSLRL SCVASTHTDS stcig..WFR QAPGKEREGV cam21    ........GG SVQVGGSLKL SCKISGGTPD rvpkslaWFR QAPEKEREGI cam24    ........GG SVQAGGSLRL SCNVSGSPSS tyclg..WFR QAPGKEREGV cam25    ........GG SVQTGGSLRL SCEISGLTFD dsdvg..WYR QAPGDECKLV cam27    ........GG SVQAGGSLRL SCASSSKYMP ctydmt.WYR QAPGKEREFV cam29    .....eXXGG SVQAGGSLRL SCVASGFNFE tsrma..WYR QTPGNVCELV 51                                              100
       m A..asrnkan dytteysasv kgRFIVSRDT SQSILYLQMN ALRAEDTAIY h S..xisxktd ggxtyyadsv kgRFTISRDN SKNTLYLQMN SLRAEDTAVY cam1 S..smd...p dgntkytysv kgRFTMSRGS TEYTVFLQMD NLKPEDTAMY cam2 S..siq...s ngrtteadsv qgRFTISRDN SRNTVYLQMN SLKPEDTAVY cam3 Aainsgggrt yyntyvaesv kgRFAISQDN AKTTVYLDMN NLTPEDTATY cam7 A..tiln..g gtntyyadsv kgRFTISQDS TLKTMYLLMN NLKPEDTGTY cam9 A..hit...p dgmtfidepv kgRFTISRDN AQKTLSLRMN SLRPEDTAVY cam11 T..aint..d gsiiyaadsv kgRFTISQDT AKETVHLQMN NLQPEDTATY cam13 A..fvqt..a dnsalygdsv kgRFTISHDN AKNTLYLQMR NLQPDDTGVY cam16 A..ting..g rdvtyyadsv tgRFTISRDS PKNTVYLQMN SLKPEDTAIY cam17 A..aant..g atskfyvdfv kgRFTISQDN AKNTVYLQMS FLKPEDTAIY cam18 A..gins..a ggntyyadav kgRFTISQGN AKNTVFLQMD NLKPEDTAIY cam19 A.aiqvvrsd trltdyadsv kgRFTISQGN TKNTVNLQMN SLTPEDTAIY cam20 A..siyf..q dggtnyrdsv kgRFTISQLN AQNTVYLQMN SLKPEDSAMY cam21 A..vlst..k dgktfyadsv kgRFTIFLDN DKTTFSLQLD RLNPEDTADY cam24 T..aint..d gsviyaadsv kgRFTISQDT AKKTVYLQMN NLQPEDTATY cam25 Sgilsdgtpy tksgdyaesv rgRVTISRDN AKNMIYLQMN DLKPEDTANY cam27 S..sin...i dgkttyadsv kgRFTISQDS AKNTVYLQMN SLKPEDTAMY cam29 S..siy...s dgktyyvdrm kgRFTISREN AKNTLYLQLS GLKPEDTAMY 101                                            139
       m YCARdyygss .......y.. f.....dvWG AGTTVTVSS h YCARXXXXXX xxxxxyyyh x....fdyWG QGTLVTVSS cam1 YCKTalqpgg ycgygx.... ......clWG QGTQVTVSS cam2 YCGAvslmdr isqh...... ......gcRG QGTQVTVSL cam3 YCAAvpahlg pgaildlkky ......kyWG QGTQVTVSS
```

TABLE 1-continued

Comparison af amino acid sequences of various immunoglobulins Alignment of a number of V$_{11}$ regions of Camel heavy chain antibodies compared with those of mouse (M, top line) and human (H, second line). Framework fragments are indicated in capitals, CDR fragments in small print; see SEQ. ID. NO: 13-31 for sequences indicated by M, H, 1, 2, 3, 7, 9, 11, 13, 16, 17, 18, 19, 20, 21, 24, 25, 27, 29, respectively.

```
cam7   YCAAelsggs celpllf... ......dyWG QGTQVTVSS cam9   YCAAdwkywt cgaqtggyf. ......gqWG QGAQVTVSS cam11  YCAArltemg acdarwatla trtfaynyWG QGTQVTVSS cam13  YCAAqkkdrt rwaeprew.. ......nnWG QGTQVTASS cam16  FCAAgsrfss pvgstsrles .sdy..nyWG QGIQVTASS cam17  YCAAadpsiy ysilxiey.. ......kyWG QGTQVTVSS cam18  YCAAdspcym ptmpappird sfgw..ddFG QGTQVTVSS cam19  SCAAtssfyw ycttapy... ......nvWG QGTQVTVSS cam20  YCAIteiewy gcnlrttf.. ......trWG QGTQVTVSS cam21  YCAAnqlagg wyldpnywls vgay..aiWG QGTHVTVSS cam24  YCAArltemg acdarwatla trtfaynyWG RGTQVTVSS cam25  YCAVdgwtrk eggiglpwsv qcedgynyWG QGTQVTVSS cam27  YCXIdsypch ll........ ......dvWG QGTQVTVSS cam29  YCAPveypia dmcs...... ......ryGD PGTQVTVSS
```

For example, according to Pessi et al. (1993) a subdomain portion of a V$_H$ region of common antibodies (containing both heavy chains and light chains) is sufficient to direct its folding, provided that a cognate V$_L$ moiety is present. Thus it might be expected from literature on the common antibodies that without V$_L$ chains proper folding of heavy chains cannot be achieved. A striking difference between the common antibodies and the Camelidae-derived heavy chain antibodies is, that the highly conserved apolar amino acid leucine (L) at place 45 present in common antibodies is replaced in most of the Camelidae-derived heavy chain antibodies by the charged amino acid arginine (R), thereby preventing binding of the variable region of the heavy chain to that of the light chains.

Another remarkable feature is that one of the CDRs of the heavy chains of this type of immunoglobulins from Camelidae. CDR3 is often much longer than the corresponding CDR3 of common heavy chains. Besides the two conserved cysteines forming a disulphide bridge in common V$_H$ fragments, the Camelidae V$_H$ fragments often contain two additional cysteine residues, one of which often is present in CDR3.

According to the present inventors these features indicate that CDR3 may play an important role in the binding of antigens by these heavy chain antibodies and can compensate for the absence of light chains (also containing CDRs) in binding of antigens by immunoglobulins in Camelidae.

Thus, as the heavy chains of Camelidae do not have special features for interacting with corresponding light chains (which are absent), these heavy chains are very different from common heavy chains of immunoglobulins and seem intrinsically more suitable for secretion by prokaryotic and lower eukaryotic cells.

The present inventors realized that these features make both intact heavy chain immunoglobulins of Camelidae and fragments thereof very attractive for their production by microorganisms. The same holds for derivatives thereof including functionalized fragment In this specification the term "functionalized fragment" is used for indicating an antibody or fragment thereof to which one or more functional groups, including enzymes and other binding polypeptides, are attached resulting in fusion products of such antibody fragment with another biofunctional molecule.

SUMMARY OF THE INVENTION

In a broad sense the invention provides a process for the production of an antibody or a fragment or functionalized fragment thereof using a transformed lower eukaryotic host containing an expressible DNA sequence encoding the antibody or (functionalized) fragment thereof, wherein the antibody or (functionalized) fragment thereof is derived from a heavy chain immunoglobulin of Camelidae and is devoid of light chains, and wherein the lower eukaryotic host is a mould or a yeast. Thus the lower eukaryotic host can be a mould, e.g. belonging to the genera *Aspergillus* or *Trichoderma*, or a yeast, preferably belonging to the yeast genera *Saccharomyces, Kluyveromyces, Hansenula,* or *Pichia.* Preferably the fragments still contain the whole variable domain of these heavy chains.

The invention also provides methods to produce such heavy chain immunoglobulins or (functionalized) fragments thereof in which methods the framework or the CDRs of these heavy chains are modified by random or directed mutagenesis in such a way that the mutated heavy chain is optimized for secretion by the host microorganism into the fermentation medium.

Another embodiment of the invention is that CDRs can be grafted on these optimized frameworks (compare grafting of CDRs on human immunoglobulins as described by e.g. Jones et al., Nature 321 (1986) 522). These CDRs can be obtained from common antibodies or they may originate from heavy chain immunoglobulins of Camelidae. The binding properties may be optimized by random or directed mutagenesis. Thus in a process according to the invention an antibody or (functionalized) fragment thereof derived from a heavy chain immunoglobulin of Camelidae can be produced which comprises a CDR different from the CDR belonging to the natural antibody ex Camelidae which is grafted on the framework of the variable domain of the heavy chain immunoglobulin ex Camelidae. The invention also provides a method for the microbiological production of catalytic antibodies. These antibodies are preferably raised in Camelidae against transition state molecules following procedures similar to the one described by Lerner et al., Science 252 (1991) 659-667. Using random or site-directed mutagenesis such catalytic antibodies or fragments thereof can be modified in such a way that the catalytic activity of these (functionalized) antibodies or fragments can be further improved.

For preparing modified heavy chain antibodies a process according to the invention is provided, in which the DNA sequence encodes a modified heavy chain immunoglobulin or a (functionalized) fragment thereof derived from Camelidae and being devoid of light chains, and is made by random or directed mutagenesis or both. Thus the resulting immunoglobulin or (functionalized) fragment thereof is modified such that it is better adapted for production by the host cell, or it is optimized for secretion by the lower eukaryotic host into the fermentation medium, or its binding properties ($k_{on}$ and $k_{off}$) are optimized, or its catalytic activity is improved, or it has acquired a metal chelating activity, or its physical stability is improved.

Another particular embodiment of the present invention relates to genes encoding fusion proteins consisting of both a heavy chain immunoglobulin from Camelidae or part thereof and a second protein or another polypeptide, e.g. an enzyme, in particular an oxido-reductase, and to expression products of such genes. By means of the heavy chain immunoglobulin (fragment) the protein or enzyme can be guided to a target thereby increasing the local efficiency of the protein or enzyme significantly. Thus according to this embodiment of the invention a process is provided, in which the functionalized antibody or fragment thereof comprises a fusion protein of both a heavy chain immunoglobulin from Camelidae or a fragment thereof and another polypeptide, e.g. an enzyme, preferably an oxido-reductase.

As a result of a process according to the invention known products may be produced, e.g. antibodies also produced by Camelidae, but many of the possible products will be new products, thus the invention also provides new products obtainable by a process according to the invention.

The products so produced can be used in compositions for various applications. Therefore, the invention also relates to compositions containing a product produced by a process according to the invention. This holds for both old products and new products.

BRIEF DESCRIPTION OF THE FIGURES

FIGS. 1-4 were already described above in the draft publication.

FIG. 1 Characterisation and purification of camel IgG classes on Protein A, Protein G and gel filtration.

FIG. 2 Repertoire complexity and antigen binding capacity of camel $IgG_1$, $IgG_2$, and $IgG_3$ analysed by radioimmunoprecipitation (A) or Western blotting (B & C).

FIG. 3 Amino acid sequences of the $V_H$ framework, and hinge/$C_H2$ of *Camelus dromedarius* heavy chain immunoglobulins, compared to human (italic) $V_H$ framework (subgroup III) and hinges of human IgG (14): see SEQ. ID. NO: 4-12.

FIG. 4 Schematic representation of the structural organisation of the camel immunoglobulins (adapted from 26).

FIG. 5 DNA and amino acid sequences of the Camel $V_H$ fragments followed by the Flag sequence as present in pB03 (FIG. 5B), pB09 (FIG. 5A) and pB24 (FIG. 5C); see SEQ ID NOs. 34 and 35, 32 and 33, and 36 and 37, respectively.

FIG. 6 Nucleotide sequence of synthetic DNA fragment cloned into pEMBL9 (Example 1) (see SEQ. ID. NO: 38-39) and encoded protein sequences (SEQ ID NO: 40-41). The bottom strand of the DNA restriction fragment, SEQ ID NO: 39, is shown 3' to 5'.

DETAILED DESCRIPTION OF THE INVENTION

Figure 1A:
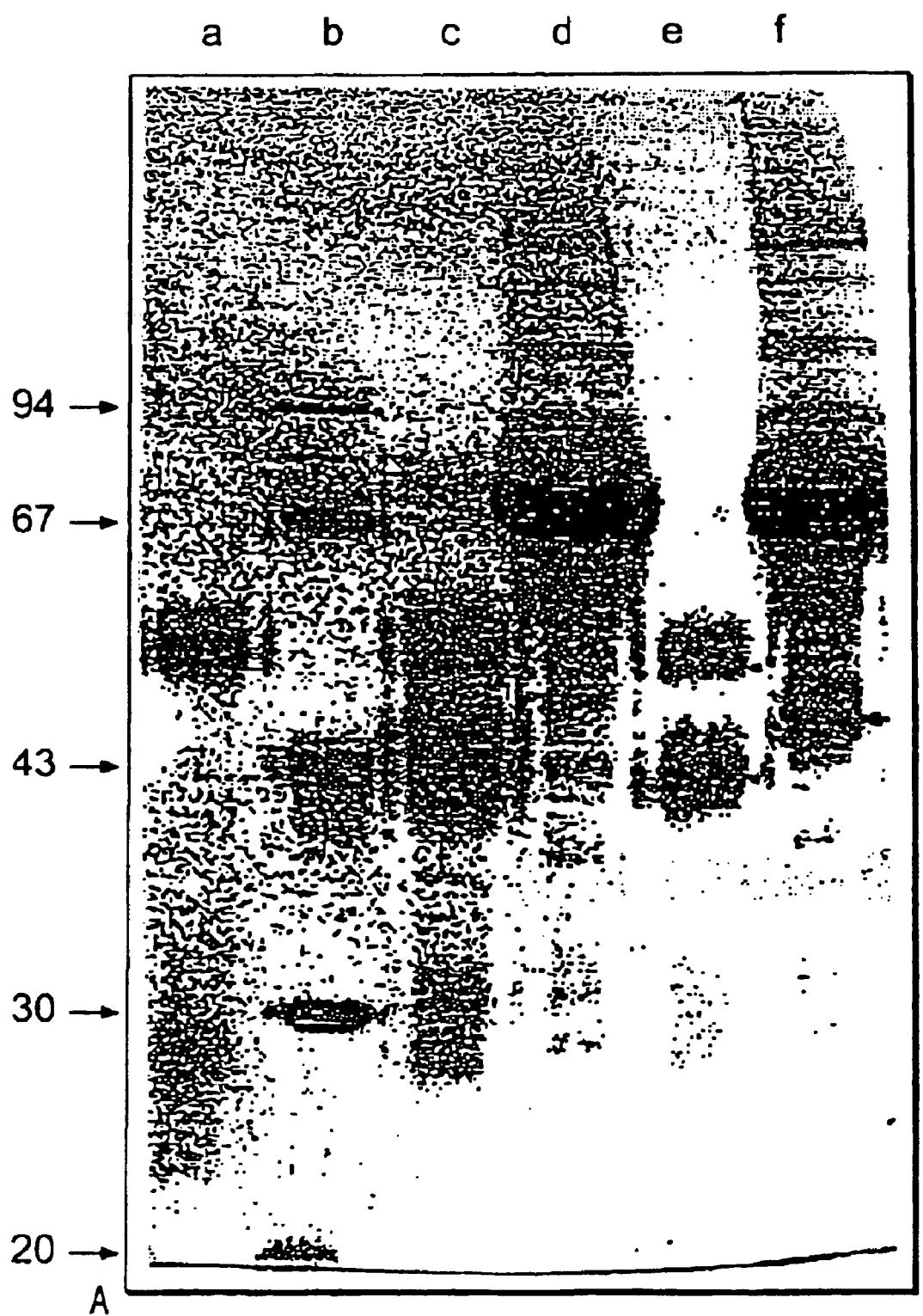
Figure 1B:
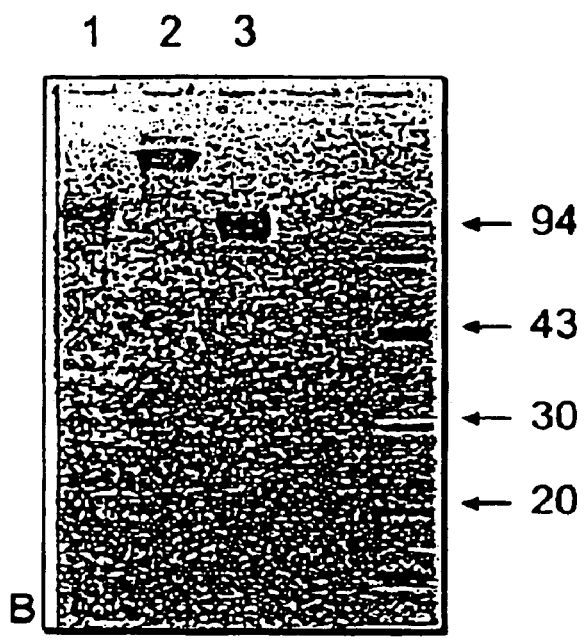
Figure 1C:
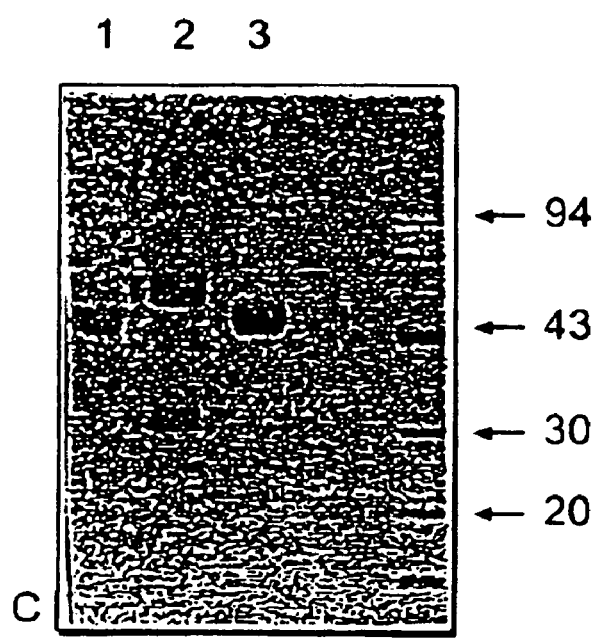
Figure 1D:
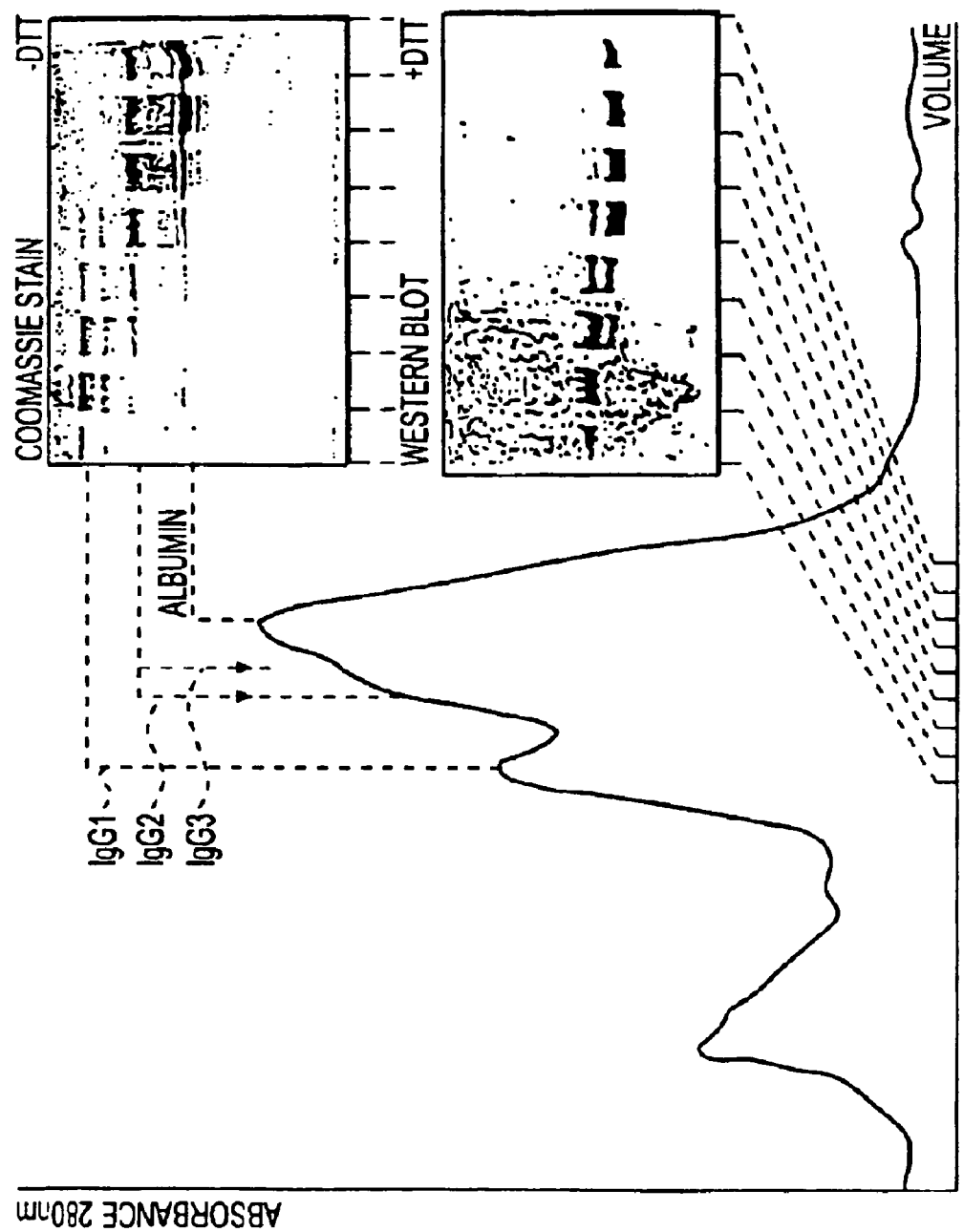
Figure 2A:
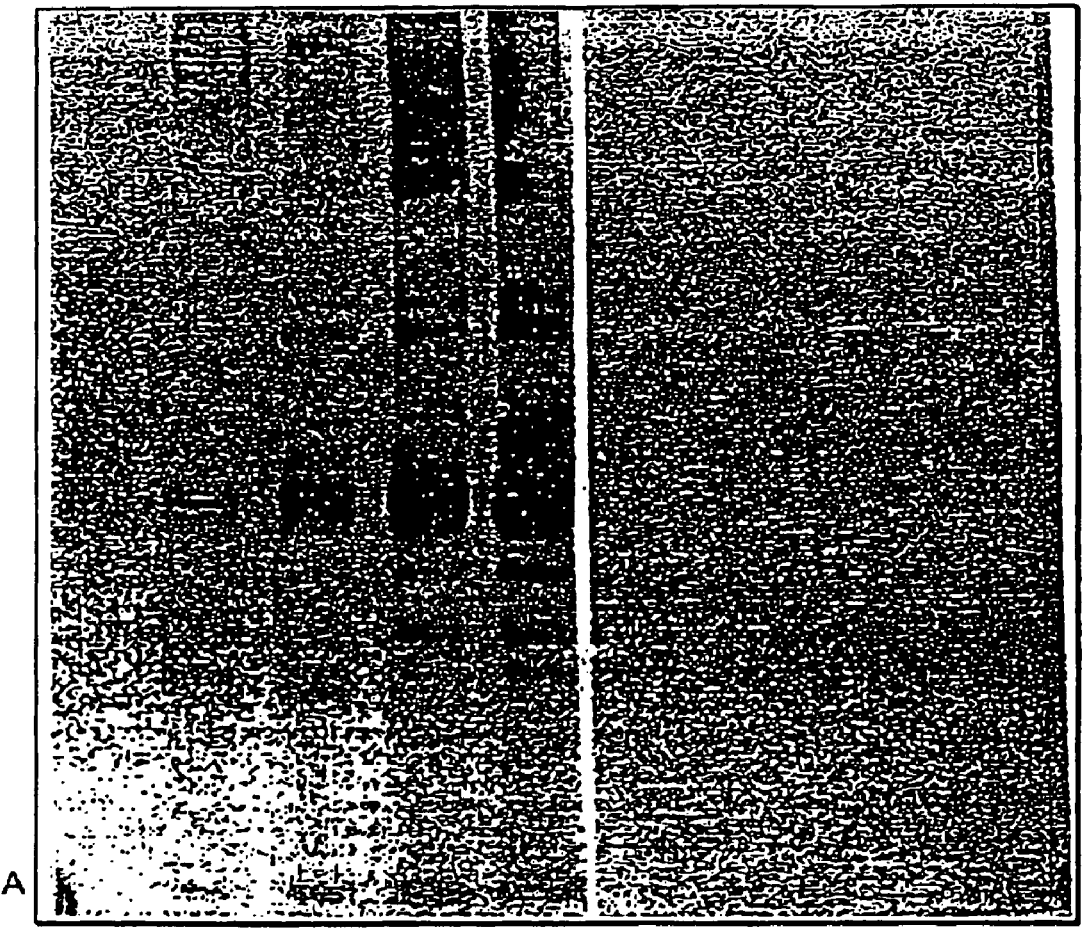
Figures 2B, 2C:
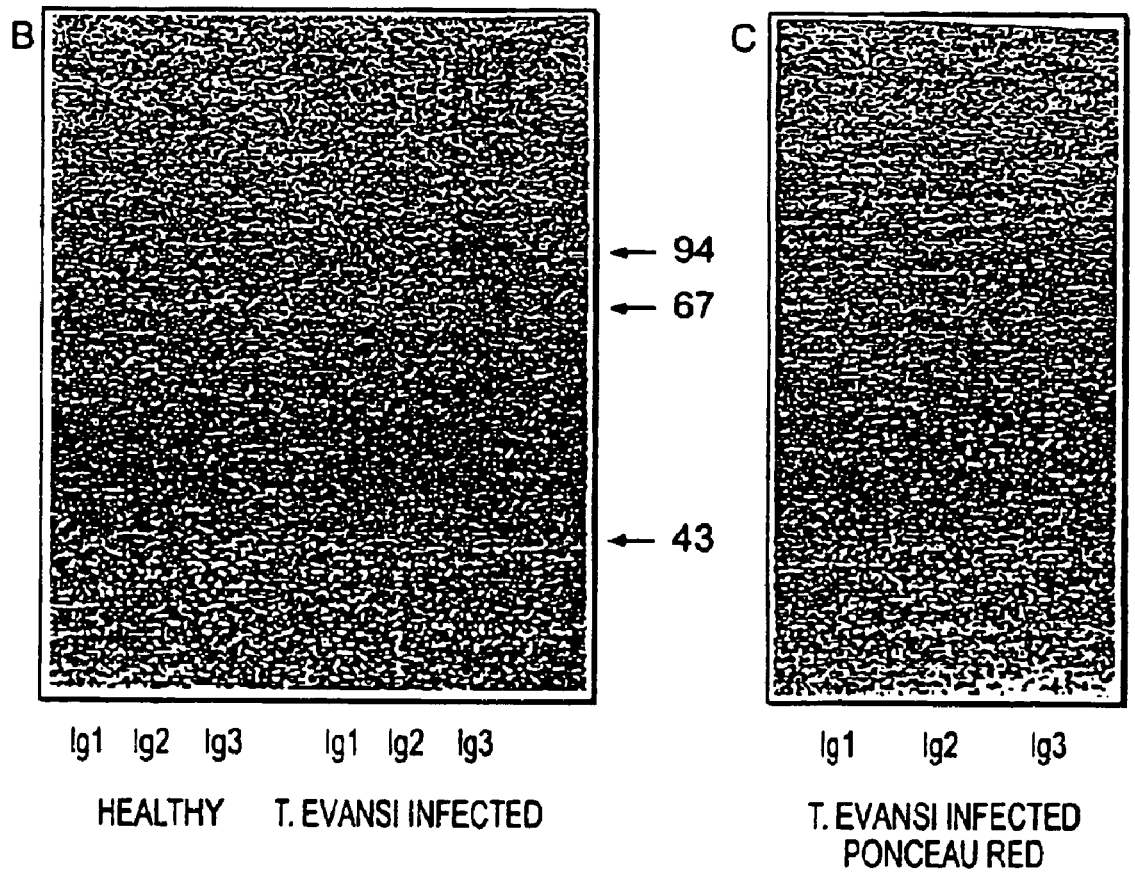

The present invention relates to the production of antibodies or (functionalized) fragments thereof derived from heavy chain immunoglobulins of Camelidae by eukaryotes, more in particular by lower eukaryotes such as yeasts and fungi. Therefore, mRNA encoding immunoglobulins of Camelidae was isolated and transcribed into cDNA according to the procedures described in the above given draft publication and not prior-published European patent application 92402326.0. In each case primers for the PCR reaction directed to the N-terminus of the $V_H$ domain and PCR primers that either hybridize with the C-terminal regions of the $V_H$ domain or with the short or large hinge regions as described in the above given draft publication, or with the C-terminal region of the $C_H2$ or $C_H3$ domains can be used. In this way structural genes can be obtained encoding the following fragments of heavy chain immunoglobulins of Camelidae (Table 2).

TABLE 2

The various forms of immunoglobulins of *Camelidae* that can be expressed in microorganisms.

a. the variable domain of a heavy chain;
b. the variable domain and the short hinge of a heavy chain;
c. the variable domain and the long hinge of a heavy chain;
d. the variable domain, the $C_H2$ domain, and either the short or long hinge of a heavy chain;
e. a complete heavy chain, including either the short or long hinge.

According to procedures described in detail in the Examples these cDNAs can be integrated into expression vectors.

Known expression vectors for *Saccharomyces, Kluyveromyces, Hansenula, Pichia* and *Aspergillus* can be used for incorporating a cDNA or a recombinant DNA according to the invention. The resulting vectors contain the following sequences that are required for expression: (a) a constitutive, or preferably an inducible, promoter; (b) a leader or signal sequence; (c) one of the structural genes as described in Table 2 and (d) a terminator. It the vector is an episomal vector, it preferably comprises an origin of replication as well as a selection marker, preferably a food grade selection marker, (EP-A487159, UNILEVER/Leenhouts et al.). If the vector is an integration vector, then it preferably comprises sequences that ensure integration and a selection marker in addition to the sequences required for expression of the structural gene encoding a form of the heavy chain immunoglobulin of Camelidae or derivatives thereof. The preferred sequences for integration are sequences encoding ribosomal DNA (WO 91/00920, 1991. UNILEVER/Giuseppin et al.) whereas the selection marker will be preferably a food grade marker.

For *Saccharomyces* the preferred inducible promoter is the GAL7 promoter (EP-A-0255153, UNILEVER/Fellinger et al.); for Kluyveromyces the preferred inducible promoter is the inulinase promoter (not yet published EP application 92203932.6, UNILEVER/Toschka & Verbakel, which is incorporated herein by reference); for *Hansenula* or *Pichia* the preferred inducible promoter is the methanol-oxidase promoter (Sierkstra et al., Current Genetics 19 (1991) 81-87) and for *Aspergillus* the preferred inducible promoter is the endoxylanase promoter (not prior-published PCT application PCT/EP 92/02896, UNILEVER/Gouka et al, now publicly available as WO-A-93/12237, which is incorporated herein by reference). To achieve efficient secretion of the heavy chain immunoglobulin or parts thereof the leader (secretion) sequences of the following proteins are preferred: invertase and α-factor for *Saccharomyces*, inulinase for *Kluyveromyces*, invertase for *Hansenula* or *Pichia* (Sierkstra et al., 1991 supra) and either glucoamylase or xylanase for *Aspergillus* (not prior-published PCT application WO-A-93/12237, supra). As food-grade selection markers, genes encoding anabolic functions like the leucine2 and tryptophan3 are preferred (Giuseppin et al. 1991, supra). The present invention describes the heterologous production of (functionalized) derivatives or fragments of immunoglobulins in a microorganism, which immunoglobulins in nature occur not as a composite of heavy chains and light chains, but only as a composite of heavy chains. Although the secretion mechanism of mammals and microorganisms is quite similar, in details there are differences that are important for developing industrial processes.

To obtain frameworks of the heavy chain immunoglobulins, that are optimally secreted by lower eukaryotes, genes encoding several different heavy chains can be cloned into the coat protein of bacteriophages and subsequently the frameworks of these heavy chain immunoglobulins can be mutated using known PCR technology, e.g. Zhou et al., (1991). Subsequently the mutated genes can be been cloned in *Saccharomyces* and *Aspergillus* and the secretion of the mutated genes can be compared with the wild type genes. In this way frameworks optimized for secretion may be selected.

Alternatively these structural genes can be linked to the cell wall anchoring part of cell wall proteins, preferably GPI-linked cell wall proteins of lower eukaryotes, which result in the expression of a chimeric protein on the cell wall of these lower eukaryotes (not prior-published EP application 922020805, UNILEVER/Klis et al., now publicly available as International (PCT) patent application WO-A-94/01567, which is incorporated herein by reference).

Both methods have the advantage that the binding parts of the immunoglobulins are well exposed to the surrounding of the cell, microorganism, or phage and therefore can bind antigens optimally. By changing the external conditions the binding rates and dissociation rates of this binding reaction can be influenced. Therefore, these systems are very suitable to select for mutated immunoglobulins that have different binding properties. The mutation of the immunoglobulins can either be obtained by random mutagenesis, or directed mutagenesis based on extensive molecular modelling and molecular dynamical studies.

mRNAs encoding heavy chains of immunoglobulins raised in Camelidae against transition state molecules (Lerner et al., 1991 supra) can be obtained using standard techniques. The structural genes encoding various forms of immunoglobulins according to the invention as summarized in Table 2 can be cloned into the coat protein of bacteriophages or its fusion with the anchoring part of cell wall proteins and can be tested on the catalytic property. In this way immunoglobulins or parts thereof having catalytic properties can be determined and selected. Genes encoding these selected immunoglobulins or parts thereof can be mutated as described before and recloned in bacteriophages, but preferably cloned as chimeric cell wall bound catalysts in lower eukaryotes. By performing appropriate catalytic assays, catalytic immunoglobulins or parts thereof with improved catalytic properties can be determined and selected using standard techniques.

An important application of antibodies, especially outside the pharmaceutical industry, will be chimeric proteins consisting of the binding part of antibodies and enzymes. In this way catalytic biomolecules can be designed that have two binding properties, one of the enzyme and the other of the antibody. This can result in enzymes that have superior activity. This can be illustrated with the following examples:

a. If the substrate of the enzymic reaction is produced by an organism or an enzyme is recognized by the binding domain of the antibody, the local concentration of the substrate will be much higher than for enzymes lacking this binding domain and consequently the enzymic reaction will be improved. In fact this is a mimic of vectorial metabolism in cells (compare e.g. Mitchell, (1979) Science 206 1148-1159);

b. If the substrate of the enzymic reaction is converted into a molecule that kills organisms, then the efficiency and specificity of killing can be increased significantly if the enzyme is equipped with an antibody binding domain that recognizes the target organism (e.g. compare Takahashi et al., (1993) Science 259 1460-1463);

The invention will be illustrated by the following Examples without being limited thereto. In previously filed Unilever patent specifications several expression vectors were described, e.g. for the yeasts *S. cerevisiae, Kluyveromyces*, and *Hansenula*, and the mould *Aspergillus*. Examples of these publications are EP-A-0173378 (UNILEVER/Ledeboer et al.), EP-A-0255153, supra, and PCT applications WO-A-91/19782 (UNILEVER/van Gorcom et al.) and (not prior-published) WO-A-93/12237, supra. The genes encoding antibodies or (functionalized) fragments thereof according to the invention can be incorporated into the earlier described expression vectors or derivatives thereof using procedures well known to a skilled person in the art. All techniques used for the manipulation and analysis of nucleic acid materials were performed essentially as described in Sambrook et al (1989) (see also ref. 23 of the above given draft publication), except where indicated otherwise.

In the description of the Examples the following endonuclease restriction sites are used:

```
AflII     C↓TTAAG     MluI     A↓CGCGT

BspHI     T↓CATGA     NcoI     C↓CATGG

BspHI     T↓CATGA     Not      GC↓GGCCGC

BstEII    G↓GTNACC    NruI     TCG↓CGA

EagI      C↓GGCCG     SalI     G↓TCGAC

EcoRI     G↓AATTC     XhoI     C↓TCGAG

HindIII   A↓AGCTT     BbsI     GAAGAC(N)₂↓
                               CTTCTG(N')₆↓
```

Example 1

Construction of Cassettes Encoding $V_H$ Fragments Originating from Camelidae

For the production of $V_H$ fragments originating from Camelidae, the antibody gene fragments were isolated and cloned as described above in the draft publication. The thus obtained gene fragments encode the $V_H$ region, a short or a long hinge region and about 14 amino acids of the $C_H2$ region. By using standard molecular biological techniques (e.g. PCR technology), the $V_H$ gene fragments could be subcloned and equipped at their 5'-ends with a gene fragment encoding the pelB signal sequence and at their 3'-ends with a gene fragment encoding the Flag tail (13 amino acids). Three of these clones were named pB3, pB9 and pB24 and were deposited at the Centraal Bureau voor Schimmelcultures, Baarn on 20 Apr. 1993 with deposition numbers: CBS 270.93, CBS 271.93 and CBS 272.93, respectively. The DNA and amino acid sequences of the Camelidae-$V_H$ fragments followed by the Flag sequence are presented in FIG. 5(A-C); see SEQ. ID. NO: 32-37.

1.1 Construction of pUR4421

For the construction of yeast expression plasmids encoding the $V_H$ fragments preceded by the invertase (=SUC2) signal sequence, the α-mating factor prepro-sequence, or the inulinase signal sequence and followed by either nothing, or a Myc tail or Flag tail, the constructs described below can be prepared.

The multiple cloning site of plasmid pEMBL9 (Denthe et al., 1983) (ranging from the EcoRI to the HindIII site) was replaced by a synthetic DNA fragment having the nucleotide sequence as indicated in FIG. 6; see SEQ. ID. NO: 38-41. The 5'-part of this nucleotide sequence comprises an EagI site, the first 4 codons of the Camelidae $V_H$ gene fragment and a XhoI site coinciding with codons 5 and 6. The 3'-part comprises the last 5 colons of the Camelidae $V_H$ gene (encoding VTVSS; see SEQ. ID. NO: 47) part (if which coincides partially with a BstEII site), eleven codons of the Myc tail, and an EcoRI site. The EcoRI site, originally present in pEMBL9, is not functional any more, because the 5'-end of the nucleotide sequence contains AATTT instead of AATTC, indicated in FIG. 6 as "(EcoRI)". The resulting plasmid is called pUR4421.

1.2 Constructs with Flag Tail.

After digesting the plasmid pB3 with XhoI and EcoRI, a DNA fragment of approximately 425 bp was isolated from agarose gel. This fragment codes for a truncated $V_H$-Flag fragment, missing the first 5 amino acids of the Camelidae $V_H$. The obtained fragment can be cloned into pUR4421. To this end plasmid pUR4421 can be digested with XhoI and EcoRI, after which the about 4 kb vector fragment can be isolated from an agarose gel. Ligation with the about 425 bp fragment will result in plasmid pUR4421-03F.

1.3 Constructs with Myc Tail.

After digesting the plasmid pB3 with XhoI and BstEII, a DNA fragment of approximately 365 bp was isolated from agarose gel. This fragment codes for a truncated $V_H$ fragment, missing both the first 4 (QVKL; see SEQ. ID. NO: 46) and the last 5 (VTVSS; see SEQ. ID. NO: 47) amino acids of the Camelidae $V_H$ fragment.

The obtained fragment was cloned into pUR4421. To this end plasmid pUR4421 was digested with XhoI and BstEII, after which the about 4 kb vector fragment was isolated from an agarose gel. Ligation with the about 365 bp fragment resulted in plasmid pUR4421-03M, in which the gene encoding the $V_H$ fragment is reconstituted.

1.4 Constructs Encoding $V_H$ Only.

Upon digesting pUR4421-03M or pUR4421-03F with BstEII and HindIII, the vector fragments of about 4.4 kb can be isolated from agarose gel and religated in the presence of a synthetic linker peptide having the following sequence:

```
BstEII                HindIII
GTCACCGTCTCCTCATAATGA        (top strand, SEQ ID
    GCAGAGGAGTATTACTTCGA.     NO: 48, is shown
                              5' to 3';
                              bottom strand, SEQ
                              ID NO: 49, is
                              shown 3' to 5'
``` plasmid, pUR4421-03, the Myc tail or Flag tail sequences are removed and the $V_H$ gene fragment is directly followed by a stop codon.

1.5 Other Constructs.

After isolating the gene fragments encoding $V_H$-hinge-$C_H2$ fragments as described above in the draft publication, or encoding the intact heavy chain immunoglobulin, it is possible, e.g. by using PCR technology, to introduce an appropriate restriction enzyme recognition site (e.g. EcoRI or HindIII) downstream of the hinge region, downstream of the $C_H2$ region, or downstream of the total gene. Upon isolating a XhoI-EcoRI or XhoI-HindIII fragment encoding the Via fragment with a C-terminal extension, the fragment can be cloned into pUR4421 digested with the same restriction enzymes.

In analogy with the construction of pUR4421-03, a number of other constructs can be produced encoding functionalized heavy chain fragments in which a second polypeptide is fused to the C-terminal part of the Vat fragment. Optionally, the $V_H$ fragment and the second polypeptide, e.g. an enzyme, might be connected to each other by a peptide linker.

To this end either the BstEII-HindIII fragment or the BstEII-EcoRI fragment of either pUR4421-03F or pUR4421-03M has to be replaced by another BstEII-HindIII or BstEII-EcoRI fragment. The latter new fragment should code for the last amino acids (VTVSS, see SEQ. ID. NO: 47) of the $V_H$ fragment, optionally for a linker peptide, and for the polypeptide of interest e.g. an enzyme. Obviously, the introduction of the DNA fragment should result in an in frame fusion between the $V_H$ gene fragment and the other DNA sequence encoding the polypeptide of interest.

Alternatively, it is possible to replace the EagI-XhoI fragment of pUR4421-03 with another DNA fragment, coding for a polypeptide of interest, optionally for a peptide linker, and for the first 4 (QVKL, see SEQ. ID. NO: 46) amino acids of the $V_H$ fragment, resulting in an in frame fusion with the remaining part of the $V_H$ fragment. In this way, it is possible to construct genes encoding functionalized $V_H$ fragments in which the second polypeptide is fused at the N-terminal part of the $V_H$ fragment, optionally via a peptide linker.

Obviously, it is also possible to construct genes encoding functionalized $V_H$ fragments having a polypeptide fused to the N-terminal as well as fused to the C-terminal end, by combining the above described construction routes. The polypeptides used to functionalize the $V_H$ fragments might be small, like the Myc and the Flag tails, or intact enzymes, like glucose oxidase, or both.

From all the above described constructs, derived from pUR4421, an appropriate EagI-HindIII fragment, encoding the functionalized $V_H$ fragment, can be isolated and cloned into a number of different expression plasmids. Several are exemplified in more detail in the following Examples. Although only the $V_H$ fragments are exemplified, similar constructs can be prepared for the production of larger heavy chain fragments (e.g. $V_H$-hinge or $V_H$-hinge-$C_H2$) or intact heavy chains. The EagI site is introduced before the first codon of the $V_H$ fragment, facilitating an in frame fusion with different yeast signal sequences.

In particular cases, were additional EagI and/or HindIII sites are present in the cloned fragments, it is necessary to perform partial digestions with one or both restriction enzymes.

Although the above and following constructions only consider the $V_H$ fragment cloned in pB3, a comparable construction route can be used for the construction of expression plasmids for the production of $V_H$ fragments like $V_H$-09 and $V_H$-24, or other $V_H$ fragments.

Example 2

Construction of S. cerevisiae Episomal Expression Plasmids for Camelidae $V_H$

For the secretion of recombinant protein from S. cerevisiae it is worthwhile to test in parallel the two most frequently applied homologous signal sequences, the SUC2 invertase signal sequence and the prepro-α mating factor sequence.

The episomal plasmid pSY1 and pSY16 (Harmsen et al., 1993) contain expression cassettes for the α-galactosidase gene. Both plasmids contain the GAL7 promoter and PGK terminator sequences. pSY1 contains the invertase (SUC2) signal sequence and pSY16 contains a slightly modified (Harmsen et al., 1993) prepro-α-mating factor signal sequence.

Both plasmids, pSY1 and pSY16 can be digested with EagI and HindIII, the about 6500 bp long vector backbone of both plasmids can be isolated and subsequently ligated with the EagI/HindIII fragments from pUR4421-03F (−465 bp), pUR4421-03M (⁻455 bp) or pUR4421-03 (⁻405 bp) (See above).

Figure 7:
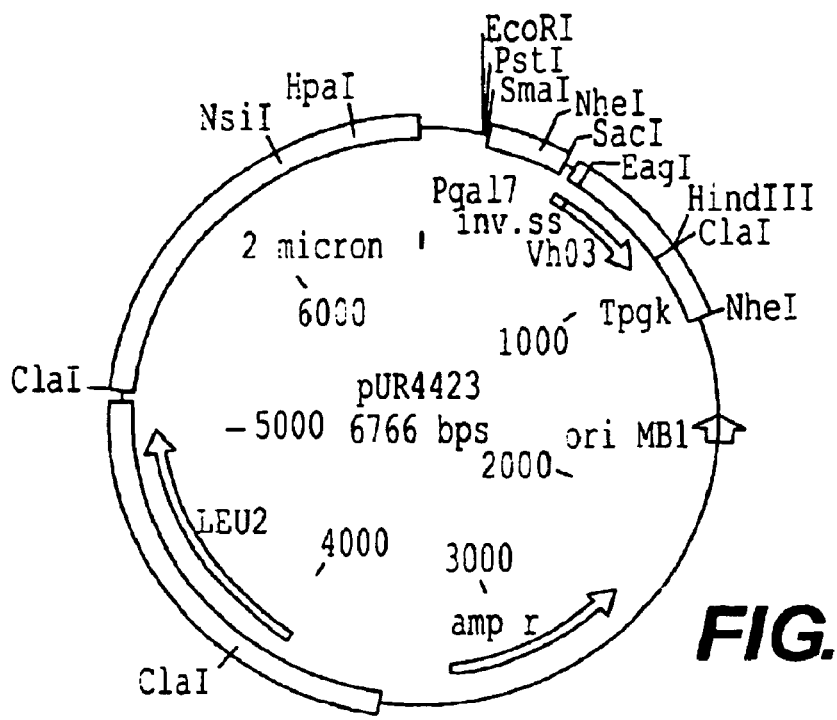
FIG. 7 Schematic drawing of plasmid pUR4423
FIG. 8 Schematic drawing of plasmid pUR4426
FIG. 9 Schematic drawing of plasmid pUR2778
FIG. 10 Schematic drawing of plasmid pUR4429
FIG. 11 Schematic drawing of plasmid pUR4430
FIG. 12 Schematic drawing of plasmid pUR4445
FIG. 13 Schematic drawing of plasmid pUR4446
FIG. 14 Schematic drawing of plasmid pUR4447
FIG. 15 Schematic drawing of plasmid pUR4451
FIG. 16 Schematic drawing of plasmid pUR4453
FIG. 17 Schematic drawings of plasmids pUR4437 and pUR4438
FIG. 18 Schematic drawings of plasmids pUR4439 and pUR4440
FIG. 19 Nucleotide sequence of synthetic DNA fragment cloned into pEMBL9 (Example 6) (see SEQ. ID. NO: 42-43) and encoded protein sequences (SEQ ID NO: 44-45). The bottom strand of the DNA restriction fragment, SEQ ID NO: 43, is shown 3' to 5'.
Figure 8:
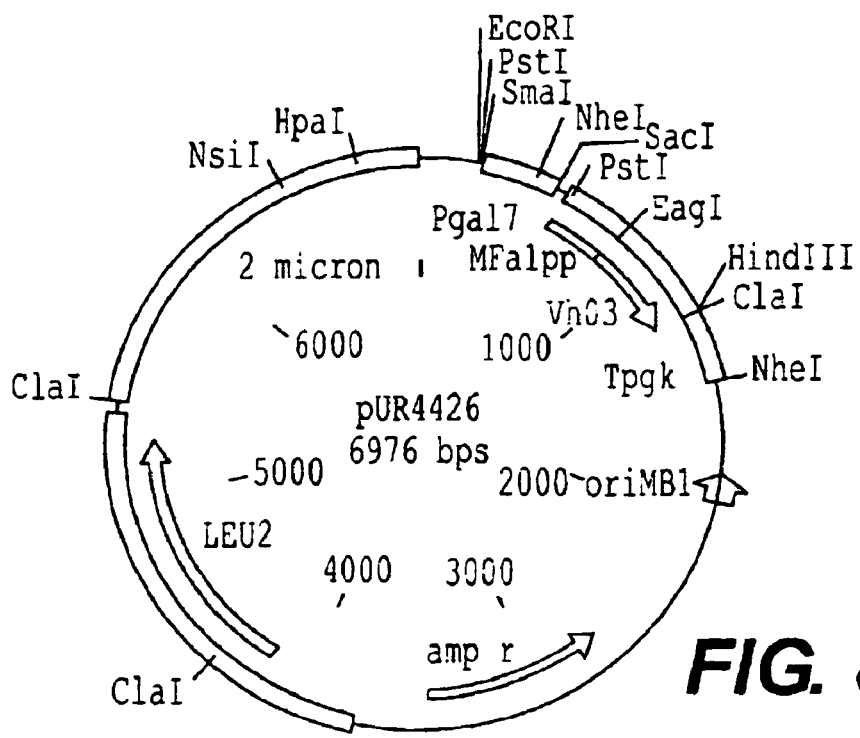

This results in a series of 6 different episomal plasmids for expression in S. cerevisiae, containing behind the SUC2- and the a mating factor prepro-sequence the $V_H$-Flag coding sequence (designated pUR4423F and pUR4426F), the $V_H$-Myc coding sequence (designated pUR4423M and pUR4426M) or the coding sequence of $V_H$ followed by a stop codon (designated pUR4423, FIG. 7 and pUR4426, FIG. 8).

Obviously, it is possible to use promoter systems different from the inducible GAL7 promoter, e.g. the constitutive GAPDH promoter.

2.1 Production of $V_H$-03-myc and $V_H$-24-myc.

After introducing the expression plasmids pUR4423M (coding for $V_H$-03-myc, preceded by the SUC2-signal sequence) and pUR4425M (coding for $V_H$-24-myc, preceded by the SUC2-signal sequence) into S. cerevisiae via electroporation, transformants were selected from minimal medium agar plates (comprising 0.7% yeast nitrogen base, 2% glucose and 2% agar, supplemented with the essential amino acids and bases).

Figure 21:
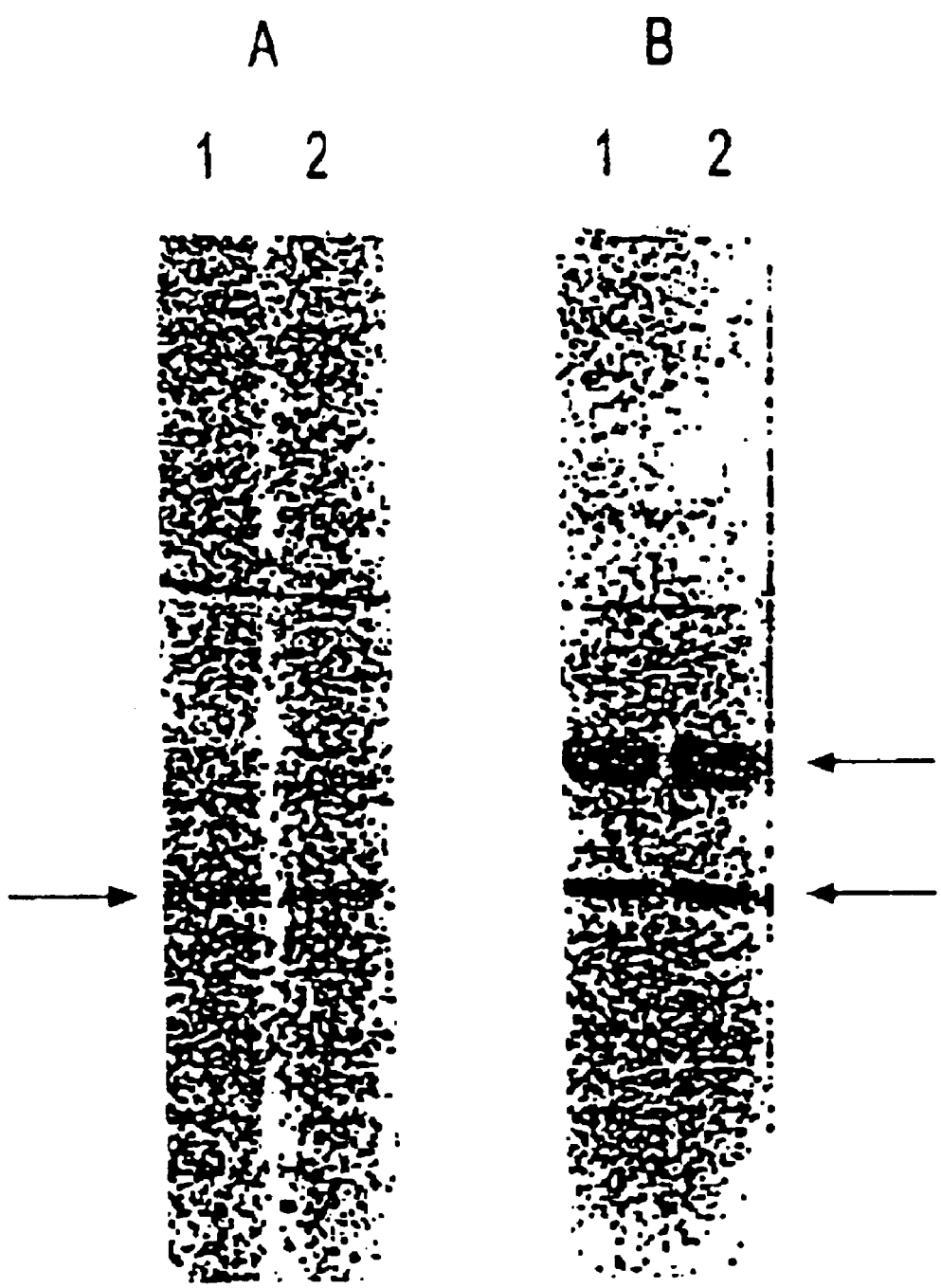
FIG. 21 Western blot analysis of culture medium of *S. cerevisiae* transformants containing pUR4423M (see A) or pUR4425M (see B). Samples were taken after 24 (see 1) or 48 hours (see 2). For pUR4425M two hands were found due to glycosylation of the antibody fragment.

For the production of antibody fragments the transformants were grown overnight in selective minimal medium (comprising 0.7% yeast nitrogen base, 2% glucose, supplemented with the essential amino acids and bases) and subsequently diluted ten times in YPGal medium (comprising 1% yeast extract, 2% bacto pepton and 5% galactose). After 24 and 48 hours of growth, samples were taken for Western blot analysis (FIG. 21). For the immuno detection of the produced $V_H$-myc fragments monoclonal anti-myc antibodies were used.

In essentially the same way comparable results were obtained with a yeast transformed with pUR4424M containing a DNA sequence encoding the $V_H$-09-myc protein.

Example 3

Construction of S. cerevisiae Multicopy Integration Vectors for the Expression of Camelidae $V_H$ To combine the benefits of high copy number and mitotically stable expression, the concept of a multicopy integration system into the rDNA locus of lower eukaryotes has already been successfully proven (Giuseppin et al supra).

Figure 9:
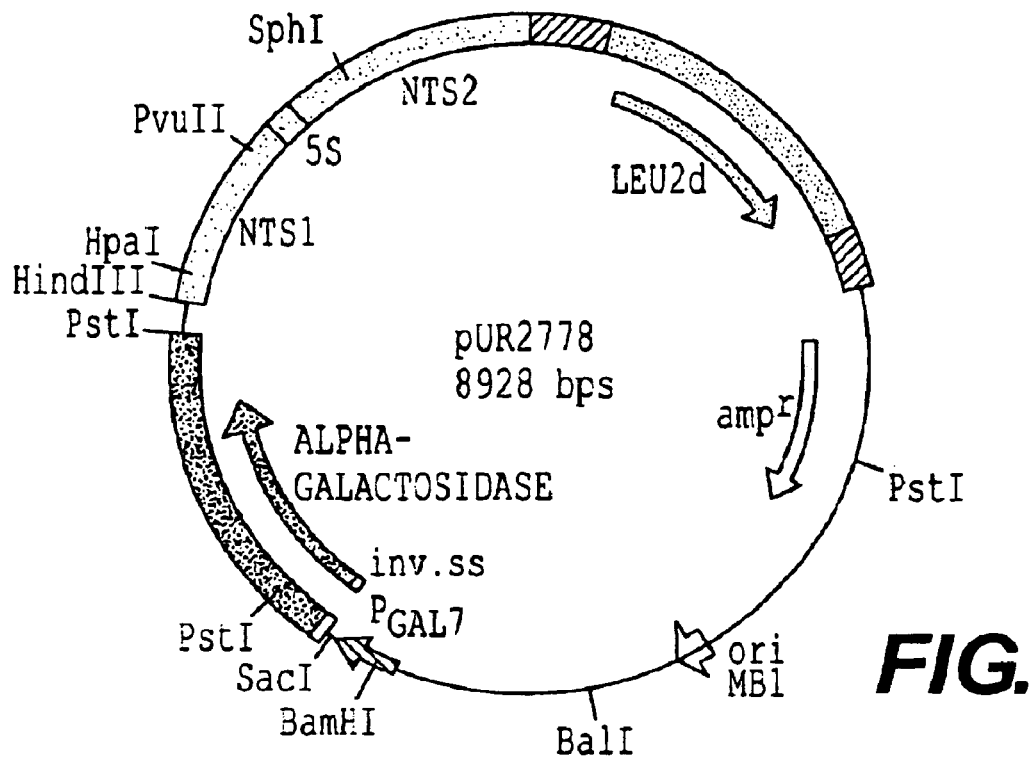

One of these vectors is pUR2778, a derivative of pUR2774 (Giuseppin et at supra) from which the poll-S.O. reporter gene sequence was removed (FIG. 9). This integrating plasmid, pUR2778, can be used for integration of Camelidae $V_H$ coding sequences, hence the vector can be digested with SacI and HindIII after which the ⁻73 kb vector fragment can be isolated.

From the in example 2 described pUR4423 or pUR4426 types of plasmids, SacI-HindIII fragments can be isolated encoding a $V_H$ fragment preceded by a signal sequence (SUC2 or a mating factor prepro) and followed by nothing or a Myc or Flag tail.

Ligation of these SacI-HindIII fragments with the 73 kb vector fragment will result in integration plasmids, encoding the (functionalized) $V_H$ fragments under the regulation of the strong and inducible GAL7 promoter.

In this way the following expression plasmids were obtained:

| pUR4429 | $P_{gal7}$ - SUC2 sig.seq. - $V_H$-03 |
| pUR4429F | $P_{gal7}$ - SUC2 sig.seq. - $V_H$-03 - Flag tail |
| pUR4429M | $P_{gal7}$ - SUC2 sig.seq. - $V_H$-03 - Myc tail |
| pUR4430 | $P_{gal7}$ - α mat.fac. prepro. - $V_H$-03 |
| pUR4430F | $P_{gal7}$ - α mat.fac. prepro. - $V_H$-03 - Flag tail |
| pUR4430M | $P_{gal7}$ - α mat.fac. prepro. - $V_H$-03 - Myc tail |

Figure 10:
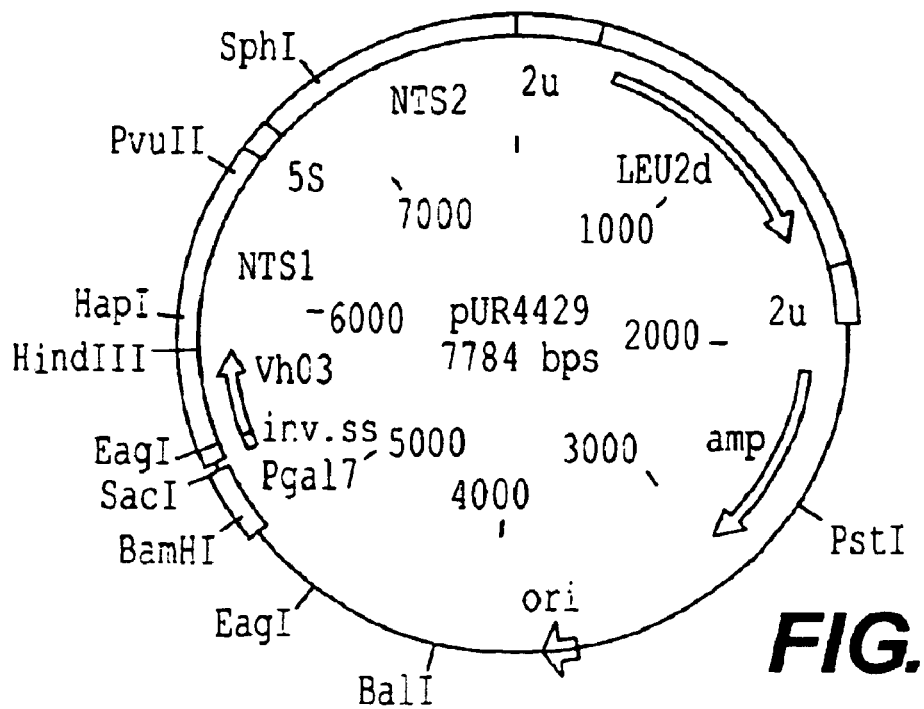
Figure 11:
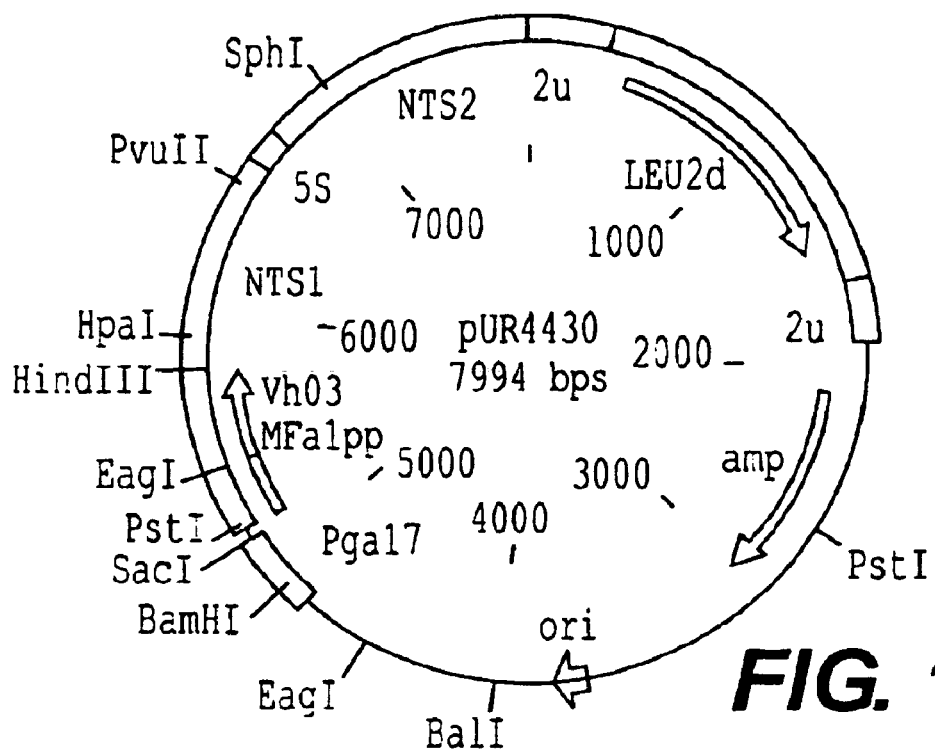

For schematic drawings see FIG. 10 for pUR4429 and FIG. 11 for pUR4430. Obviously, comparable constructs can be prepared for other heavy chain antibodies or fragments thereof.

As mentioned before, different promoters might be used, for example, the constitutive GAPDH promoter.

Example 4

Construction of Expression Plasmids for the Production of (Functionalized) $V_H$ Fragments from Camelidae by Kluyveromyces 4.1. Construction of *Kluyveromyces lactis* Episomal Expression Plasmids Camelidae.

Yeast strains of the genus Kluyveromyces have been used for the production of enzymes, such as β-galactosidase for many years, and the growth of the strains has been extensively studied. *Kluyveromyces lactis* is well known for the ability to utilize a large variety of compounds as carbon and energy sources for growth. Since these strains are able to grow at high temperatures and exhibit high growth rates, they are promising hosts for industrial production of heterologous proteins (Hollenberg, C. et al., EP-A-0096430, GIST-BROCADES N.V., 1983).

The plasmids pUR2427 and pUR2428 are pTZ19R derivatives with the promoter and the DNA sequence encoding either the signal peptide (=pre-sequence) (in pUR2428), or the natural prepro-sequence (in pUR2427), of inulinase (inu) from *Kluyveromyces marxiamus*. Both plasmids contain a unique BspMI site suitable to create a perfect joint with EagI or NotI digested DNA-fragments (not yet published European patent application 92203932.6, (supra). In both plasmids a unique HindIII site is located a bit further downstream of the BspMI-site, so that EagI-HindIII cut DNA-fragments encoding $V_H$ from Camelidae either solely or with Myc- or Flag-tail can be easily ligated into BspMI-HindIII digested pUR2427 or pUR2428. Thereby a set of six plasmids can be created containing the promoter and secretion signals of the *Kluyveromyces marxiamus* inulinase gene, joint in frame to Camelidae Vh encoding sequences, all on a EcoRI-HindIII restriction fragment:

| pUR4445 | $P_{inu}$ - Inu prepro seq. - $V_H$ - 03 |
| pUR4445M | $P_{inu}$ - Inu prepro seq. - $V_H$ - 03 - Myc |
| pUR4445F | $P_{inu}$ - Inu prepro seq. - $V_H$ - 03 - Flag |
| pUR4446 | $P_{inu}$ - Inu pre seq. - $V_H$ - 03 |
| pUR4446M | $P_{inu}$ - Inu pre seq. - $V_H$ - 03 - Myc |
| pUR4446F | $P_{inu}$ - Inu pre seq. - $V_H$ - 03 - Flag. |

Figure 12:
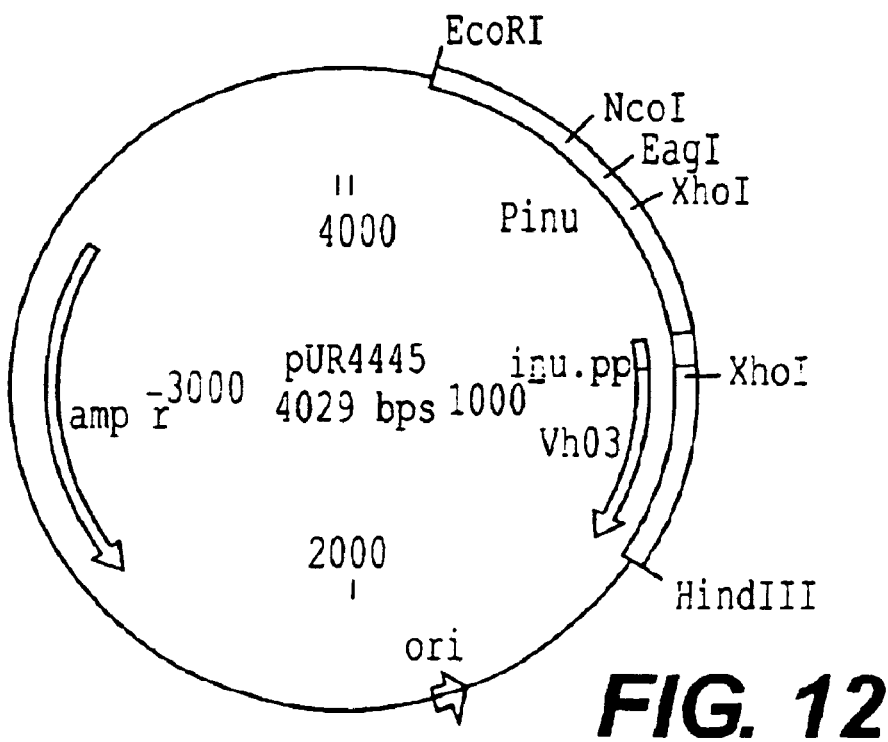
Figure 13:
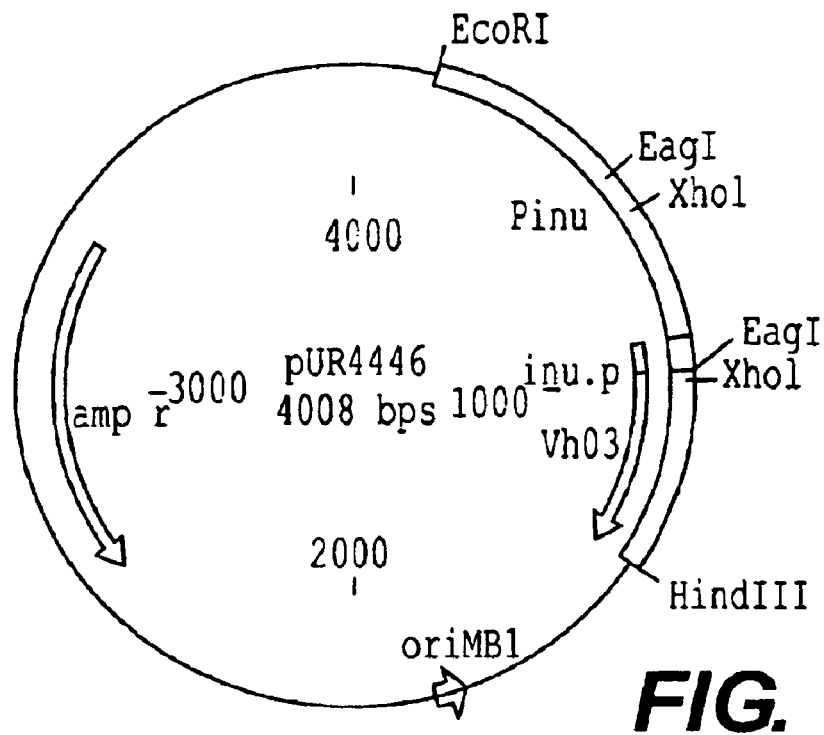

Maps of pUR4445 and pUR4446 are shown in FIG. 12 and FIG. 13.

The EcoRI-HindIII fragments of these plasmids can be ligated into the expression vector pSK1 (not yet published European patent application 92203932.6, supra), from which the α-galactosidase expression cassette including the GAL7-promoter is removed with a EcoRI(partial) and HindIII digestion. The resulting plasmids can then be transformed, for example in *K. lactis* strain MSK110 (a, uraA, trp1::URA3), as they contain the trp1 marker and the pKD1 episomal plasmid sequences:

| pUR4447 | $P_{inu}$ - Inu prepro seq. - $V_H$ - 03 |
| pUR4447M | $P_{inu}$ - Inu prepro seq. - $V_H$ - 03 - Myc |
| pUR4447F | $P_{inu}$ - Inu prepro seq. - $V_H$ - 03 - Flag |
| pUR4448 | $P_{inu}$ - Inu pre seq. - $V_H$ - 03 |
| pUR4448M | $P_{inu}$ - Inu pre seq. - $V_H$ - 03 - Myc |
| pUR4448F | $P_{inu}$ - Inu pre seq. - $V_H$ - 03 - Flag. |

Figure 14:
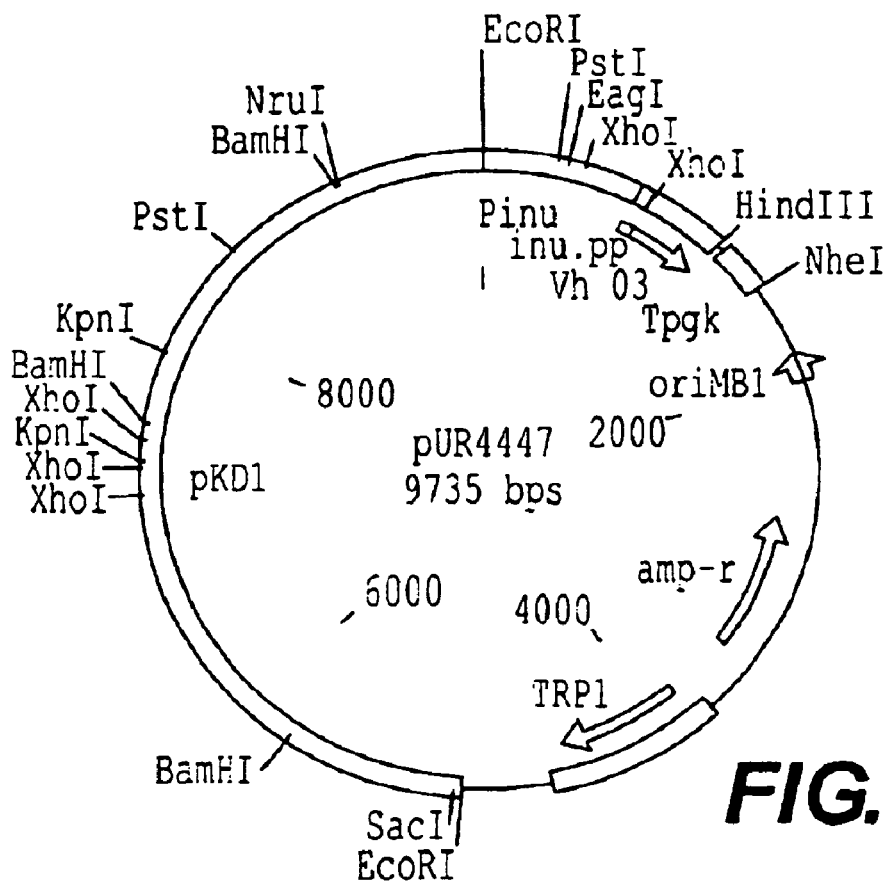

A map of pUR4447 is shown in FIG. 14.

Transformation can be performed standard techniques such as the methods of Beggs (1978) or electroporation, using 0.67% Yeast Nitrogen Base (without amino acids) and 2% glucose as the selection medium for transformants.

4.2. Construction of *Kluyveromyces lactis* Multicopy Integration Vectors.

Alternatively, since all tailed and non-tailed versions of the $V_H$ fragments, joined to the inulinase promoter and secretion signals, are located on EcoRI-HindIII fragments, the rDNA multicopy integration plasmid pMIRKGAL-TΔ1 (Bergkamp et al., 1992) can be used in a similar way as the pSK1 plasmid. In order to replace the α-gal expression cassette present in this plasmid, by a antibody fragment cassette, these plasmids have to be digested with EcoRI(partial) and HindIII. After isolating the vector fragments, they can be ligated with the about 1.2 kb EcoRI-HindIII fragments which can be obtained from the plasmids described in example 4.1. The resulting plasmids can be linearized with SacII and transformed to MSK110, resulting in *K. lactis* strains with potentially high and stable expression of single chain $V_H$ fragments.

| pUR4449 | $P_{inu}$ - Inu prepro seq. - $V_H$ - 03 |
| pUR4449M | $P_{inu}$ - Inu prepro seq. - $V_H$ - 03 - Myc |
| pUR4449F | $P_{inu}$ - Inu prepro seq. - $V_H$ - 03 - Flag |
| pUR4450 | $P_{inu}$ - Inu pre seq. - $V_H$ - 03 |
| pUR4450M | $P_{inu}$ - Inu pre seq. - $V_H$ - 03 - Myc |
| pUR4450F | $P_{inu}$ - Inu pre seq. - $V_H$ - 03 - Flag. |

4.3. Construction of *Kluyveromyces marxianus* Episomal Plasmids.

*Kluyveromyces marxianus* is a yeast which is perhaps even more attractive than *K. lactis* for industrial biotechnology, due to its short generation time on glucose (about 45 minutes) and its ability to grow on a wide range of substrates, and its growth at elevated temperatures (Rouwenhorst et al., 1988).

The shuttle vector pUR2434, containing the leu2 marker and the pKD1 plasmid sequences (not yet published European patent application 92203932.6, supra), located on a pUC19 based vector, can be cut with EcoRI(partial) and HindIII to remove the α-galactosidase expression cassette. In this vector the EcoRI-HindIII fragments containing the Vh expression cassettes as described in example 4.1, can be ligated. The resulting plasmids can then be transformed into KMS3, the neat leu2-auxotroph CBS6556 *K. marxianus* strain (Bergkamp, 1993) using the method of Meilhoc et al. (1990).

| | |
|---|---|
| pUR4451 | $P_{inu}$ - Inu prepro seq. - $V_H$ - 03 |
| pUR4451M | $P_{inu}$ - Inu prepro seq. - $V_H$ - 03 - Myc |
| pUR4451F | $P_{inu}$ - Inu prepro seq. - $V_H$ - 03 - Flag |
| pUR4452 | $P_{inu}$ - Inu pre seq. - $V_H$ - 03 |
| pUR4452M | $P_{inu}$ - Inu pre seq. - $V_H$ - 03 - Myc |
| pUR4452F | $P_{inu}$ - Inu pre seq. - $V_H$ - 03 - Flag. |

Figure 15:
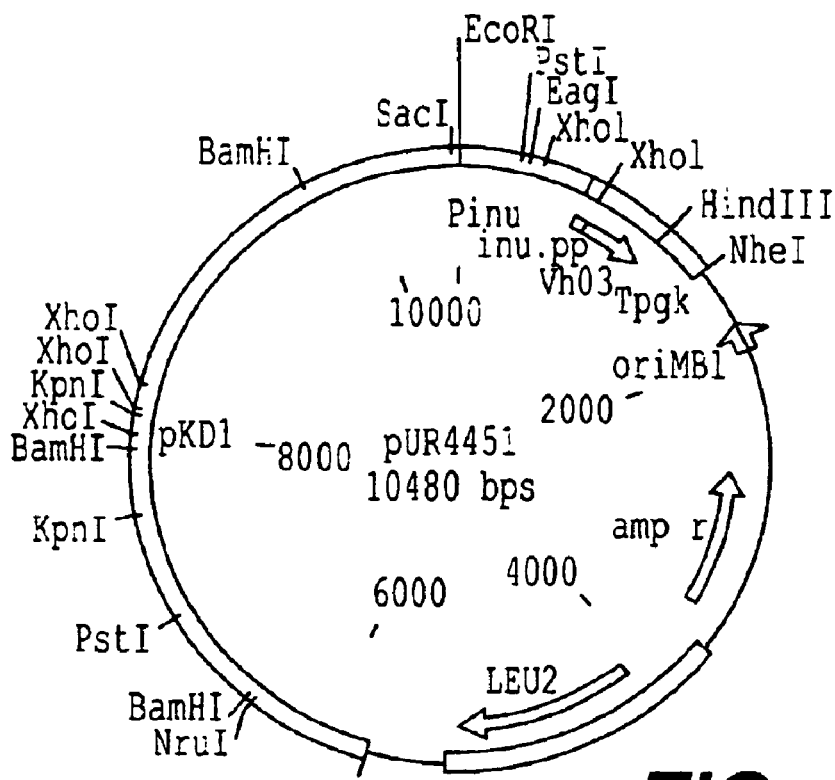

A map of pUR4451 is shown in FIG. 15.

4.4 Construction of *Kluyveromyces marxianus* Multicopy Integration Vectors.

For high and stable expression in *Kluyveromyces marxianus*, the multicopy integration system as described by Bergkamp (1993), can be used. The following cloning route, based on the route for constricting pMIRKM-GAL5 (Bergkamp, 1993), results in suitable expression vectors for production of Vh fragments from Camelidae. The EcoRI-NheI(Klenow filled) fragments of pUR4447,-M,-F and pUR4448,-M,-F containing the Vh fragment expression cassettes as described in example 4.1, can be isolated and ligated in EcoRI-EcoRV digested pIC-20H. From the plasmids obtained in this way, and which are equivalents of the pIC-αgal plasmid, the BamHI-NruI fragment can be isolated and ligated with BamHI-SmaI digested pMIRKM4. The result of this will be expression vectors which are equivalent to pMIRKM-GAL5, and contain a tailed or non-tailed $V_H$ fragment from camel under control of inulinase promoter and secretion signals, in a vector which also contains the *K. marxianus* LEU2-gene with defective promoter, and *K. marxianus* rDNA sequences for targeted integration into the genome. These vectors can be used to transform for example KMS3.

| | |
|---|---|
| pUR4453 | $P_{inu}$ - Inu prepro seq. - $V_H$ - 03 |
| pUR4453M | $P_{inu}$ - Inu prepro seq. - $V_H$ - 03 - Myc |
| pUR4453M | $P_{inu}$ - Inu prepro seq. - $V_H$ - 03 - Flag |
| pUR4454 | $P_{inu}$ - Inu pre seq. - $V_H$ - 03 |
| pUR4454M | $P_{inu}$ - Inu pre seq. - $V_H$ - 03 - Myc |
| pUR4454F | $P_{inu}$ - Inu pre seq. - $V_H$ - 03 - Flag. |

Figure 16:
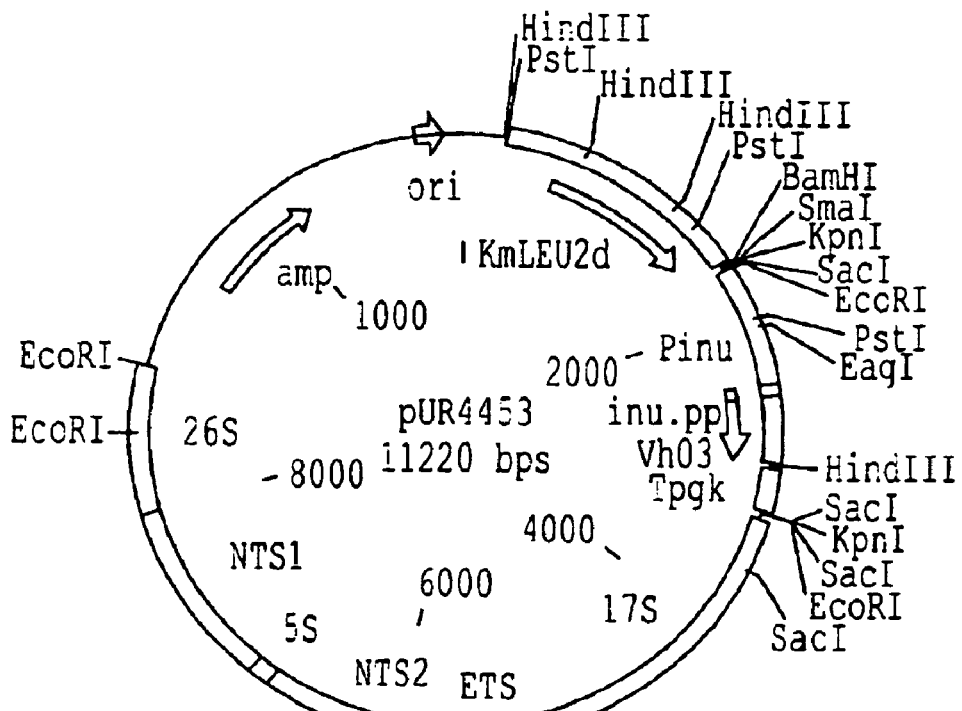

A map of pUR4453 is shown in FIG. 16.

Example 5

Construction of *Hansenula polymorpha* Integrating Vectors for the Expression of (Functionalized) $V_H$ Fragments from Camelidae In search for productive systems able to carry out authentic posttranscriptional processing and overcoming the limitation of higher eukaryotic expression systems, such as high costs, low productivity and the need for stringent control procedures for the detection of contaminating agents could be overcome by the methylotrophic yeast *H. polymorpha*. This strain is able to grow on methanol as its sole carbon and energy source, so the presence of methanol in the growth medium rapidly induces the enzymes of the methanol pathway, such as the key enzymes methanol oxidase (MOX) and dihydroxyacetone synthase (DHAS).

While experiments to express foreign genetic information from an episomal plasmid resulted a low plasmid stability, chromosomal integration is the method of choice (Sierkstra et al., 1991). By utilizing the DNA of the mox gene as integration locus the latter were able to express and secrete α-galactosidase regulated by mox promoter and -terminator. Here, the *S. cerevisiae* SUC2 signal sequence was proven to be efficiently functional for secretion.

Figure 17:
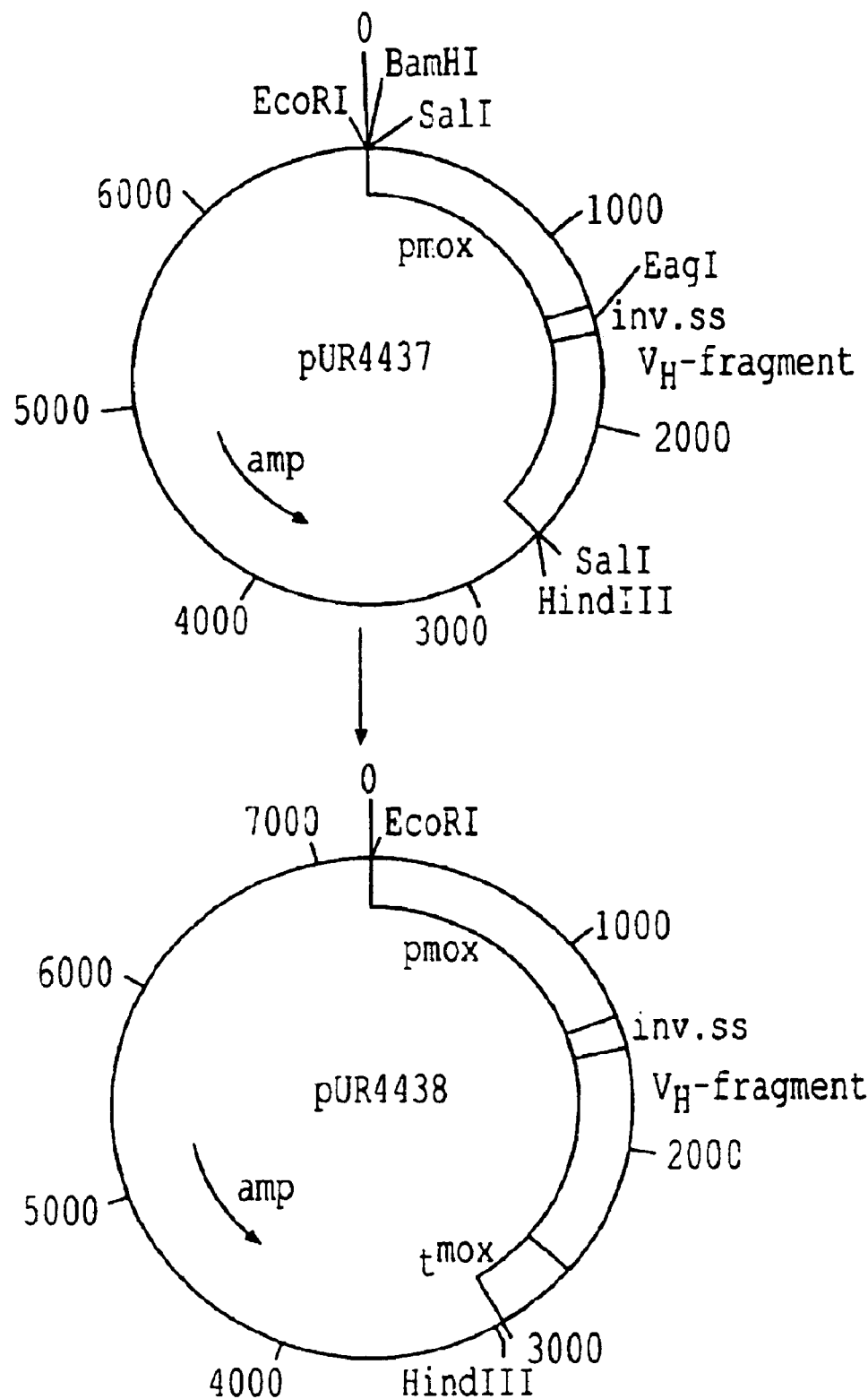

The same approach can be used for expression and secretion of Camelidae $V_H$ antibody fragments. Plasmids analogous to pUR3515 (without an origin of replication functional in yeast) and pUR3517 (containing the HARS2 sequence as origin of replication) can be used as expression vectors (Sierkstra et al., 1991). As a starting vector pUR3501 can be used (Sierkstra et al., 1991) in which by means of site directed mutagenesis (e.g. via PCR technology), an EagI restriction site is introduced at the junction between the invertase (=SUC2) signal sequence and the α-galactosidase. From the resulting plasmid, pUR3501Eag, it is possible to replace the EagI-HindIII fragment comprising the α-galactosidase gene by an EagI-HindIII fragment encoding a (functionalized) antibody fragment, obtained as described in example 1. In case of using the EagI-HindIII fragments of the pUR4421-03 series (example 1), this would result in plasmids pUR4437 (FIG. 17), pUR4437M and pUR4437F. In these plasmids the nucleotide sequence encoding the (functionalized) $V_H$ is preceded by a nucleotide sequence encoding the invertase signal sequence and the max promoter sequence. The obtained plasmids can be digested with BamHI and HindIII and after willing in the sticky ends with Klenow polymerase, the about 2.6 kb fragments can be ligated into plasmid pUR3511 which was digested with SmaI (Sierkstra et al., 1991). In this way the terminator sequence of the max gene can by fused downstream of the $V_H$ encoding sequences. From the thus obtained plasmids, pUR4438 (FIG. 17) EcoRI-HindIII fragments of about 3 kb can be isolated, containing the max promoter, the invertase signal sequence, the (functionalized) $V_H$ fragment and the max transcription terminator. Subsequently these fragments can be cloned into plasmid pUR3513 (no yeast origin of replication) or in pUR3514 (HARS origin of replication) as described by Sierkstra et al (1991), resulting in two sets of plasmids:

| | |
|---|---|
| pUR4439 | $P_{mox}$ - SUC2 sig. seq. - $V_H$ - mox term. -- no origin |
| pUR4439M | $P_{mox}$ - SUC2 sig. seq. - $V_H$ - mox term. -- no origin |
| pUR4439F | $P_{mox}$ - SUC2 sig. seq. - $V_H$ - mox term. -- no origin |
| pUR4440 | $P_{mox}$ - SUC2 sig. seq. - $V_H$ - mox term. -- HARS origin |
| pUR4440M | $P_{mox}$ - SUC2 sig. seq. - $V_H$ - mox term. -- HARS origin |
| pUR4440F | $P_{mox}$ - SUC2 sig. seq. - $V_H$ - mox term. -- HARS origin. |

Figure 18A:
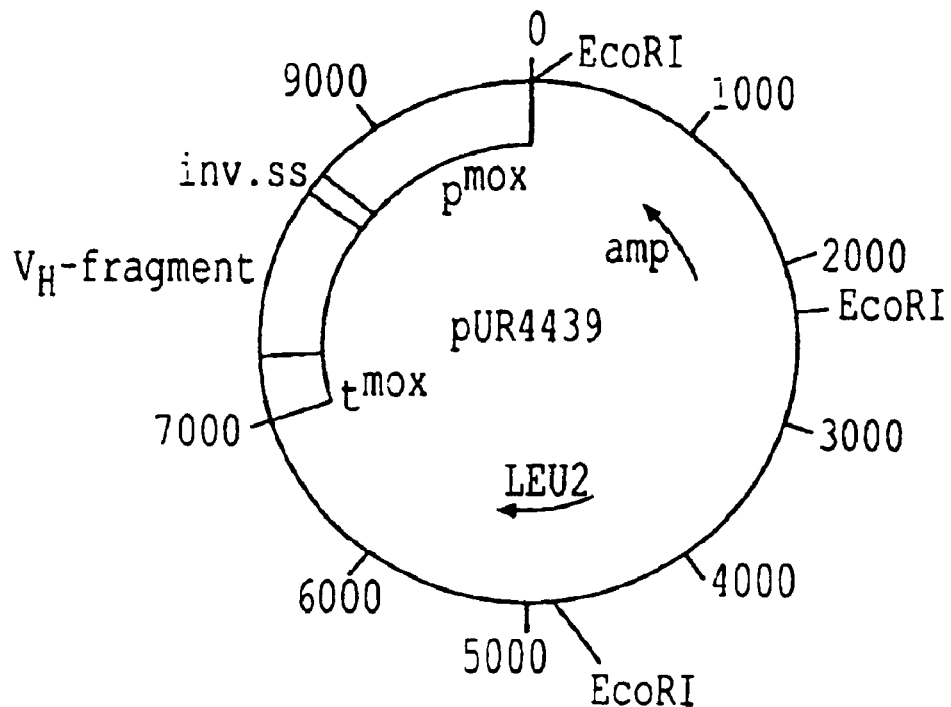
Figure 18B:
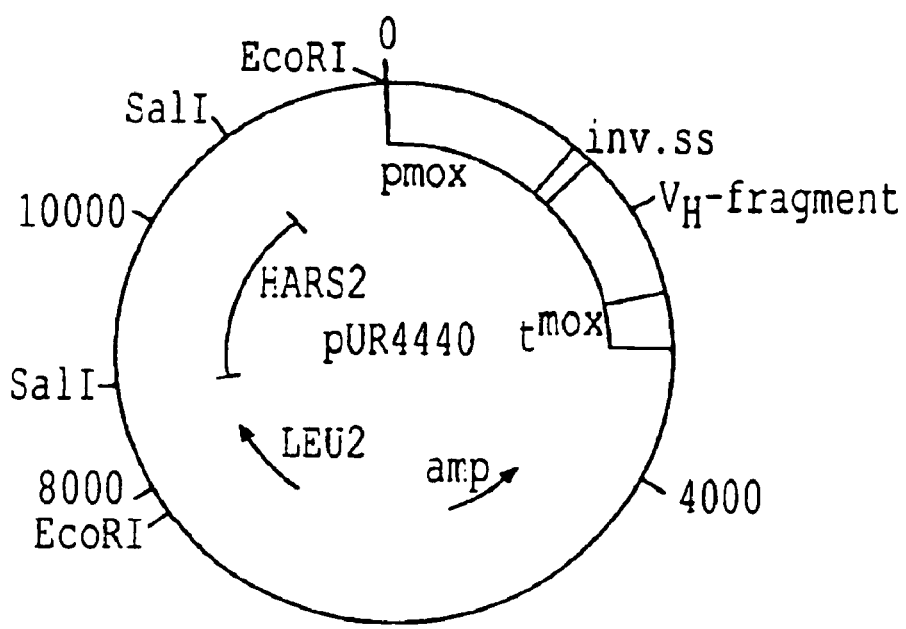

Maps of pUR4439 and pUR4440 are shown in FIG. 18.

Essentially the same can be done with other EagI-HindIII fragment, obtained as described in example 1.

The newly obtained plasmids can be transformed by electroporation of *H. polymorpha* A16 (CBS4732, leu-) and can be selected by growing on selective medium containing 0.68% YNB and 2% glucose. Induction medium should contain 0.5% methanol instead of the glucose.

Example 6

Construction *Aspergillus niger* var. *awamori* Integration Vectors for the Production of $V_H$ Fragments from Camelidae The multiple cloning site of plasmid pEMBL9 (ranging from the EcoRI to the HindIII site) was replaced by it synthetic DNA fragment having the nucleotide sequence as indicated in FIG. 19, see SEQ. ID. NO: 42-45. The 5'-part of the nucleotide sequence contains ai NeiI restriction site followed by the first codons of the Camelidae $V_H$ gene fragment and a XhoI restriction site. The 3'-part encodes for a BstEII restriction site, the last codons of the Camelidae V$_H$ gene, eleven codons of the Myc tail and finally a EcoRI and a AflII site. The resulting plasmid is pUR4432.

After digesting plasmid pB3 with XhoI and EcoRI, a DNA fragment of approximately 425 bp can be isolated from agarose gel. This fragment codes for a truncated V$_H$-Flag fragment, missing the first 5 amino acids of the Camelidae V$_H$. The obtained fragment can be cloned into pUR4432. To this end plasmid pUR4432 can be digested with XhoI and EcoRI, after which the about 4 kb vector fragment was isolated from an agarose gel. Ligation with the about 425 bp fragment resulted in plasmid pUR4433F.

After digesting the plasmids pB3 with XhoI and BstEII, a DNA fragment of approximately 365 bp was isolated from agarose gel. This fragment codes for a truncated V$_H$ fragments, missing the first and last 5 amino acids of the Camelidae V$_H$. The obtained fragment was cloned into pUR4432. To this end plasmids pUR4432 can be digested with XhoI and BstEII, after which the about 4 kb vector fragment was isolated from an agarose gel. Ligation with the about 365 bp fragments resulted in plasmids pUR4433M. In a similar way the XhoI-BstEII fragments of pB9 and pB24 were cloned into the pUR4432 vector fragment, resulting in pUR4434M and pUR4435M, respectively.

Upon digesting pUR4433M or pUR4433F with BstEII and HindIII, the vector fragments of about 4.4 kb can be isolated from agarose gel and religated in the presence of a synthetic linker peptide having the following sequence:

```
BstEII              AflII       HindIII
 GTCACCGTCTCCTCATAATGATCTTAAGGTGATA       (top
                                          strand,
                                          SEQ ID
        GCAGAGGAGTATTACTAGAATTCCACTATTCGA. NO: 50, is
                                          shown
                                          5' to 3';
                                          bottom
                                          strand,
                                          SEQ
                                          ID NO: 51,
                                          is
                                          shown 3'
                                          to 5'
```

In the thus obtained plasmid, pUR4433, the Myc tail or Flag tail sequences are removed and the V$_H$ gene fragment is directly followed by a stop codon.

Analogous as described in example 1.5, it is possible to clone nucleotide sequences encoding longer fragments of the heavy chain immunoglobulins into pUR4432 or to replace the BstEII-AflII fragments of the above mentioned plasmids pUR4433, pUR4433F or pUR4433M with other BstEII-AflII fragments, resulting in frame fusions encoding functionalized V$_H$ fragments, having a C-terminal extension. Upon replacing the NruI-XhoI fragments of pUR4433, pUR4433F or pUR4433M, in frame fusions can be constructed encoding functionalized V$_H$ fragments, having an N-terminal extension.

In the above described constructs an NruI site was introduced before the first codon of the (functionalized) V$_H$ fragment, facilitating an in frame fusion with the precursor-sequence of xylanase, see (not prior-published) WO-A-93/12237, supra. For the construction of Aspergillus expression plasmids, from the plasmids pUR4433F, pUR4433M and pUR4433, respectively, an about 455, 445 and 405 bp NruI-AflII fragment has to be isolated encoding the V$_H$ fragment with a Flag, a Myc or no tail.

Figure 20:
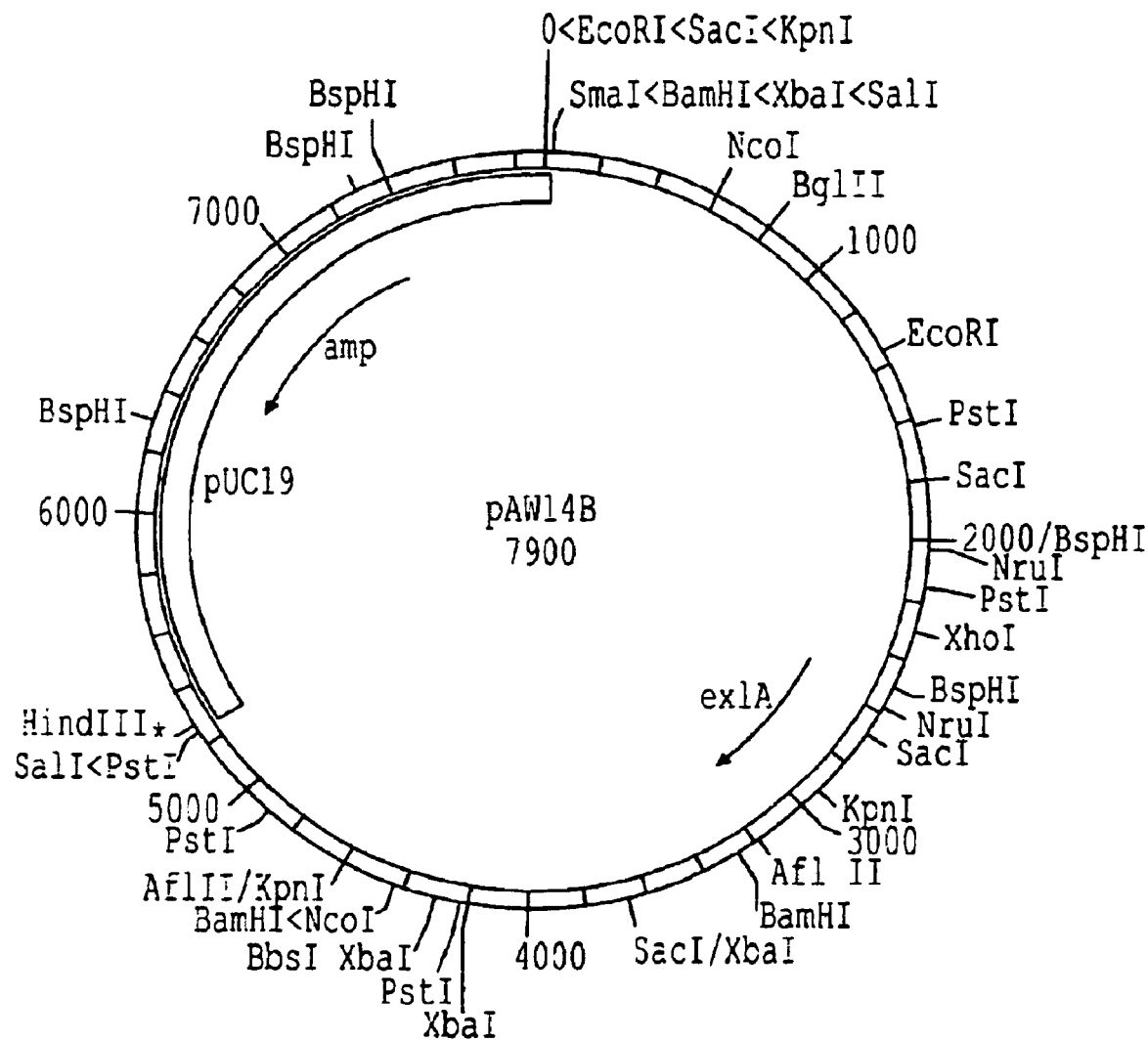
FIG. 20 Schematic drawing of plasmid pAW14B.

Plasmid pAW14B was the starting vector for construction of a series of expression plasmids containing the exlA expression signals and the genes coding for (functionalized) V$_H$ fragments of Camelidae heavy chain antibodies. The plasmid comprises an *Aspergillus niger* var. *awamori* chromosomal 5 kb SalI fragment on which the 0.7 kb exlA gene is located, together with 2.5 kb of 5'-flanking sequences and 2.0 kb of 3'-flanking sequences (see FIG. 20 and (not prior-published) WO-A-93/12237, supra).

Starting from pAW14B, pAW14B-10 was constructed by removing the EcoRI site originating from the pUC19 polylinker, and introducing a NotI site. This was achieved by digesting plasmid pAW14B with EcoRI and after dephosphorylation the linear 7.9 kb EcoRI fragment was isolated. The fragment was religated in the presence of the "EcoRI"-NotI linker:

```
5'-AATTGCGGCCGC-3'.     (see SEQ. ID. NO: 52)
```

Subsequently the AflII site, located downstream of the exlA terminator was removed by partially cleaving plasmid pAW14B-10 and religating the isolated, linearized plasmid after filling in the sticky ends, resulting in plasmid pAW14B-11.

Finally, pAW14B-12 was constructed using pAW14B-11 as starting material. After digestion of pAW14B-11 with AflII (overlapping with the exlA stop codon) and BglII (located in the exl promoter) the ~2.4 kb AflII-BglII fragment, containing part of the exlA promoter and the exlA gene was isolated as well as the ~5.5 kb AflII-BglII vector fragment. After partial digestion of this ~2.4 kb fragment with BspHI (located in the exlA promoter and at the exlA start codon) an about 1.8 kb BglII-BspHI exlA promoter fragment (up to the ATG initiation codon) was isolated and ligated with the about 5.5 kb AflII-BglII vector fragment of pAW14B-11 in the presence of the following adaptor:

```
(BspHI) BbsI        AflII
  CATGCAGTCTTCGGGC           (top strand, SEQ ID NO:
       GTCAGAAGCCCGAATT.     53, is shown 5' to 3';
                             bottom
                             SEQ ID NO: 54, is shown
                             3' to 5'
```

For the construction of the V$_H$ expression plasmids, pAW14B-11 can be partially digested with NruI and digested with AflII, after which the ⁻7 kb vector fragment can be isolated from agarose gel and contains the xylanase promoter, the DNA sequence encoding the xylanase signal sequence and the xylanase terminator. Upon ligation of the NruI-AflII fragments of pUR4433M, pUR4434M and pUR4435M with the pAW14B-11 vector, plasmids pUR4436M, pUR4437M and pUR4438M were obtained, respectively. In these plasmids the Camelidae V$_H$ polypeptides are preceded by the 27 amino acid long precursor sequence of xylanase and followed by the myc-tail (of 11 amino acids; see Examples 13 en 2, FIGS. 6 and 19, and SEQ. ID. NO: 41=45).

In a similar way plasmids can be constructed encoding the V$_H$ fragments followed by the FLAG-tail or without a tail.

After introducing the amdS and pyrG selection markers into the unique NotI site of pUR4436M, pUR4437M and pUR4438M using conventional techniques, e.g. as described in Examples 2 and 3 of (not prior-published) WO-A-93/12237, supra, the plasmids were transferred to *Aspergillus*.

Production of the Camel V$_H$ fragments by the selected transformants was achieved by growing the strains in inducing medium essentially as described in example 2.2 of (not prior-published) WO-A-93/12237, supra. Western blot analysis of the culture medium was performed as described in Example 2.1 above and revealed the presence of the antibody fragments.

Obviously, expression vectors can be constructed in which different promoter systems, e.g. glucoamylase promoter, and/ or different signal sequences, e.g. glucoamylase or glucose oxidase signal sequences, are used.

Example 7

Production of Glucose Oxidase-$V_H$ Fusion Proteins

Glucose oxidase catalyses the oxidation of D-glucose to D-gluconate under the release of hydrogen peroxide. Glucose oxidase genes (box) from *Aspergillus niger* have been cloned (Frederick et al. (1990) J. Biol. Chem. 265 3793, Kriechbaum et al., 1989) and the nucleotide sequences are available from the EMBL data bank under accession numbers J05242 and X16061. The nucleotide sequence of the latter is used as a basis for the following construction route.

Upon cloning the gox gene from *A. niger* it is possible, by applying PCR technology, to introduce convenient restriction sites.

To introduce a BspHI restriction site, overlapping with the ATG initiation codon, the sequence ATC ATG CAG can be changed to ATC ATG AGG. In the same experiment an EcoRI restriction site can be introduced which is located upstream of the BspHI site. This can be achieved by using the following PCR primer:

in the same PCR experiment, in order to introduce a BbsI site, a AflII site and a HindIII site, downstream of the unique SalI site present in the glucose oxidase gene. After digesting the DNA obtained from this PCR experiment with EcoRI and HindIII, an EcoRI-HindIII fragment of about 160 bp can be isolated and cloned into pEMBL9, which was digested with the same enzymes, resulting in plasmid pGOX1.

From pGOX1 an about 140 hp BspHI-AflII fragment can be isolated and introduced into the 7.2 kb BbsI-AflII vector fragment of pAW14B-12, resulting in pAW14B-GOX. In this plasmid, the 5'-part of the gox gene, encoding the first 43 amino acids, is fused in frame with the ATG initiation codon of the exlA gene.

In a second PCR experiment, a MluI restriction site can be introduced near the 3'-end of the gox by changing the sequence TAT GCT TCC to TAC GCG TCC. In the same experiment a HindIII site can be introduced downstream of the MluI site. As a second primer an oligo nucleotide should be used hybridizing upstream of the SalI site. After digesting the DNA obtained from this PCR experiment with SalI and HindIII, an SalI-HindIII fragment of about 1.7 kb can be isolated and cloned into pEMBL9, which was digested with the same enzymes, resulting in plasmid pGOX2. Upon digesting pGOX2 with MluI and HindIII, an about 5.7 kb vector fragment can be isolated.

From the plasmids pUR4433, pUR4433F, pUR4433M and the like, XhoI-HindIII fragments can be isolated, encoding

```
          EcoRI      BspHI
5'-TCACTGAATTCGGGATC ATG AGG ACT CTC CTT GTG AGC TCG CTT-3'.  (see SEQ. ID. NO: 55)
```

A second PCR primer, having the following sequence can be used:

```
              AflII      BbsI    SalI
5'-ATGTCACAAAGCTTAAGCACGAAGACA GTC GAC CGT GCG GCC GGA GAC-3'   (see SEQ. ID. NO: 56)
         HindIII
``` the truncated Camelidae $V_H$ fragment with or without a tail sequence, and missing the first 4-6 N-terminal amino acids (see Example 1). These fragments can be ligated into the 5.7 kb pGOX2 vector fragment by using MluI-XhoI adaptors. These adaptors are designed in such a way that they result in an in frame fusion between the 3'-end of the gox gene and the restored $V_H$ gene fragment, optionally intersected with a DNA sequence encoding a peptide linker sequence.

An example of these designed adaptors is:

```
 MluI                                                XhoI
 CGCGTCCATGCAGTCCTCAGGTGGATCATCCCAGGTGAAACTGC        (top strand, SEQ ID NO:
      AGGTACGTCAGGAGTCCACCTAGTAGGGTCCACTTTGACGAGCT   57, is shown 5' to 3';
           S   M   Q |S   S   G   G   S  |Q   V   K   L   L   E   bottom strand, SEQ ID NO:
                                                     58, is shown 3' to 5';
                                                     the
                                                     encoded amino acid
                                                     sequence is SEQ ID NO: 59
``` which encodes for the last amino acids of GOX, an SSGGSS linker sequence (see SEQ. ID. NO: 62) and the N-terminal amino acids of the Camel $V_H$ fragment of pB3. Instead of the SSGGSS linker (see SEQ. ID. NO: 62) it is possible to use other linkers such as the repeated sequence linkers described in the above indicated European patent application 92402326.0, e.g. a repeated sequence Pro-X, with X being any amino acid, but preferably Gln, Lys or Glu, the sequence containing advantageously at least 3 repeats of Pro-X and especially a fragment composed of a 12-fold repeat of the sequence of Pro-X.

In case the about 435 hp XhoI-HindIII fragment of pUR4433M is used in combination with the above described adaptor, this would result in pGOX2-03M. From this plasmid a SalI-AflII fragment of about 2.1 kb encoding the C-terminal part of glucose oxidase followed by the linker peptide, the Camel $V_H$ fragment of pB3 and finally the Myc tail.

Upon digesting pAW14B-GOX partially with BbsI, and with AflII, the about 7.4 kb vector fragment can be isolated. This fragment contains the xylanase promoter, the DNA sequence encoding the N-terminal part of glucose oxidase and the xylanase promoter. Due to the digestion with BbsI, a SalI sticky end is created, corresponding with the SalI restriction site originally present in the gox gene. Ligation of the SalI-AflII vector fragment with the about 2.1 kb SalI-AflII fragment of pGOX2-03M, resulting in pUR4441M. This expression plasmid encodes for a single chain polypeptide comprising the glucose oxidase enzyme, the (functionalized) Camel $V_H$ fragment and the Myc tail.

Introduction of this type of expression plasmids in *Aspergillus* can be achieved essentially as described in example 6.

As the naturally occurring glucose oxidase is a homodimeric enzyme, it might be expected that a fusion protein, comprising glucose oxidase and an antibody fragment as a C-terminal extension, has an increased avidity for the antigen/antibody binding, if this fusion protein is produced as a homodimer. Alternatively, it is possible to produce heterodimers, consisting of one glucose oxidase molecule connected to a $V_H$ fragment and one wild type glucose oxidase molecule. This can be achieved by producing with the same strain both wild type glucose oxidase and the fused glucose oxidase-$V_H$ fragment, or by mixing the two different homodimers produced by different strains under conditions whereby the mixture of dimers are dissociated and subsequently associated.

Example 8

Engineering of Camelidae $V_H$ Fragments 8.1 Random and Targeted Random Mutagenesis.

After expressing a number of different Camelidae $V_H$ fragments in lower eukaryotic host organisms as described above, or in prokaryotes, fragments produced in relative higher amounts can be selected. Upon subjecting the XhoI-BstEII gene fragments to a (targeted) random mutagenesis procedure, it might be possible to further improve special characteristics of the $V_H$ fragment, e.g. further improvement of the production level, increased stability or increased affinity.

To this end the following procedure might be followed.

Upon replacing the polylinker of the phagemid vector pHEN1 (Hoogenboom et al., 1991) located on a NcoI-NotI fragment by a new polylinker having the following sequence:

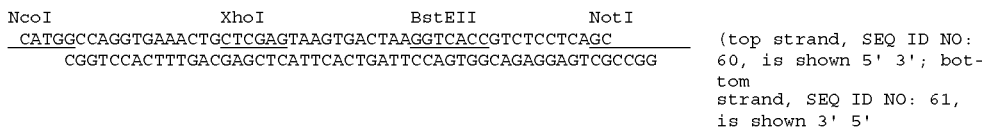

(top strand, SEQ ID NO: 60, is shown 5' 3'; bottom strand, SEQ ID NO: 61, is shown 3' 5' it becomes possible to introduce XhoI-BstEII fragments encoding truncated Camelidae $V_H$ fragments in the phagemid.

Following mutagenesis of the $V_H$ encoding sequence (random mutagenesis) or a specific part thereof (targeted random mutagenesis), the mutated $V_H$ fragments can be expressed and displayed on the phage surface in essentially the same way as described by Hoogenboom et al. (1991). Selecting phages displaying (mutant) $V_H$ fragments, can be done in different ways, a number of which are described by Marks et al. (1992). Subsequently, the mutated XhoI-BstEII fragments can be isolated from the phagemid and introduced into expression plasmids for yeast or fungi as described in previous examples.

Upon producing the mutant $V_H$, fragments by these organisms, the effects of the mutations on production levels. $V_H$ fragment stability or binding affinity can be evaluated easily and improved $V_H$ fragments can be selected.

Obviously, a similar route can be followed for larger antibody fragments. With similar procedures the activity of catalytic antibodies can be improved.

8.2 Site-Directed or Designed Mutagenesis

As an alternative to the methods described above in Example 8.1 it is possible to use the well-known technique of site-directed mutagenesis. Thus, designed mutations, preferably based on molecular modelling and molecular dynamics, can be introduced in the $V_H$ fragments, e.g. in the framework or in the CDRs.

8.3 Construction $V_H$ Fragments with Regulatable Binding Efficiencies.

For particular applications, the possibility to regulate the binding capacity of antibody fragments might be necessary. The introduction of metal ion binding sites in proteins is known from the literature e.g. Pessi et al. (1993). The present inventors envisage that the introduction of a metal binding site in an antibody fragment by rational design can result in a regulatable antibody fragment, when the metal binding site is introduced at a position such that the actual binding of the metal ion results in a conformational change in the antibody fragments due to which the binding of the antigen to the antibody fragment is influenced. Another possibility is that the presence of the metal prevents antigen binding due to steric hindrance.

8.4 Grafting of Cdr Regions on the Framework Fragments of a Camelidae $V_H$ Fragment.

Grafting of CDR fragments onto framework fragments of different antibodies or fragments thereof is known from the literature (see Jones et al. (1986), WO-A-92/15683, and WO-A-92/01059). In these cases the CDR fragments of murine antibody fragments were grafted onto framework fragments of human antibodies. The sole rationale behind the "humanization" was to increase the acceptability for therapeutic and/or diagnostic applications in human.

Essentially the same approach can however also be used for a totally different purpose. Although antibody fragments share some homology in the framework areas, the production levels vary considerably.

Once an antibody or in antibody fragment, e.g. a Camelidae $V_H$ fragment, has been identified, which can be produced to high levels by an production organism of interest, this antibody (fragment) can be used as a starting point to construct "grafted" antibody (fragments), which can be produced in high levels and have an other specificity as compared to the original antibody (fragment). In particular cases it might be necessary to introduce some modifications in the framework fragments as well in order to obtain optimal transitions between the framework fragments and the CDR fragments. For the determination of the optimal transitions molecular dynamics and molecular modelling can be used.

To this end a synthetic gene, encoding the "grafted $V_H$" fragment, can be constructed and introduced into an expression plasmid. Obviously it is possible to adapt the codon usage to the codons preferred by the host organism.

For optimization of the "grafted $V_H$" fragment, the procedure as described in example 8.1 can be followed.

Literature Mentioned in the Specification Additional to that Mentioned in the Above Given Draft Publication Adair, J. R. et al., WO-A-92/01059 (CELLTECH Ltd, 1992)

Beggs (1978) Nature 275 104

Bendig, M. M. et al. WO-A-92/15683 (MERCK PATENT GmbH, 1992)

Bergkamp, R. J. M, Kool, I. M., Geerse, R. H., Planta, R. J. (1992) Multiple copy integration of the α-galactosidase gene from *Cyamopsis tetragonoloba* into the ribosomal DNA of *Kluyveromyces lactis*. Current Genetics 21 365-370

Bergkamp, R. J. M, PhD Thesis Free University of Amsterdam (1993), Heterologous gene expression in *Kluyveromyces* yeasts Better et al. (1988) Science 240 1041-1043

Bird et al., (1988) Science 242 423-426

Cabilly, S. et al., EP-A-0125023 (GENENTECH, 1984)

Denthe, et al. (1983) Nucl. Acids Res. 11 1645

Fellinger, A. J. et al., EP-A-0255153 (UNILEVER, 1988)

Frederick et al. (1990) J. Biol. Chem. 265 3793

Giuseppin, M. L. F., Lopes. M. T. S., Planta, R. J., Verbakel, J. M. A., Verrips, C. T. (1991) Process for preparing 0.1 protein by a yeast transformed by multicopy integration of an expression vector. PCT application WO 91/00920 (UNILEVER)

Harmsen, M. M., Langedijk. A. C., van Tuinen, E., Geerse, R. H., Raué, H. A., Maat, J., (1993) Effect of pmr1 disruption and different signal sequences on the intracellular processing and secretion of *Cyamopsis tetragonolaba* α-galactosidase by *S. cerevisiae*. Gene 125 115-123

Hollenberg, C. et al., EP-A-0096430 (GIST-BROCADES N.V., 1983))

Hoogenboom H. R., Griffiths, A. D., Johnson, K. S., Chiswell, D. J., Hudson, P., and Winter, G. (1991) Multi-subunit proteins on the surface of filamentous phage: methodologies for displaying, antibody (Fab) heavy and light chains. Nucleic Acids Research 15 4133-4137

Jones et al (1986) Nature 321 522

Kriechbaum et al. (1989) FEBS Lett. 255 63

Ledeboer, A. M. et al., EP-A-0173378 (UNILEVER, 1986)

Leenhouts, C. J. et al., EP-A-0487159 (UNILEVER, 1992)

Lerner, Benkovic and Schultz, (1991) Science 252 659-667

Marks, J. D., Hoogenboom, H. R., Griffiths, A. D., and Winter, G. (1992) Molecular evolution of proteins on filamentous phage. J. Biol. Chem. 267 16007-16010

Meilhoc, E., Masson, J., Teissié, J. (1990) High efficiency transformation of intact yeast cells by electric pulses. Bio/Technology 8 223-227

Mitchell, P., (1979) Science 206 1148-1159)

Pessi et al. (1993) Nature 362 367.

Rouwenhorst, R. J., Visser, L. E., van der Baan, Scheffers, W. A, van Dijken, J. P. (1988) Production, distribution and kinetic properties of inulinase in continuous culture of *Kluyveromyces marxianus* CBS 6556. Appl. Environm. Microbiol. 54 1131-1137.

Sierkstra, L. N., Verbakel, J. M. A. and Verrips, C. T. (1991) Optimisation of a host/vector system for heterologous gene expression by *Hansenula polymorpha*. Current Genetics 19 81-87.

Skerra et al. (1988) Science 240 1938

Takahashi et al. (1993) Science 259 1460-1463);

Teeri et al., WO-A-93/02198 (TECH. RES. CENT. FINLAND, publ. 4 Feb. 1993)

Van Gorcom, R. F. M. et al., WO-A-91/19782 (UNILEVER, 1991)

Wu et al. (1993) Bio/Technology 11 71

Zhou et al. (1991) Nucleic Acids Research 19 6052

Additional references to prior-filed but not prior-published patent applications, which are incorporated herein by reference:

not prior-published PCT application EP 92/02896, filed 9 Dec. 1992 with priority date of 9 Dec. 1991 (UNILEVER/R. J. Gouka et al.), now publicly available as WO-A-93/12237 not prior-published EP application 92202080.5, filed 8 Jul. 1992 (UNILEVER/F. M. Klis et al.), now publicly available as International (PCT) patent application WO-A-94/01567)

not prior-published EP application 92402326.0, filed 21 Aug. 1992 (C. Casterman & R. Hamers), now publicly available as EP-A1-0 584 421 not yet published EP application 92203932.6, filed 11 Dec. 1992 (UNILEVER/H. Y. Toschka & J. M. A. Verbakel).

Information on deposits of micro-organisms under the Budapest Treaty is given in Example 1 on page 23, lines 23-25 above. In agreement with Rule 28 (4) EPC, or a similar arrangement for a State not being a Contracting State of the EPC, it is hereby requested that a sample of such deposit, when requested, will be submitted to an expert only.

The invention claimed is:

1. A process for the production of an antibody fragment or functionalized fragment which contains at least a variable domain of a heavy chain and which fragment is capable of binding antigen, comprising: transforming a lower eukaryotic host which is a mould or a yeast belonging to the genera *Saccharomyces, Kluyveromyces, Hansenula,* or *Pichia* with an expressible DNA sequence encoding the antibody fragment or functionalized fragment, wherein the antibody fragment or functionalized fragment is derived from a heavy chain immunoglobulin of Camelidae, is devoid of light chains, and lacks a $C_H1$ domain and features for interacting with corresponding light chains, expressing and isolating said antibody fragment or functionalized antibody fragment.

2. The process according to claim 1, in which the antibody fragment or functionalized fragment from a heavy chain immunoglobulin of Camelidae comprises a complementarity determining region (CDR) different from the CDR belonging to the natural antibody ex Camelidae grafted on the framework of the variable domain of the heavy chain immunoglobulin ex Camelidae.

3. The process according to claim 1, in which the functionalized antibody fragment comprises a fusion protein with another polypeptide.

4. The process according to claim 1, wherein the antibody fragment or functionalized fragment incorporates amino acid sequence of framework regions of a heavy chain immunoglobulin of Camelidae.

5. The process according to claim 1, in which the DNA sequence encodes a modified heavy chain antibody fragment or functionalized fragment derived from Camelidae made by random or directed mutagenesis or both.

6. The process according to claim 5, in which the resulting antibody fragment or functionalized fragment is modified such that it is better adapted for production by the host cell, it is optimized for secretion by the lower eukaryotic host into the fermentation medium, its binding properties ($k_{on}$ and $k_{off}$) are optimized, it has acquired a metal chelating activity, or its physical stability is improved.

7. The process according to claim 1, wherein the heavy chain immunoglobulin is a catalytic immunoglobulin raised in Camelidae.

* * * * *